US010993933B2

(12) United States Patent
Colledge et al.

(10) Patent No.: US 10,993,933 B2
(45) Date of Patent: *May 4, 2021

(54) ORAL DOSAGE FORMS OF BENDAMUSTINE

(71) Applicant: ASTELLAS DEUTSCHLAND GMBH, Munich (DE)

(72) Inventors: Jeffrey Colledge, AC Leiderdorp (NL); Margaretha Olthoff, AC Leiderdorp (NL)

(73) Assignee: Astellas Deutschland GmbH, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/753,483

(22) Filed: Jun. 29, 2015

(65) Prior Publication Data
US 2015/0374670 A1  Dec. 31, 2015

Related U.S. Application Data

(63) Continuation of application No. 13/701,269, filed as application No. PCT/EP2011/002764 on Jun. 1, 2011, now abandoned.

(30) Foreign Application Priority Data

Jun. 2, 2010 (EP) .................................... 10075231
Mar. 14, 2011 (EP) .................................... 11075047

(51) Int. Cl.
*A61K 47/10* (2017.01)
*A61K 9/48* (2006.01)
*A61K 31/4184* (2006.01)
*A61K 9/00* (2006.01)
*A61K 45/06* (2006.01)
*A61K 47/02* (2006.01)
*A61K 9/14* (2006.01)

(52) U.S. Cl.
CPC ........ *A61K 31/4184* (2013.01); *A61K 9/0053* (2013.01); *A61K 9/48* (2013.01); *A61K 9/485* (2013.01); *A61K 9/4858* (2013.01); *A61K 45/06* (2013.01); *A61K 47/02* (2013.01); *A61K 47/10* (2013.01); *A61K 9/145* (2013.01)

(58) Field of Classification Search
None
See application file for complete search history.

(56) References Cited

U.S. PATENT DOCUMENTS

| 6,709,675 | B1 * | 3/2004 | Lombardin | A61K 9/4833 424/452 |
| 2003/0044434 | A1 * | 3/2003 | Gao | A61K 9/1075 424/400 |
| 2003/0077297 | A1 * | 4/2003 | Chen | A61K 9/1617 424/400 |
| 2003/0105141 | A1 * | 6/2003 | Gao | A61K 9/1075 514/341 |
| 2003/0108575 | A1 * | 6/2003 | Lu | A61K 9/0095 424/400 |
| 2004/0157928 | A1 | 8/2004 | Kim et al. | |
| 2005/0260186 | A1 * | 11/2005 | Bookbinder | A61K 38/47 424/94.61 |
| 2006/0052270 | A1 | 3/2006 | Patel et al. | |
| 2006/0128777 | A1 * | 6/2006 | Bendall | A61K 31/4184 514/394 |
| 2006/0135405 | A1 * | 6/2006 | Rischer | A61K 9/0019 514/10.4 |
| 2008/0075767 | A1 * | 3/2008 | Jin | A61K 9/1075 424/455 |
| 2009/0017024 | A1 * | 1/2009 | Estok | A61K 31/05 514/1.1 |
| 2009/0264488 | A1 | 10/2009 | Cooper et al. | |

(Continued)

FOREIGN PATENT DOCUMENTS

KR  10-2009-0036346 A  4/2009
WO  2002/083105 A2  10/2002

(Continued)

OTHER PUBLICATIONS

Remington: The Science and Practice of Pharmacy 21st Edition, p. 116, 2005.*

(Continued)

*Primary Examiner* — Robert T. Crow
*Assistant Examiner* — John P Nguyen
(74) *Attorney, Agent, or Firm* — Morgan, Lewis & Bockius LLP

(57) ABSTRACT

In the present invention there is provided a pharmaceutical composition for oral administration which comprises bendamustine or a pharmaceutically acceptable, ester, salt or solvate thereof as an active ingredient, and a pharmaceutically acceptable excipient and which shows a dissolution of the bendamustine of at least 60% in 20 minutes, 70% in 40 minutes and 80% in 60 minutes, as measured with a paddle apparatus at 50 rpm according to the European Pharmacopoeia in 500 ml of a dissolution medium at a pH of 1.5. The invention further relates to the above pharmaceutical composition for use for the oral treatment of a medical condition which is selected from chronic lymphocytic leukemia, acute lymphocytic leukaemia, chronic myelocytic leukaemia, acute myelocytic leukaemia, Hodgkin's disease, non-Hodgkin's lymphoma, multiple myeloma, breast cancer, ovarian cancer, small cell lung cancer and non-small cell lung cancer.

18 Claims, 1 Drawing Sheet

(56) References Cited

U.S. PATENT DOCUMENTS

| | | | |
|---|---|---|---|
| 2009/0324552 A1* | 12/2009 | Lichter | A61K 31/00 424/93.4 |
| 2010/0273730 A1* | 10/2010 | Hsu | A61K 9/1075 514/49 |
| 2010/0297194 A1 | 11/2010 | Catron et al. | |
| 2010/0310661 A1* | 12/2010 | Chen | A61K 9/10 424/489 |

FOREIGN PATENT DOCUMENTS

| | | |
|---|---|---|
| WO | 2006/065392 A2 | 6/2006 |
| WO | 2007/072061 A2 | 12/2006 |
| WO | 2006/076620 A2 | 7/2008 |
| WO | 2008/124617 A2 | 10/2008 |
| WO | 2009/147212 A1 | 12/2009 |
| WO | 2010/063476 A2 | 6/2010 |
| WO | 2010/063493 A1 | 6/2010 |
| WO | 2010/126676 A1 | 11/2010 |

OTHER PUBLICATIONS

Strickley, "Solubilizing Excipients in Oral and Injectable Formulations", Pharmaceutical Research, vol. 21, No. 2, pp. 201-230, Feb. 2004 (Year: 2004).*

Toronto Research Chemicals, Safety Data Sheet—Bendamustine hydrochloride, 6 pages, publication date Nov. 5, 2014 (Year: 2014).*

Barman et al, Bendamustine, Drugs, Adis International Ltd., 61(5), 631-638 (2001).

Ribosepharm: "Product Monograph ribosepharm passage," (2005).

Preiss, "The pharmacokinetics of bendamustine (Cytostasane) in humans]," Pharmazie 40(11), 782-784 (1985) (see English abstract).

Cole et al, "Studies using a non-ionic surfactant-containing drug delivery system designed for hard gelatin capsule compatibility," International Journal of Pharmaceutics, vol. 88, issues 1-3, 211-220 (1992).

Lawrence et al, "Microemulsion-based media as novel drug delivery system," Advanced Drug Delivery Reviews, 45 89-121 (2000).

* cited by examiner

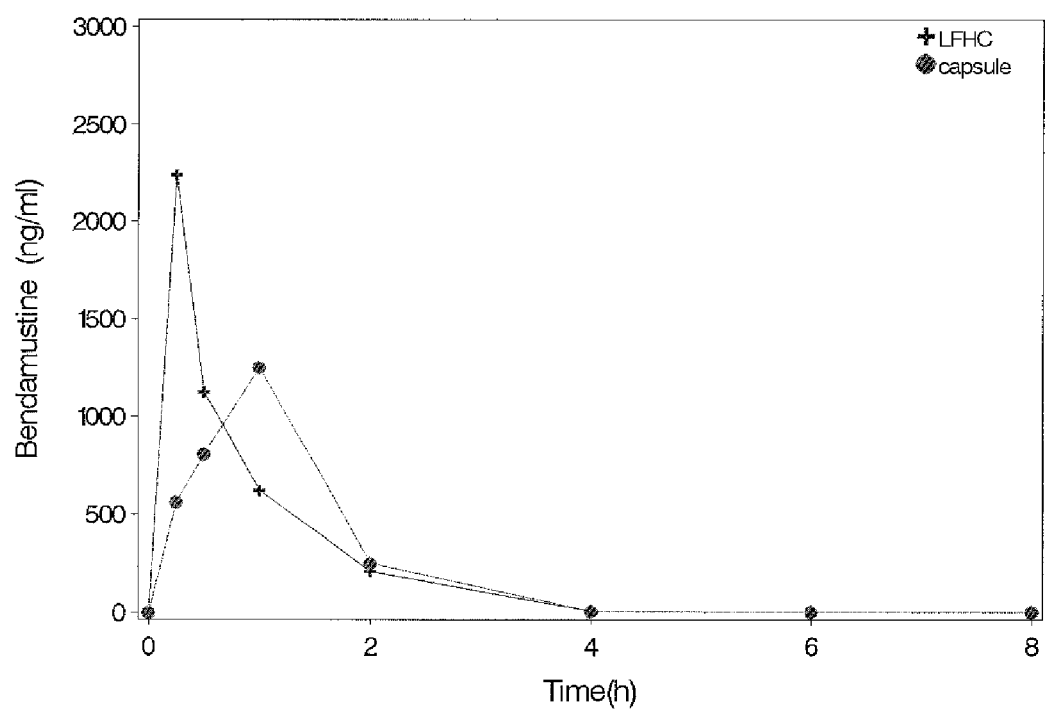

ORAL DOSAGE FORMS OF BENDAMUSTINE

The present invention relates to oral dosage forms comprising bendamustine or a pharmaceutically acceptable ester, salt or solvate thereof.

BACKGROUND OF THE INVENTION

Bendamustine (4-[5-[bis(2-chloroethyl)amino]-1-methyl-benzimidazo-2-yl]butanoic acid, a nitrogen mustard) is an alkylating agent with bifunctional alkylating activity. It corresponds to the following formula (I):

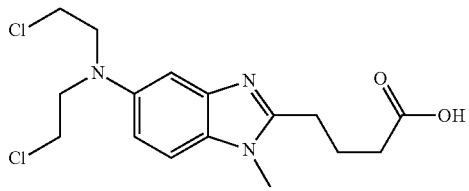

Bendamustine appears to be free of any cross-resistance with other alkylating agents, which offers advantages in terms of chemotherapy for patients who have already received treatment with an alkylating agent.

Bendamustine was initially synthesized in the German Democratic Republic (GDR). The hydrochloric acid of bendamustine was the active ingredient in a commercial product available from 1971 to 1992 under the trade name CYTOSTASAN. Since that time, it has been marketed in Germany under the trade name RIBOMUSTIN and has been widely used to treat chronic lymphocytic leukemia, non-Hodgkin's lymphoma and multiple myeloma.

The marketed product contains a lyophilized powder of bendamustine hydrochloride which is reconstituted with water for injection yielding a concentrate. This is subsequently diluted with an aqueous solution of 0.9% sodium chloride resulting in the final solution for infusion. This final solution is administered to the patient by intravenous infusion over a period of about 30 to 60 minutes.

Hydrolysis of the bis-2-chloroethylamino-group of bendamustine in water leads to reduction in potency and to impurity formation (B. Maas et al. (1994) in Pharmazie 49: 775-777). Hence administration, usually in a hospital or at least under medical supervision, must occur immediately after reconstitution of the lyophilized powder. Furthermore, reconstitution has been reported to be difficult. It may require more than 30 minutes. Further, it is burdensome and time-consuming for the healthcare professionals responsible for reconstituting the product in the 2 step process.

Preiss et al. (1985) in Pharmazie 40:782-784 compared the pharmacokinetics of bendamustine hydrochloride in plasma in 7 patients after intravenous and oral administration respectively in a dose ranging between 4.2-5.5 mg/kg. The intravenous infusion prepared from the commercially available CYTOSTASAN product was given over 3 minutes, whereas oral medication in an equivalent dose was taken in the form of capsules, containing 25 mg of bendamustine hydrochloride. The number of capsules to be taken by the patients varied from 10-14, referring to absolute oral doses of 250-350 mg. After oral administration maximal plasma levels were detectable within 1 hour. The mean oral bioavailability was calculated to be 57%, ranging from 25% to 94% indicating a large inter-individual variability (% CV=44%).

Weber (1991) (Pharmazie 46(8): 589-591) investigated the bioavailability of bendamustine hydrochloride in B6D2F1-mice and found that the absorption of the drug from the gastro-intestinal tract is incomplete resulting in a bioavailability of about 40% only.

US 2006/0128777 A1 describes methods for treating cancers, characterised by death-resistant cells and bendamustine-containing compositions in general. Amongst these compositions are oral dosage forms, which are capsules, tablets, pills, powders or granules, wherein the active compound may be admixed with at least one inert excipient, such as sucrose, lactose or starch. However, specific compositions were not exemplified.

Bendamustine hydrochloride is only sparingly soluble in water at a pH of 2.0 and is slightly or very slightly soluble in a range of organic solvents. A good solubility has been observed however in ethanol and methanol. Therefore it is not surprising that the oral bendamustine compositions, as investigated by Preiss et al. and Weber gave rise to relatively poor bioavailability results and a large inter-individual variability.

In view of the stability problems with the intravenous marketed formulation, once reconstituted with water, and in order to improve the patient compliance there has been a long-felt need for a stable dosage-form comprising bendamustine which is easy to administer to the patient and which provides good bioavailability without large inter- and intra-individual variability.

SUMMARY OF THE INVENTION

In order to solve the above problems the present inventors have carried out detailed investigations. They finally succeeded in obtaining the stable pharmaceutical compositions according to the invention. These compositions are suitable for oral administration and comprise bendamustine or a pharmaceutically acceptable ester, salt or solvate thereof as an active ingredient, and at least one pharmaceutically acceptable excipient, which compositions apart from having a good stability also have an appropriate dissolution profile.

BRIEF DESCRIPTION OF THE FIGURE

FIG. 1 shows the mean plasma concentration vs. time curve obtained after administering bendamustine hydrochloride in the form of the prior art capsule (reference example 1) and the liquid filled hard capsule formulation of Example 2 to dogs. It is apparent from FIG. 1 that the liquid filled hard capsule formulation provides for a higher maximum concentration of bendamustine, as compared with the prior art reference capsule formulation.

DETAILED DESCRIPTION OF THE INVENTION

The present invention relates to a pharmaceutical composition for oral administration, the composition comprising bendamustine or a pharmaceutically acceptable, ester, salt or solvate thereof as an active ingredient, and a pharmaceutically acceptable excipient, which is a non-ionic hydrophilic surfactant.

An embodiment is a pharmaceutical composition, comprising bendamustine or a pharmaceutically acceptable ester, salt or solvate thereof and a pharmaceutically acceptable excipient, which is a non-ionic hydrophilic surfactant, wherein the composition is suitable for oral administration by including it into a hard gelatine capsule.

A further embodiment is a pharmaceutical composition for oral administration in a solid dosage-form, which is a hard gelatine capsule, the composition comprising bendamustine or a pharmaceutically acceptable ester, salt or solvate thereof and a pharmaceutically acceptable excipient, which is a non-ionic hydrophilic surfactant, wherein the use of the specific non-ionic hydrophilic surfactant leads to a dissolution of bendamustine from the composition of at least 80% after 60 minutes, as measured with a paddle apparatus at 50 rpm during 30 minutes and at 200 rpm during a further 30 minutes according to the European Pharmacopoeia in 500 ml of a dissolution medium at a pH of 1.5. Preferably the use of the specific non-ionic surfactant results in a dissolution profile of at least 60% bendamustine dissolved after 20 minutes, 70% dissolved after 40 minutes and 80% dissolved after 60 minutes, as measured with a paddle apparatus at 50 rpm according to the European Pharmacopoeia in 500 ml of a dissolution medium at a pH of 1.5. More preferably the use of the specific non-ionic hydrophilic surfactant results in a dissolution of bendamustine from the composition of at least 80% after 30 minutes and most preferably results in a dissolution profile of at least 60% bendamustine dissolved after 10 minutes, 70% after 20 minutes and 80% after 30 minutes, both when measured with a paddle apparatus at 50 rpm according to the European Pharmacopoeia in 500 ml of a dissolution medium at a pH of 1.5.

A preferred embodiment is a pharmaceutical composition for oral administration in a solid dosage-form, which is a hard gelatine capsule, the composition comprising bendamustine hydrochloride and a pharmaceutically acceptable excipient, which is a non-ionic hydrophilic surfactant, wherein the use of the specific non-ionic surfactant results in a dissolution of at least 60% bendamustine dissolved after 10 minutes, 70% after 20 minutes and 80% after 30 minutes, as measured with a paddle apparatus at 50 rpm according to the European Pharmacopoeia in 500 ml of a dissolution medium at a pH of 1.5.

The present invention is based on the surprising finding that stable compositions of bendamustine having a specific and desirable dissolution profile can be obtained by incorporating into the pharmaceutical composition certain non-ionic surfactants. It has been found that, if a pharmaceutically acceptable non-ionic hydrophilic surfactant is used as an excipient in a pharmaceutical composition comprising bendamustine or a pharmaceutically acceptable ester, a salt or a solvate thereof as an active ingredient, a particularly favourable profile of the composition with respect to stability and degradation products, dissolution, bioavailability and a reduced variability in bioavailability is achieved. The incorporation of non-ionic hydrophilic surfactants, which are a polyethoxylated castor oil or a derivative thereof (in particular macrogol glycerol hydroxystearate or polyoxyl-35-castor oil), a block copolymer of ethylene oxide and propylene oxide (in particular PLURONIC L44 NF or POLOXAMER 124; PLURONIC L35 or POLOXAMER 105; PLURONIC L64 or POLOXAMER 184), a macrogol glycerol cocoate (GLYCEROX HE), a macrogol 15 hydroxy stearate (SOLUTOL HS15), Polysorbate 20 and 40, but are not limited hereto, in bendamustine-containing compositions results in a dissolution profile of at least 60% bendamustine dissolved after 20 minutes, 70% dissolved after 40 minutes and 80% dissolved after 60 minutes, as measured with a paddle apparatus at 50 rpm according to the European Pharmacopoeia in 500 ml of a dissolution medium at a pH of 1.5 and preferably it results in a dissolution of at least 60% bendamustine dissolved after 10 minutes, 70% after 20 minutes and 80% after 30 minutes.

Below further details of the invention are presented.

The expression "pharmaceutically acceptable ester thereof" describes any pharmaceutically acceptable ester of bendamustine, such as esters with alkyl alcohols and sugar alcohols. Examples of the alkyl alcohols are $C_{1-6}$-alkyl alcohols such as methanol, ethanol, propanol, isopropanol, butanol and tert-butanol. Examples of the sugar alcohols are mannitol, maltitol, sorbitol, erythritol, glycol, glycerol, arabitol, xylitol and lactitol. Preferred examples of the bendamustine esters are the ethyl ester, the isopropyl ester, the mannitol ester and the sorbitol ester, most preferred is the ethylester thereof.

The expression "pharmaceutically acceptable salt thereof" describes any pharmaceutically acceptable salt of bendamustine that administered to a patient (directly or indirectly) provides bendamustine. This term further comprises the pharmaceutically acceptable salt of a bendamustine ester. Nevertheless, it will be considered that the pharmaceutically non-acceptable salts also are included within the limits of this invention since these compounds can be useful in the preparation of pharmaceutically acceptable salts. For example, pharmaceutically acceptable salts of bendamustine are synthesized from the corresponding compound that contains an acid or basic group, by conventional chemical methods. Generally, these salts are, for example, prepared by means of the reaction of free acidic or basic forms of these compounds in a stoichiometric amount with a corresponding base or acid in water or an organic solvent or a mixture of both. Nonaqueous media like ether, ethyl acetate, isopropanol or acetonitrile are generally preferred. Examples of acids which may be used for the salt formation of pharmaceutically acceptable salts of bendamustine include inorganic acids such as hydrochloride, hydrobromide, hydriodide, sulphuric, nitric, and phosphoric acids, and organic acids such as acetic, maleic, fumaric, citric, oxalic, succinic, tartaric, malic, lactic, methylsulphonic and p-toluenesulphonic acids. Pharmaceutically acceptable salts of bendamustine may be derived from either inorganic or organic bases to yield ammonium salts; alkali metal salts (lithium, sodium, potassium, etc.), alkaline earth salts like calcium or magnesium, aluminium salts, lower alkylamine salts like methylamine or ethylamine salts, lower alkyl-diamine salts like ethylenediamine salts, ethanolamine, N,N-dialkyleneethanolamine, triethanolamine, and glucamine salts, as well as basic salts of amino acids. Especially preferred are acid salts prepared from the hydrochloride, the hydrobromide, and the hydroiodide, whereas the hydrochloride salt is the most preferred pharmaceutically acceptable salt of bendamustine. The pharmaceutically acceptable salts are produced by conventional techniques well-known in the art.

The expression "pharmaceutically acceptable solvate thereof" describes any pharmaceutically acceptable solvate that, administered to a patient (directly or indirectly) provides bendamustine. This term further comprises the pharmaceutically acceptable solvate of a bendamustine ester. Preferably, the solvate is a hydrate, a solvate with an alcohol such as methanol, ethanol, propanol, or isopropanol, a solvate with an ester such as ethyl acetate, a solvate with an ether such as methyl ether, ethyl ether or THF (tetrahydrofuran) or a solvate with DMF (dimethylformamide), of which a hydrate or a solvate with an alcohol such as ethanol is more preferred. A solvent for constituting the solvate is preferably a pharmaceutically acceptable solvent.

It is especially preferred that the active ingredient in the invention's compositions is bendamustine or a pharmaceutically acceptable salt thereof. It is most preferred that the active ingredient is bendamustine hydrochloride.

The dose of the active ingredient in the pharmaceutical composition may readily be determined by the skilled artisan depending on the patient's condition, sex, body weight, body surface area, or age, especially depending on the patient's body weight and body surface area. It is preferred that the daily dosage ranges from about 50 to about 1000 mg, preferably from about 100 to about 500 mg of the active ingredient. The daily dosage may be taken as a single dose or as multiple doses such as twice or three-times daily, most preferably as a single daily dose. The daily dose may be taken once a week or several times a week. The dosage form may contain the amount of a single daily dose or parts thereof. It is preferred that the dosage form of the present invention comprises about 10 to about 1000 mg, preferably about 25 to about 600 mg, more preferably about 50 to about 200 mg and most preferably about 100 mg of the active ingredient.

As used herein, the term "non-ionic hydrophilic surfactant" refers to an amphiphilic compound having a polar, hydrophilic group and a non-polar, lipophilic group or chain and wherein the hydrophilic and lipophylic properties of the compound are characterised by the so-called Hydrophilic-Lipophilic Balance (HLB) value. The non-ionic surfactant to be used for preparing the compositions of the present invention has an HLB-value between 10 and 20. The non-ionic surfactant further has a melting point, pour point or melting range between 5° C. and body temperature (37° C.). The non-ionic surfactant can be in a liquid or a semi-solid state at room temperature. The non-ionic hydrophilic surfactant is a carrier for the bendamustine active ingredient, which can be present in a dissolved form, a suspended form or partly in a dissolved and partly in a suspended form.

The non-ionic hydrophilic surfactants that are advantageously used for the preparation of the compositions according to the present invention preferably have an HLB-value of between 10 and 19, more preferably between 12 and 18, and are liquid at room temperature or have a melting point, pour point or melting range of between just below room temperature (20° C.) and body temperature, preferably at approximately 30° C. Examples thereof can be found in the group of a polyethoxylated castor oil or derivatives thereof, in the group of block copolymers of ethylene oxide and propylene oxide and in the group of Polysorbates.

In one embodiment, the non-ionic surfactant is a polyethoxylated castor oil. One example of a polyethoxylated castor oil is sold under the tradename CREMOPHOR. CREMOPHOR products of various purities and viscosities are produced and may be used in the present invention. In particular macrogol glycerol hydroxystearate (CREMOPHOR RH 40) and polyoxyl-35-castor oil (CREMOPHOR EL or CREMOPHOR ELP) can be used. CREMOPHOR ELP and CREMOPHOR EL are known as nonionic solubilizers and emulsifiers, produced by reacting castor oil with ethylene oxide in a molar ratio of 1 to 35. They have an HLB-value of 12-14 and a melting point of 26° C. Depending on the ambient temperature these products can be characterised as either semi-solid or as a medium viscosity liquid. Macrogol glycerol hydroxystearate (commercially available as CREMOPHOR RH 40) is a semi-solid material at 25° C., having a viscosity range at the same temperature of 20-40 cps (as a 30% aqueous solution). It is known as a nonionic solubiliser and emulsifier. It is produced by reacting castor oil with ethylene oxide in a molar ratio of 1 to 45. Its HLB-value ranges from 14-16 and the melting range is from 20-28° C. In experiments it was shown that macrogol glycerol hydroxystearate can advantageously be used on its own for the preparation of compositions according to the present invention.

As has been demonstrated, the products sold under the tradenames CREMOPHOR A6 and CREMOPHOR A25, despite the fact that these are non-ionic hydrophilic surfactants having an HLB-value of between 10 and 20, are not suitable carriers in accordance with the present invention, because they have a melting point or melting point range that is above the indicated temperature (=37° C.).

PLURONIC block copolymers consist of ethylene oxide and propylene oxide blocks and are characterised by the following formula: $HO(C_2H_4O)a(C_3H_6O)_b(C_2H_4O)_aH$. The ethylene oxide units have a hydrophilic character whereas the propylene oxide units have a lipophilic character Variations in the number of hydrophilic ethylene oxide units and lipophilic propylene oxide units results in copolymers with a different molecular mass and different hydrophilic-lipophilic-balance (HLB). An example of a block copolymer of propylene oxide ("PEO")-polypropylene oxide ("PPO") meeting the requirements of the HLB-value and the melting point or pour point or melting range for making the compositions according to the present invention is PLURONIC L44 wherein a and b blocks have the following values for PLURONIC L44NF/Poloxamer 124: a=12 and b=20. Other suitable block copolymers of ethylene oxide and propylene oxides are: PLURONIC L35, PLURONIC L64 and PLURONIC L43. All are liquids at room temperature.

As has been demonstrated, the products sold under the tradenames PLURONIC 68 or POLOXAMER F188 and PLURONIC 127 or POLOXAMER F407, are not suitable carriers in accordance with the present invention, because these have an HLB-value outside the range 10-20 and a melting point or melting point range above the indicated temperature (=37° C.).

Polysorbates, a class of emulsifiers, are oily liquids derived from PEG-ylated sorbitan (a derivative of sorbitol) esterified with fatty acids. Examples are:
  Polysorbate 20 (Polyoxyethylene (20) sorbitan monolaurate)
  Polysorbate 40 (Polyoxyethylene (20) sorbitan monopalmitate)
  Polysorbate 60 (Polyoxyethylene (20) sorbitan monostearate)
  Polysorbate 80 (Polyoxyethylene (20) sorbitan monooleate)

The number following the polyoxyethylene part refers to the total number of oxyethylene —$(CH_2CH_2O)$— groups found in the molecule. The number following the polysorbate part is related to the type of fatty acid associated with the polyoxyethylene sorbitan part of the molecule. Monolaurate is indicated by 20, monopalmitate is indicated by 40, monostearate by 60 and monooleate by 80. It should be noted that Polysorbate 20 and Polysorbate 40 are suitable as a carrier for bendamustine hydrochloride but not Polysorbate 81, 65 and 61.

Further non-ionic hydrophilic surfactants that can be used as carriers for bendamustine or a pharmaceutically acceptable ester, salt or solvate thereof can be found in in the examples.

Except for macrogol glycerol hydroxystearate the abovementioned non-ionic surfactants are all liquids having a viscosity value which may be too low to avoid sedimentation of the bendamustine hydrochloride. The additional problem to be solved was to find an excipient or a combination of excipients that would allow for a total value for the viscosity of the mixture that would be high enough to avoid segregation of the bendamustine chloride when added to the mixture.

Therefore the compositions according to the present invention, that contain a liquid non-ionic surfactant, advantageously further contain a viscosity improving agent. Suitable viscosity-improving agents include a powder such as colloidal silicon dioxide (commercially available under the trademark AEROSIL) or a semi-solidwaxy material, such as lauroyl macrogol glycerides (commercially available under the trademark GELUCIRE 44/14). The amount of the powder or the semi-solid material to be added to the liquid non-ionic surfactant depends on the viscosity of the liquid non-ionic surfactant. Different concentrations have been tested in order to find the minimum suitable amount of viscosity improving agent to be added to visually avoid sedimentation of the active ingredient. Typical relative concentrations of colloidal silicon dioxide to be added range from about 1% to about 8%, but are preferably as low as 1.7% or 2.0% in order not to have a negative impact on the dissolution characteristics of the active ingredient. Typical relative concentrations of lauroyl macrogol glycerides range from 5 to 50%, and are preferably about 10% and about 45%.

Preferred compositions according to the present invention, are disclosed in example 4 and comprise bendamustine hydrochloride in combination with:
  macrogol glycerol hydroxystearate;
  ethylene oxide/propylene oxide block copolymer (PLURONIC L44 NF or POLOXAMER 124; PLURONIC L35 or POLOXAMER 105; PLURONIC L64 or POLOXAMER 184; PLURONIC L43 or POLOXAMER 123), optionally in combination with colloidal silicon dioxide or lauroyl macrogol glycerides (GELUCIRE 44/14);
  polyoxyl-35-castor oil, optionally in combination with lauroyl macrogol glycerides (GELUCIRE 44/14);
  Polysorbates 20 and 40;
  GLYCEROX HE (macrogol glycerol cocoate) and SOLUTOL HS15 (macrogol 15 hydroxy stearate).

Further, the compositions of the present invention can include additional excipients, in particular protective agents, such as anti-oxidants and antimicrobial preservatives, e.g. methyl-, ethyl- and propylparaben, as illustrated in examples 1-3. The antioxidant may be d-alpha tocopherol acetate, dl-alpha tocopherol, ascorbyl palmitate, butylated hydroxyanidole, ascorbic acid, butylated hydroxyanisole, butylated-hydroxyquinone, butylhydroxyanisol, hydroxycoumarin, butylated hydroxytoluene, ethyl gallate, propyl gallate, octyl gallate, lauryl gallate, or mixtures thereof. The anti-oxidant is preferably added to compositions containing macrogol glycerol hydroxystearate or polyoxyl-35-castor oil.

The pharmaceutical compositions according to the present invention are advantageously filled into a capsule, as described in the examples, which capsule can then easily be taken by the patient.

Two types of capsule are commonly used and are classified according to the nature and flexibility of the capsule shell: soft and hard capsules.

Soft capsules are single unit solid dosage forms comprising a liquid or semi-solid fill. They are formed, filled and sealed in one operation using a rotary die process. They have been used as unit dose containers for liquids for many years, whereas hard capsules have conventionally been used for the delivery of solids in the form of powders, granulates and pellets. Hard capsules are single unit dosage forms, consisting of a cap and a body, which are manufactured separately and which are supplied empty for filling.

Soft capsules are most commonly manufactured from gelatine, to which a plasticiser, usually glycerine or sorbitol, is added in addition to water. Also for hard capsules the most commonly used polymer is gelatine. An additional component is water, which acts as a plasticiser. This component however may be responsible for degradation of active ingredients, such as bendamustine hydrochloride. Therefore as an alternative hard capsules may be manufactured from hydroxypropylmethyl cellulose.

Both soft and hard capsules in addition can include colouring agents and opacifiers.

The preferred type of capsule for the compositions according to the present invention is the hard capsule and more in particular the hard gelatine capsule.

Ideally, the materials to be filled into the capsule are fluid at room temperature, which would avoid heating during the filling operation. Generally, heating could result in an easy degradation of the active component.

In principle numerous excipients are available for filling into hard capsules, but in addition to biopharmaceutical considerations, the chemical and physical stability of the final dosage-form are also important to consider, as well as the dissolution profile to produce a safe, effective and stable dosage-form.

Generally, fill formulations for hard capsules may be Newtonian liquids, such as oils, thixotropic or shear thinning gels or semi-solid matrix products that are filled at elevated temperatures and in which the active ingredient is either dissolved or suspended as a fine dispersion. In principle any excipient or mixture of excipients can be used provided that the viscosity of the fill material confirms to the requirements of the filling process. The uniformity of capsule fill weights is important. Further fill formulations should not show stringing and should allow for a clean break from the dosing nozzle.

It has surprisingly been found that the compositions according to the present invention can be advantageously administered in hard gelatine capsules. The particular non-ionic hydrophilic surfactants, selected from the group consisting of a polyethoxylated castor oil or derivative thereof and a block copolymer of ethylene oxide/propylene oxide, and in particular from the group consisting of macrogol glycerol hydroxystearate, polyoxyl-35-castor oil and PLURONIC L44 or POLOXAMER 124, if incorporating bendamustine or a pharmaceutically acceptable ester, salt, or solvate thereof, and after incorporation into hard gelatine capsules result in achieving a good stability, a good dissolution profile and a good bioavailability.

To the contrary, if macrogol glycerol hydroxystearate is used in combination with a liquid material, such as bis-diglyceryl polyacyladipate-1 (commercially available as SOFTISAN 645) and ethylene oxide/propylene oxide block copolymer (commercially available under the names PLURONIC L44 NF or Poloxamer 124), the dissolution profile of bendamustine is deteriorated as compared to compositions containing macrogol glycerol hydroxystearate only. Further it is to be noted that CREMOPHOR A 25 (ceteareth-25 or macrogol (25) cetostearyl ether) and CREMOPHOR A 6 (ceteareth-6 and stearylalcohol or macrogol (6) cetostearyl ether) cannot be used as the non-ionic surfactant. Also other commonly used excipients for the preparation of liquid filled capsule preparations were shown to provide no satisfactory results.

The stability of an aqueous solution of bendamustine is strongly influenced by the pH. A significant hydrolytic decomposition of this compound is observed at pH values higher than about 5. At pH>5, the decomposition proceeds rapidly and the resulting content of by-products is high in this pH range. The main hydrolysis products are 4-[5-[(2-Chloroethyl)-(2-hydroxy-ethyl)amino]-1-methyl-benzimidazo-2-yl]-butanoic acid (HP1), 4-[5-[Bis(2-hydroxyethyl)amino]-1-methyl-benzimidazo-2-yl]-butanoic acid (HP2) and 4-(5-Morpholino-1-methylbenzimidazol-2-yl)-butanoic acid (HP3):

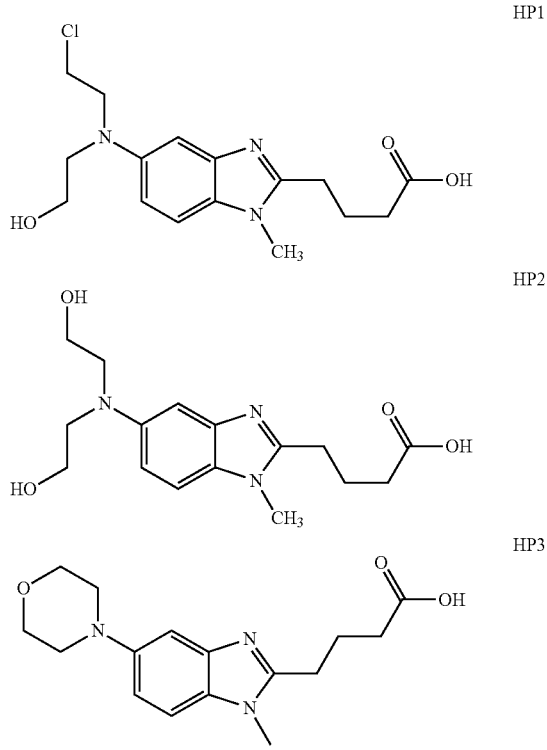

Absorption of an orally administered drug usually happens from the stomach, the small intestine and/or the large intestine. The pH in the stomach is about 1 to 3.5, in the small intestine about 6.5 to 7.6, and in the large intestine about 7.5 to 8.0. Accordingly, for a compound like bendamustine which is prone to degradation in aqueous environments with a pH higher than 5, it is highly preferable that it is absorbed in the stomach, and does not pass through to the small or even the large intestine, in order to avoid decomposition. Hence there is a need for a pharmaceutical composition from which the bendamustine is absorbed completely or at least to a high extent in the stomach, thereby avoiding or reducing the degradation of the bendamustine in the small or large intestine.

It has surprisingly been found that it is possible to solve this problem by using the present pharmaceutical compositions. These compositions comprising bendamustine hydrochloride in a pharmaceutically acceptable excipient, which is a non-ionic hydrophilic surfactant, selected from the group consisting of a polyethoxylated castor oil or derivative thereof and a block copolymer of ethylene oxide and propylene oxide, surprisingly show a fast dissolution, and in particular a dissolution of the bendamustine of at least 60% in 20 minutes, 70% in 40 minutes and 80% in 60 minutes, and preferably of at least 60% in 10 minutes, 70% in 20 minutes and 80% in 30 minutes, as measured with a paddle apparatus at 50 rpm according to the European Pharmacopoeia in an artificial gastric fluid. The artificial gastric fluid as used herein refers to a solution prepared by dissolving 2 g of sodium chloride in 1000 ml of water and then adjusting the pH to 1.5±0.05 with 5 N hydrochloric acid.

Further they have shown to be stable, when put in accelerated stability testing. This is surprising since it has been shown that:
in a reference capsule formulation (see reference example 1) containing bendamustine hydrochloride only in a hard gelatin capsule, when stored at 40° C./75% RH (glass vial open) and 50° C., degradation products were formed within one month of storage. In the case of open vials with 40° C. and 75% RH (relative humidity) the amount of hydrolysis product HP1 was increased by a factor of 4 after one month of storage. For the closed vials the HP1 content is even higher.
in the capsule formulations of reference examples 2, 3 and 4, when stored at 40° C./75% RH (closed glass vial), degradation products were formed within one month of storage and increased upon further storage.

The total time of a drug to pass the stomach to the small intestine is between about 20 minutes to 5 hours, usually between about 30 minutes to 3 hours. Thus pharmaceutical compositions according to this invention advantageously should reduce the degradation of bendamustine in the patient since the bendamustine is released and dissolved to a major extent while in the stomach. Thus even an improved bioavailability of the bendamustine containing compositions according to the invention may be expected.

In a further aspect of this invention the oral pharmaceutical compositions may be used for the treatment or prevention of relapse of a medical condition in a human or animal, preferably a human, which medical condition is selected from chronic lymphocytic leukemia (abbreviated as CLL), acute lymphocytic leukaemia (abbreviated as ALL), chronic myelocytic leukaemia (abbreviated as CML), acute myelocytic leukaemiam (abbreviated as AML), Hodgkin's disease, non-Hodgkin's lymphoma (abbreviated as NHL), multiple myeloma, breast cancer, ovarian cancer, small cell lung cancer, non-small cell lung cancer, and an autoimmune disease.

The present invention also comprises a method of treatment or prevention of relapse of a medical condition selected from chronic lymphocytic leukemia, acute lymphocytic leukaemia, chronic myelocytic leukaemia acute myelocytic leukaemia, Hodgkin's disease, non-Hodgkin's lymphoma, multiple myeloma, breast cancer, ovarian cancer, small cell lung cancer, non-small cell lung cancer, and an autoimmune disease, in a human or animal body comprising administering to the human or animal body in need thereof an effective amount of the pharmaceutical preparation of this invention. Preferably the medical condition is non-Hodgkin's lymphoma.

In another aspect the of this invention the pharmaceutical composition may be administered in combination with at least one further active agent, wherein said further active agent is given prior, concurrently, or subsequently to the administration of the pharmaceutical composition. This at least one further active agent is preferably an antibody specific for CD20 (an examples is rituximab or ofatumumab), an anthracyclin derivative (an example is doxorubicin or daunorubicin), a vinca alkaloid (an example is vincristine), a platin derivative (an example is cisplatin or carboplatin), daporinad (FK866), YM155, thalidomide and analogues thereof (an example is lenalidomide), or a proteasome inhibitor (an example is bortezumib).

The pharmaceutical composition of this invention may also be administered in combination with at least one corticosteroid, wherein said corticosteroid is given prior, concurrently, or subsequently to the administration of the pharmaceutical composition. Examples of the corticosteroids are prednisone, prednisolone and dexamethasone.

The advantage of the compositions according to the present invention further is, that the active ingredient(s), optionally in admixture with one or more excipients, do not need to be provided with a coating in order to further mask the taste of such ingredient and/or to protect the same against possible harmful effects by light and/or moisture such as oxidation, degradation, or to prevent that the subject may experience damage of the oral mucosa, due to the interaction with the active ingredient.

The following examples further illustrate the invention. It will be apparent to the skilled person that these examples are solely for illustrative purposes and must not be considered to limit the invention.

EXAMPLES

1. Capsule Formulations

Reference Example 1: Bendamustine Capsule Formulation (Prior Art)

20.0±1 mg of bendamustine hydrochloride were weighed into the body of an empty hard gelatine capsule, and put into a clear glass HPLC vial (6 ml) of Agilent. Capsules were closed by placing the cap on top of the body and slight pushing.

Capsules were stored at 40° C./75% RH (glass vial open) or 50° C. (glass vial closed). The amount of bendamustine hydrochloride and of related substances was measured with HPLC (column: Zorbax Bonus-RP, 5 μm; temperature of column oven: 30° C.; temperature of autosampler: 5° C.; detector: 254 nm). The results are shown in Table 1:

TABLE 1

Related substances and assay of bendamustine HCl (residual content) in bendamustine capsules

| Storage condition | Related substances | T = 0 | T = 1 month | T = 0 | T = 1 month |
|---|---|---|---|---|---|
| 40° C./ 75% RH (open vial) | HP1 | 0.10 | 0.45 | 99.64 | 98.83 |
| | NP1*[1] | 0.02 | 0.02 | | |
| | BM1Dimer*[1] | 0.06 | 0.42 | | |
| | BM1EE*[1] | 0.13 | 0.11 | | |
| | HP2 | n.d.*[2] | n.d. | | |
| | HP3 | n.d. | n.d. | | |
| 50° C. (closed vial) | HP1 | 0.10 | 1.46 | 99.64 | 97.51 |
| | NP1 | 0.02 | 0.02 | | |
| | BM1Dimer | 0.06 | 0.24 | | |
| | BM1EE | 0.13 | 0.12 | | |
| | HP2 | n.d. | n.d. | | |
| | HP3 | n.d. | n.d. | | |

*[1]NP1: 4-[6-(2-Chloroethyl)-3,6,7,8-tetra-hydro-3-methyl-imidazo[4,5-h]-[1,4]benzothiazin-2-yl] butanoic acidBM1Dimer: 4-{5-[N-(2-Chloroethyl)-N-(2-{4-[5-bis(2-chloroethyl)amino-1-methylbenzimidazol-2-yl]butanoyloxy}ethyl)amino]-1-methylbenzimidazol-2-yl}butanoic acid
BM1EE: 4-[5-[Bis(2-chloroethyl)amino]-1-methyl-benzimidazo-2-yl] butanoic ethyl ester
*[2]n.d.: not detectable, i.e. beyond detection limit (area percentage less than 0.05%)

Reference Example 2

TABLE 2a

Bendamustine powder mixture for capsules

| Component | mg/dosage-form | Relative Content % |
|---|---|---|
| bendamustine hydrochloride | 55.1 | 21.09 |
| Mannitol | 141.4 | 54.11 |
| Microcrystalline cellulose (AVICEL PH101) | 25.0 | 9.57 |
| Crosscarmellose sodium (AC-DI-SOL) | 12.5 | 4.78 |
| Colloidal silicon dioxide (AEROSIL 200) | 1.0 | 0.38 |
| Talc | 18.8 | 7.19 |
| Stearic acid | 7.5 | 2.87 |
| Sum | 261.3 | 100 |

For a batch size of 1000 capsules all excipients except for colloidal silicon dioxide and stearic acid were loaded into a Somakon vessel (5 L). Bendamustine was added and blending was conducted for 4 minutes at 1000 rpm (wiper 10 rpm). The resulting blend was sieved through a 0.5 mm sieve. The vessel was reloaded with the blend and colloidal silicon dioxide was added. Blending was conducted for 2 minutes at the afore-mentioned conditions. Thereafter stearic acid was added and blending was continued for 1 minute. The blend was subsequently sieved through a 0.5 mm sieve, reloaded into the vessel and blended for another 30 seconds, all at the same conditions.

The blend was transferred to a capsule filling machine (Zanassi AZ 5) and filled into hard gelatine capsules (size 2) (mean mass: 259.5 mg (begin)-255.3 mg (end)) and hypromellose capsules (size 2) (mean mass: 255.8 (begin)-253.4 mg (end)) respectively. Capsules were stored at 40° C./75% RH in a closed glass vial. The amount of bendamustine hydrochloride as well as of related substances, like degradation products, by-products of synthesis were measured with HPLC (column: Zorbax Bonus-RP, 5 μm; temperature of column oven: 30° C.; temperature of autosampler: 5° C.; detector: 254 nm). The results are shown in Table 2b (filled in hypromellose capsules) and 2c (filled in gelatine capsules).

TABLE 2b

Bendamustine powder mixture in hypromellose capsules: Related substances and assay of bendamustine HCl (residual content)

| Storage condition | Related substances | T = 0 | T = 2 months | T = 0 | T = 2 months |
|---|---|---|---|---|---|
| 40° C./ 75% RH (closed vials) | HP1 | 0.18 | 0.87 | 99.49 | 97.92 |
| | HP2 | n.d. | 0.38 | | |
| | HP3 | n.d. | 0.08 | | |
| | NP1 | n.d. | n.d. | | |
| | BM1Dimer | 0.09 | 0.14 | | |
| | BM1EE | 0.16 | 0.14 | | |
| | Unid RRT 0.65*[3] | n.d. | 0.05 | | |
| | Unid RRT 0.68 | n.d. | 0.06 | | |
| | Unid RRT 0.70 | n.d. | 0.19 | | |
| | Unid RRT 0.77 | n.d. | 0.05 | | |
| | Unid RRT 0.93 | n.d. | 0.05 | | |

*[3]Unidentified compound peak at relative retention time of 0.65 as compared to main peak TABLE 2c Bendamustine powder mixture in gelatine capsules: Related substances and assay of bendamustine HCl (residual content)

| Storage condition | Related substances | T = 0 | T = 2 months | T = 0 | T = 2 months |
|---|---|---|---|---|---|
| | | | | Bendamustine HCl [% area] | |
| 40° C./75% RH (closed vials) | HP1 | 0.25 | 1.25 | 99.30 | 97.79 |
| | HP2 | n.d. | 0.11 | | |
| | HP3 | n.d. | <0.05 | | |
| | NP1 | n.d. | n.d. | | |
| | BM1Dimer | 0.14 | 0.14 | | |
| | BM1EE | 0.16 | 0.14 | | |
| | Unid RRT 0.65 | n.d. | 0.05 | | |
| | Unid RRT 0.68 | 0.07 | 0.05 | | |
| | Unid RRT 0.70 | n.d. | 0.30 | | |
| | Unid RRT 0.77 | n.d. | n.d. | | |
| | Unid RRT 0.93 | n.d. | n.d. | | |

Reference Example 3

TABLE 3a

Bendamustine powder mixture for capsules

| Component | mg/dosage-form | Relative Content % |
|---|---|---|
| bendamustine hydrochloride | 55.1 | 21.09 |
| Lactose anhydrous | 141.4 | 54.11 |
| Microcrystalline cellulose (AVICEL PH112) | 25.0 | 9.57 |
| Crosscarmellose sodium (AC-DI-SOL) | 12.5 | 4.78 |
| Colloidal silicon dioxide (AEROSIL 200) | 1.0 | 0.38 |
| Talc | 18.8 | 7.19 |
| Stearic acid | 7.5 | 2.87 |
| Sum | 261.3 | 100 |

For 1000 capsules all excipients except for colloidal silicon dioxide and stearic acid were loaded into a Somakon vessel (5 L). Bendamustine was added and blending was conducted for 4 minutes at 1000 rpm (wiper 10 rpm). The resulting blend was sieved through a 0.5 mm sieve. The vessel was reloaded with the blend and colloidal silicon dioxide was added. Blending was conducted for 2 minutes at the afore-mentioned conditions. Thereafter stearic acid was added and blending was continued for 1 minute. The blend was subsequently sieved through a 0.5 mm sieve, reloaded into the vessel and blended for another 30 seconds, all at the same conditions.
The blend was transferred to a capsule filling machine (Zanassi AZ 5) and filled into hard gelatine capsules (size 2) (mean mass: 257.9 mg (begin)-255.2 mg (end)) and hypromellose capsules (size 2) (mean mass: 261.1 (begin)-257.8 mg (end)) respectively.
Capsules were stored at 40° C./75% RH in a closed glass vial. The amount of bendamustine hydrochloride and of related substances was measured with HPLC, as described above. The results are shown in Table 3b (filled in hypromellose capsules) and 3c (filled in gelatine capsules).

TABLE 3b

Bendamustine powder mixture in hypromellose capsules: Related substances and assay of bendamustine HCl (residual content)

| Storage condition | Related substances | T = 0 | T = 2 months | T = 0 | T = 2 months |
|---|---|---|---|---|---|
| | | | | Bendamustine HCl [% area] | |
| 40° C./75% RH (closed vials) | HP1 | 0.18 | 0.86 | 99.50 | 98.17 |
| | HP2 | n.d. | 0.25 | | |
| | HP3 | n.d. | 0.06 | | |
| | NP1 | n.d. | n.d. | | |
| | BM1Dimer | 0.08 | 0.10 | | |
| | BM1EE | 0.15 | 0.14 | | |
| | Unit RRT 0.68 | n.d. | <0.05 | | |
| | Unit RRT 0.70 | n.d. | 0.19 | | |

TABLE 3c

Bendamustine powder mixture in gelatin capsules: Related substances and assay of bendamustine HCl (residual content)

| Storage condition | Related substances | T = 0 | T = 2 months | T = 0 | T = 2 months |
|---|---|---|---|---|---|
| | | | | Bendamustine HCl [% area] | |
| 40° C./75% RH (closed vials) | HP1 | 0.23 | 1.35 | 99.38 | 97.74 |
| | HP2 | n.d. | 0.06 | | |
| | HP3 | n.d. | n.d. | | |
| | NP1 | n.d. | n.d. | | |
| | BM1Dimer | 0.13 | 0.10 | | |
| | BM1EE | 0.16 | 0.14 | | |
| | Unit RRT 0.68 | n.d. | 0.05 | | |
| | Unit RRT 0.70 | n.d. | 0.32 | | |

Reference Example 4

TABLE 4a

Bendamustine powder composition for capsules

| Component | mg/dosage-form | Relative Content % |
|---|---|---|
| Bendamustine hydrochloride | 55.1 | 22.04 |
| Lactose anhydrous | 145.15 | 58.06 |
| Microcrystalline cellulose (AVICEL PH112) | 31.25 | 12.50 |
| AC-DI-SOL | 12.5 | 5.00 |
| Colloidal silicon dioxide (AEROSIL 200) | 1.0 | 0.40 |
| Magnesium stearate | 2.5 | 1.00 |
| Ascorbic acid | 2.5 | 1.00 |
| Sum | 250 | 100.0 |

For 1000 capsules all excipients except for colloidal silicon dioxide and magnesium stearate were loaded into a Somakon vessel (2.5 L). Bendamustine was added and blending was conducted for 4 minutes at 1000 rpm (wiper 10 rpm). The resulting blend was sieved through a 0.5 mm sieve. The vessel was reloaded with the blend and colloidal silicon dioxide was added. Blending was conducted for 2 minutes at the afore-mentioned conditions.
Thereafter magnesium stearate was added and blending was continued for 1 minute. The blend was subsequently sieved through a 0.5 mm sieve, reloaded into the vessel and blended for another 30 seconds, all at the same conditions.
The blend was transferred to a capsule filling machine (Zanassi AZ 5) and filled into hard gelatine capsules (size 2)

(mean mass: 241.3 mg (begin)-244. mg (end)) and hypromellose capsules (size 2) (mean mass: 243.5 (begin)-243. mg (end)) respectively.

Capsules were stored at 40° C./75% RH in a closed glass vial. The amount of bendamustine hydrochloride and of related substances was measured with HPLC, as described above. The results are shown in Table 4b (filled into hypromellose capsules) and 4c (filled in gelatine capsules).

TABLE 4b

Bendamustine powder composition in hypromellose capsules: Related substances and assay of bendamustine HCl (residual content)

| Storage condition | Related substances | T = 0 | T = 2 months | T = 0 | T = 2 months |
|---|---|---|---|---|---|
| 40° C./75% RH (closed vials) | HP1 | 0.18 | 0.86 | 99.49 | 98.29 |
| | HP2 | n.d. | 0.25 | | |
| | HP3 | n.d. | 0.06 | | |
| | NP1 | n.d. | n.d. | | |
| | BM1Dimer | 0.08 | 0.10 | | |
| | BM1EE | 0.15 | 0.14 | | |
| | Unid RRT 0.57 | n.d. | 0.07 | | |
| | Unid RRT0.63 | n.d. | 0.05 | | |
| | Unid RRT 0.64 | n.d. | n.d. | | |
| | Unid RRT 0.68 | n.d. | n.d. | | |
| | Unid RRT 0.69 | n.d. | n.d. | | |
| | Unid RRT 0.70 | n.d. | 0.19 | | |
| | Unid RRT 0.75 | n.d. | 0.07 | | |
| | Unid RRT 0.77 | n.d. | 0.05 | | |
| | Unid RRT 0.93 | n.d. | 0.07 | | |

Column header: Bendamustine HCl [% area]

TABLE 4c

Bendamustine powder composition in gelatin capsules: Related substances and assay of bendamustine HCl (residual content)

| Storage condition | Related substances | T = 0 | T = 2 months | T = 0 | T = 2 months |
|---|---|---|---|---|---|
| 40° C./75% RH (closed vials) | HP1 | 0.29 | 1.10 | 99.26 | 96.38 |
| | HP2 | n.d. | 0.55 | | |
| | HP3 | n.d. | n.d. | | |
| | NP1 | n.d. | n.d. | | |
| | BM1Dimer | 0.12 | 0.17 | | |
| | BM1EE | 0.15 | 0.15 | | |
| | Unid RRT 0.58 | n.d. | 0.44 | | |
| | Unid RRT 0.62 | n.d. | 0.23 | | |
| | Unid RRT 0.65 | n.d. | 0.10 | | |
| | Unid RRT 0.68 | 0.07 | 0.07 | | |
| | Unid RRT 0.69 | n.d. | 0.06 | | |
| | Unid RRT 0.70 | 0.05 | 0.25 | | |
| | Unid RRT 0.76 | n.d. | 0.17 | | |
| | Unid RRT 0.77 | n.d. | 0.07 | | |
| | Unid RRT 0.77 | n.d. | 0.08 | | |
| | Unid RRT 0.78 | n.d. | 0.09 | | |
| | Unid RRT 0.79 | n.d. | 0.06 | | |
| | Unid RRT 0.91 | n.d. | n.d. | | |
| | Unid RRT 0.94 | n.d. | 0.06 | | |
| | Unid RRT 1.11 | n.d. | n.d. | | |
| | Unid RRT 1.18 | n.d. | n.d. | | |

Column header: Bendamustine HCl [% area]

Example 1

TABLE 5a

| Liquid filled hard capsule | | |
|---|---|---|
| Component | mg/dosage-form | Relative Content % |
| bendamustine hydrochloride | 55.1 | 9.18 |
| PLURONIC L44 NF | 450.70 | 75.12 |
| CREMOPHOR RH 40 | 81.85 | 13.64 |
| SOFTISAN 645 | — | — |
| Methyl paraben | 1.20 | 0.20 |
| Propyl paraben | 0.12 | 0.02 |
| Butyl hydroxytoluene | 0.12 | 0.02 |
| Ethanol | 10.91 | 1.82 |

0.68 g of methylparaben, 0.068 g of propylparaben and 0.068 g of butylhydroxytoluene were weighed and dissolved in 6.14 g of ethanol. CREMOPHOR RH 40 was melted at 40° C. in a sufficient amount. 5.56 g of the ethanolic solution obtained, 36.83 g of the melted CREMOPHOR RH 40 and 202.82 g of PLURONIC L44 NF were weighed and mixed at 800 rpm using a mechanical stirrer until the mixture became transparent. The mixture was allowed to solidify by placing it at 10° C. 24.80 g of bendamustine hydrochloride was subsequently added to the solidified blend by manual stirring and then distributed over the blend by homogenisation using an Ultraturrax T18 high speed homogeniser at 15500 rpm for 10 minutes. The homogenised suspension was filled into hard gelatine capsules with a CFS 1200 capsule filling and sealing machine, operated at 25° C. The capsules were closed and sealed. The liquid filled capsules were stored in closed amber glass bottles with screw plugs at 40° C./75% RH, at 30° C./65% RH, at 25° C./60% RH and at 5° C. The amount of bendamustine hydrochloride as well as of related substances, like degradation products, by-products of synthesis was measured with HPLC (column: Zorbax Bonus-RP, 5 μm; temperature of column oven: 30° C.; temperature of autosampler: 5° C.; detector: 254 nm). The results are shown in Table 5b.

TABLE 5b

Related substances and assay of bendamustine HCl (residual content)

| Storage condition | Related substances | T = 0 | T = 3 months | T = 0 | T = 3 months |
|---|---|---|---|---|---|
| 40° C./75% RH (closed vial) | HP1 | 0.09 | 0.07 | 98.8 | 98.5 |
| | NP1 | n.d. | n.d. | | |
| | BM1Dimer | 0.02 | 0.03 | | |
| | BM1EE | 0.15 | 0.15 | | |
| | Individual unknown impurity | 0.01 | 0.08 | | |
| 30° C./65% RH (closed vial) | HP1 | 0.09 | 0.06 | 98.8 | 98.9 |
| | NP1 | n.d. | n.d. | | |
| | BM1Dimer | 0.02 | 0.03 | | |
| | BM1EE | 0.15 | 0.15 | | |
| | Individual unknown impurity | 0.01 | 0.03 | | |
| 25° C./60% RH (closed vial) | HP1 | 0.09 | 0.07 | 98.8 | 99.0 |
| | NP1 | n.d. | n.d. | | |
| | BM1Dimer | 0.02 | 0.03 | | |
| | BM1EE | 0.15 | 0.15 | | |
| | Individual | 0.01 | 0.03 | | |

Column header: Bendamustine HCl [% area]

TABLE 5b-continued

Related substances and assay of bendamustine HCl
(residual content)

| Storage condition | Related substances | Bendamustine HCl [% area] | | | |
|---|---|---|---|---|---|
| | | T = 0 | T = 3 months | T = 0 | T = 3 months |
| 5° C. (closed vial) | HP1 | 0.09 | 0.07 | 98.8 | 99.8 |
| | NP1 | n.d. | n.d. | | |
| | BM1Dimer | 0.02 | 0.02 | | |
| | BM1EE | 0.15 | 0.15 | | |
| | Individual unknown impurity | 0.01 | n.d. | | |

Example 2

TABLE 6a

Liquid filled hard capsule

| Component | mg/dosage-form | Relative Content % |
|---|---|---|
| bendamustine hydrochloride | 55.1 | 9.18 |
| PLURONIC L44 NF | — | |
| CREMOPHOR RH 40 | 532.55 | 88.76 |
| SOFTISAN 645 | — | |
| Methyl paraben | 1.20 | 0.20 |
| Propyl paraben | 0.12 | 0.02 |
| Butyl hydroxytoluene | 0.12 | 0.02 |
| Ethanol | 10.91 | 1.82 |

0.68 g of methylparaben, 0.068 g of propylparaben and 0.068 g of butylhydroxytoluene were weighed and dissolved in 6.14 g of ethanol. CREMOPHOR RH 40 was melted at 40° C. in a sufficient amount. 5.56 g of the ethanolic solution obtained and 239.65 g of the melted CREMOPHOR RH 40 were weighed and mixed at 800 rpm using a mechanical stirrer until the mixture became transparent. The mixture was allowed to solidify and cool to room temperature. 24.80 g of bendamustine hydrochloride was subsequently added to the solidified blend by manual stirring and then distributed over the blend by homogenisation using an Ultraturrax T18 high speed homogeniser at 15500 rpm for 10 minutes. The homogenised suspension was filled into hard gelatine capsules with a CFS 1200 capsule filling and sealing machine, operated at 40° C. The capsules were closed and sealed.

The liquid filled capsules so obtained were stored in closed amber glass bottles with screw plugs at 40° C./75% RH, at 30° C./65% RH, at 25° C./60% RH and at 5° C. The amount of bendamustine hydrochloride as well as of related substances, like degradation products, by-products of synthesis was measured with HPLC, as described above.

The results are shown in Table 6b:

TABLE 6b

Related substances and assay of bendamustine HCl
(residual content)

| Storage condition | Related substances*[1] | Bendamustine HCl [% area] | | | |
|---|---|---|---|---|---|
| | | T = 0 | T = 3 months | T = 0 | T = 3 months |
| 40° C./75% RH (closed vial) | HP1 | 0.08 | 0.07 | 100.10 | 99.0 |
| | NP1 | 0.01 | 0.02 | | |
| | BM1Dimer | 0.03 | 0.09 | | |
| | BM1EE | 0.16 | 0.17 | | |
| | Individual unknown impurity | 0.02 | 0.09 | | |
| 30° C./65% RH (closed vial) | HP1 | 0.08 | 0.06 | 100.1 | 100.4 |
| | NP1 | 0.01 | n.d. | | |
| | BM1Dimer | 0.03 | 0.04 | | |
| | BM1EE | 0.16 | 0.13 | | |
| | Individual unknown impurity | 0.02 | 0.03 | | |
| 25° C./60% RH (closed vial) | HP1 | 0.08 | 0.10 | 100.1 | 100.3 |
| | NP1 | 0.01 | n.d. | | |
| | BM1Dimer | 0.03 | 0.03 | | |
| | BM1EE | 0.16 | 0.14 | | |
| | Individual unknown impurity | 0.02 | 0.02 | | |
| 5° C. (closed vial) | HP1 | 0.08 | 0.09 | 100.1 | 99.5 |
| | NP1 | 0.01 | 0.01 | | |
| | BM1Dimer | 0.03 | 0.03 | | |
| | BM1EE | 0.16 | 0.15 | | |
| | Individual unknown impurity | 0.02 | 0.02 | | |

Example 3

TABLE 7a

Liquid filled hard capsule

| Component | mg/dosage-form | Relative Content % |
|---|---|---|
| Bendamustine hydrochloride | 55.1 | 9.18 |
| PLURONIC L44 NF | — | |
| CREMOPHOR RH 40 | 81.85 | 13.64 |
| SOFTISAN 645 | 450.70 | 75.12 |
| Methyl paraben | 1.20 | 0.20 |
| Propyl paraben | 0.12 | 0.02 |
| Butyl hydroxytoluene | 0.12 | 0.02 |
| Ethanol | 10.91 | 1.82 |

0.68 g of methylparaben, 0.068 g of propylparaben and 0.068 g of butylhydroxytoluene were weighed and dissolved in 6.14 g of ethanol. CREMOPHOR RH 40 was melted at 40° C. in a sufficient amount. 5.56 g of the ethanolic solution obtained, 36.83 g of the melted CREMOPHOR RH 40 and 202.82 g of SOFTISAN 645 were weighed and mixed at 800 rpm using a mechanical stirrer until the mixture became transparent. The mixture was allowed to solidify by placing it at 10° C. 24.80 g of bendamustine hydrochloride was subsequently added to the solidified blend by manual stirring and then distributed over the blend by homogenisation using an Ultraturrax T18 high speed homogeniser at 15500 rpm for 10 minutes. The homogenised suspension was filled into hard gelatine capsules with a CFS 1200 capsule filling and sealing machine, operated at 30° C. The capsules were closed and sealed. The liquid filled capsules were stored in closed amber glass bottles with screw plugs at 40° C./75% RH, at 30° C./65% RH, at 25° C./60% RH and at 5° C. The amount of bendamustine hydrochloride as well as of related substances, like degradation products, by-products of synthesis was measured with HPLC, as described above. The results are shown in Table 7b:

TABLE 7b

Related substances and assay of bendamustine HCl (residual content)

| Storage condition | Related substances*[1] | T = 0*[2] | T = 3 months | Bendamustine HCl [% area] T = 0 | T = 3 months |
|---|---|---|---|---|---|
| 40° C./75% RH (closed vial) | HP1 | 0.08 | 0.06 | 99.6 | 99.5 |
| | NP1 | n.d. | 0.01 | | |
| | BM1Dimer | 0.03 | 0.36 | | |
| | BM1EE | 0.15 | 0.26 | | |
| | Individual unknown impurity | 0.03 | 0.13 | | |
| 30° C./65% RH (closed vial) | HP1 | 0.08 | 0.11 | 99.6 | 99.9 |
| | NP1 | n.d. | n.d. | | |
| | BM1Dimer | 0.03 | 0.09 | | |
| | BM1EE | 0.15 | 0.17 | | |
| | Individual unknown impurity | 0.03 | 0.04 | | |
| 25° C./60% RH (closed vial) | HP1 | 0.08 | 0.11 | 99.6 | 100.0 |
| | NP1 | n.d. | n.d. | | |
| | BM1Dimer | 0.03 | 0.09 | | |
| | BM1EE | 0.15 | 0.17 | | |
| | Individual unknown impurity | 0.03 | 0.04 | | |
| 5° C. (closed vial) | HP1 | 0.08 | 0.07 | 99.60 | 100.1 |
| | NP1 | n.d. | 0.01 | | |
| | BM1Dimer | 0.03 | 0.03 | | |
| | BM1EE | 0.15 | 0.15 | | |
| | Individual unknown impurity | 0.03 | 0.02 | | |

Example 4

LFHC-formulations were prepared based on an oily suspension suitable to obtain a physico-chemically stable formulation. Below the formulation development of liquid filled hard capsules (LFHC) together with the analytical evaluation of these products during formulation development and stability program is represented.

Tested features of the final LFHC included appearance, dissolution rate and physical and chemical stability, under different conditions, for at least 3 months.

Due to the strong incompatibility between water and the LiCaps capsule shell, the behavior of the bendamustine hydrochloride in a series of alternative oily vehicles suitable for filling hard gelatin capsules was evaluated. Most of the bendamustine hydrochloride added to this kind of oils was found to be suspended rather than dissolved. So, the excipients used in the formulation development were considered to be carriers for a bendamustine hydrochloride suspension. An analytical method to determine the amount of the bendamustine hydrochloride dissolved in each carrier, was also developed.

The carriers used were initially selected and characterised according to their physico-chemical compatibility with both, bendamustine hydrochloride and LiCaps and according to their ability to allow both a stable formulation and a fast dissolution.

To support the bendamustine hydrochloride in suspension, the need of a viscosity increaser was also considered for the carriers with a low viscosity at room temperature.

An evaluation of the effect of the carrier moisture content (both on bendamustine hydrochloride and capsule shell) was deemed necessary to assure the robustness of the formulation in different relative humidity conditions; to this aim, a water sorption/desorption analysis was performed to provide for each carrier a trend of their hygroscopicity, in order to predict the formulation behavior during the stability study.

The impact of the bendamustine hydrochloride concentration on the stability of the suspension was evaluated by manufacturing batches with an increased bendamustine hydrochloride/Carrier ratio.

A carrier with a low purity grade, such as a physically aged carrier, could affect the stability of the formulation: this aspect was investigated by using aged carriers in batch manufacturing. All the manufactured batches were placed for three months under ambient and accelerated stability conditions and evaluated for:

Assay
Purity
Appearance
Dissolution at pH 1.5

A study to determine the possible amount of bendamustine hydrochloride dissolved in each carrier was performed as well as a visual evaluation of the behavior of LFHC after dissolution. The moisture content of the carrier, as well as its hygroscopicity, could affect the physic-chemical stability of the formulation. A high water content could degrade bendamustine hydrochloride, due to its sensitivity, while a hygroscopic carrier could damage the capsule shell and increase its brittleness. Water sorption/desorption analysis was performed on the selected carriers in order to increase their moisture content and predict their behavior during the storage. Furthermore, the moisture content of two different carriers was artificially modified and these were used in batch manufacturing.

To assure a physically stable suspension, from the early phase of preparation to the stability, low viscosity carriers were used in batch manufacturing, in combination with the minimum suitable amount of a viscosity increaser to avoid, visually, sedimentation phenomena. Two different kinds of viscosity increaser were used: a silicon powder (AEROSIL) and a semisolid matrix with a melting point higher than 40° C. (GELUCIRE 44/14). The same carriers were also tested without the viscosity increaser and the resulting formulations compared with the above mentioned ones.

Two different bendamustine hydrochloride/Carrier ratios were evaluated for two different carriers in order to evaluate the behavior, in terms of physical stability and dissolution, of a suspension more concentrated in bendamustine hydrochloride than the formulation developed so far.

Two different carriers were submitted to an artificial treatment to accelerate a possible "aging" phenomenon and were used in batch manufacturing, in order to evaluate the effect on the stability of the formulation of a carrier with a low purity level.

The bendamustine hydrochloride dissolved in the vehicle may be exposed to chemical degradation more than the suspended one. In order to verify a possible degradation of the bendamustine hydrochloride during the stability, an analytical method to quantify the actual amount of bendamustine hydrochloride and related impurities solubilised by the oil, was developed.

A fast dissolution is one of the most important features of LFHC. Due to the poor miscibility with water of some of the oils used in capsule manufacturing, a visual appearance of the behavior of the suspension during the in vitro dissolution was found to be helpful to clarify different physical aspects of the manufactured suspensions and also to predict the correspondent in vivo behavior.

Experimental Part

TABLE 8

List of the equipment used for batch manufacturing and analytical controls

| Equipment | Manufacturer | Use |
|---|---|---|
| HPLC system equipped with a PDA detector and Empower software | Waters | Analytical controls on formulations |
| Weighing balance | Mettler-Toledo | In process and final capsules weight controls |
| UV/VIS spectrometer | Perkin-Elmer | Analytical controls on formulations |
| Differential scanning calorimetry (DSC) | Perkin-Elmer | Compatibility studies |
| Dissolution tester | Sotax/Erweka | Analytical controls on formulations |
| Propeller stirrer | Velp | Batch manufacturing |
| Electro-magnetic stirrer | Velp | Batch manufacturing |
| Oven | Memmert | Batch manufacturing |
| Climatic room 25° C./60% RH | — | Batch stability |
| Climatic chamber 40° C./75% RH | Angelantoni | Batch stability |
| Refrigerator 5° C. | Angelantoni | Batch stability |
| Ultraturrax high speed homogenizer | IKA | Batch manufacturing |
| Capsule Filling and Sealing Machine (CFS1200) | Capsugel | Batch manufacturing |

TABLE 9.a

Excipients used in batch manufacturing

| Non-proprietary name(*) | Proprietary name | Physical state at RT | Viscosity at RT (limits in mPa/s) | Function | HLB |
|---|---|---|---|---|---|
| Macrogol glycerol hydroxystearate | CREMOPHOR RH40 | Semisolid | Not applicable(¯) | Carrier | 14-16 |
| Propylene glycol dicaprylocaprate | LABRAFAC PG | Liquid | 9-12 | Carrier | |
| Propylene glycol laurate | LAUROGLYCOL FCC | Liquid | Not available | Carrier | |
| Propylene glycol caprylate | CAPRYOL PGMC | Liquid | Not available | Carrier | |
| Oleoyl Macrogolglycerides | LABRAFIL M1944 | Liquid | 75-95 | Carrier | |
| Propylene glycol monolaurate | LAUROGLYCOL 90 | Liquid | Not available | Carrier | |
| Linoleoyl Macrogolglycerides | LABRAFIL M2125 | Liquid | 70-90 | Carrier | |
| Polyglyceryl oleate | PLUROL oléique CC497 | Liquid | Not available | Carrier | 6 |
| Caprylic/Capric Triglyceride | MIGLYOL 810 | Liquid | 27-33 | Carrier | |
| Caprylic/Capric/Succinic Triglyceride | MIGLYOL 829 | Liquid | 230-270 | Carrier | |
| Propylene Glycol Dicarylate/Dicaprate | MIGLYOL 840 | Liquid | 9-12 | Carrier | |
| Caprylic/Capric Triglyceride | MIGLYOL 812 | Liquid | 27-33 | Carrier | |
| Bis-Diglyceryl Polyacyladipate-1 | SOFTISAN 645 | Liquid | Not available | Carrier | |
| Bis-Diglyceryl Polyacyladipate-2 | SOFTISAN 649 | Semisolid | Not applicable | Carrier | |
| Poloxamer 124 | PLURONIC L44 NF | Liquid | 440(**) | Carrier | 15 (12-18) |
| Poloxamer 188 | LUTROL F68 | Solid | Not applicable | Carrier | >24 |
| Poloxamer 407 | LUTROL F127 | Solid | Not applicable | Carrier | >24 |
| Polyoxyl 35 Castor Oil | CREMOPHOR EL | Liquid | 700-850 | Carrier | 12-14 |
| Diethylen glycol mono ethyl ether | TRANSCUTOL HP | Liquid | Not available | Carrier | |
| Macrogol (6) Cetostearyl ether | CREMOPHOR A6 | Semisolid | Not applicable | Carrier | 10-12 |
| Macrogol (25) Cetostearyl ether | CREMOPHOR A25 | Semisolid | Not applicable | Carrier | 15-17 |
| Diethylen glycol mono butyl ether | — | Liquid | Not available | Carrier | |
| Diethylen glycol mono methyl ether | — | Liquid | Not available | Carrier | |
| Glyceryl Ricinoleate | SOFTIGEN 701 | Semisolid | Not applicable(⁺) | Carrier | |
| Colloidal Silicon dioxide | AEROSIL | Powder | Not applicable | Viscosity increaser | |
| Lauroyl Macrogolglycerides | GELUCIRE 44/14 | Semisolid | Not applicable | Viscosity increaser | |

(*)May not correspond to the compendial status name
(**)Determined with Hoeppler method on product "as is"
(¯)Viscosity of aqueous solution determined with Hoeppler method: 20-40 mPa/s
(⁺)Available viscosity value at 30-35 C.: 500-600 mPa/s TABLE 9.b Further excipients used in batch manufacturing

| Carrier | Non proprietary name | Physical state at RT | Melting point (range) ° C. | HLB* |
|---|---|---|---|---|
| BRIJ L23 | Macrogol 23 Lauryl ether | solid | 35-40 | 16.9 |
| BRIJ O20-SO | Macrogol 20 Oleyl ether | Semi solid | 48-50 | 15.5 |
| BRIJ O10-SS | Macrogol 10 Oleyl ether | Semi solid | 30-34 | 12.4 |
| BRIJ S10 | Macrogol 10 Stearyl ether | solid | 35-40 | 12.4 |
| BRIJ S20 | Macrogol 20 Stearyl ether | solid | 38-40 | 15.3 |
| BRIJ L4 | Macrogol 4 Lauryl ether | Liquid |  | 9.7 |
| BRIJ C2 | Macrogol 2 Cethyl ether | Semi solid | 36-42 | 5.3 |
| BRIJ S721-SO | Macrogol Stearyl ether 21 | solid | 46-51 | 15.5 |
| TWEEN 20 | Polysorbate 20 | Liquid |  | 16.7 |
| TWEEN 40 | Polysorbate 40 | Liquid |  | 15.6 |
| TWEEN 65 | Polysorbate 65 | Semi solid | 40-43 | 10.5 |
| TWEEN 61 | Polysorbate 61 | Semi solid | 45-50 | 9.6 |
| TWEEN 81 | Polysorbate 81 | Liquid |  | 10.0 |
| MIRJ S8-SS | Macrogol 8 Stearate | Semi solid | 38-41 | 11.1 |
| MYRJ S40 | PEG 40 Propylene Glycol Stearate | solid | 40-45 | 16.0 |
| MIRJ S100 | PEG 100 Stearate | Semi solid | 54-60 | 18.8 |
| GLYCEROX HE | Macrogol Glycerol Cocoates | Liquid |  | 10.6 |
| SOLUTOL HS 15 | Macrogol 15 Hydroxy Stearate | Semi solid | 30 | 14-16 |
| PLURONIC F108 | Poloxamer 338 | solid | 65-70 | 27 |
| PLURONIC L35 | Poloxamer 105 | Liquid |  | 19 |
| PLURONIC P85 | Poloxamer 235 | Semi solid | 45-50 | 16 |
| PLURONIC L64 | Poloxamer 184 | Liquid |  | 15 |
| PLURONIC P105 | Poloxamer 335 | Semi solid | 45-50 | 15 |
| PLURONIC L43 | Poloxamer 123 | Liquid |  | 12 |
| PLURONIC P103 | Poloxamer 333 | Semi solid | 45-50 | 9 |
| SPEZIOL TPGS | Tocoferol PEG 1000 | Semi solid | 37-41 | 13.2 |
| GELUCIRE 44/14 | Lauroyl Macrogol Glycerydes | Semi solid | 44 | 14 |

*data from literature

Manufacturing of Batches

Different categories of suspensions were manufactured and subsequently filled into size 0 LICAPS capsules.

Low and Medium Viscosity Carriers with Viscosity Increasers

In order to evaluate the effect of a viscosity modifier on the stability of the formulation, a series of active batches were manufactured according to the following formulation:
Bendamustine hydrochloride
Low viscosity carrier
AEROSIL or GELUCIRE 44/14 (viscosity increaser)

Different trials were performed to find a method to determine the suitable amount of viscosity increaser to be added in the formulation. According to the method developed, the amount of viscosity increaser added to the suspension was estimated as the minimum suitable amount to obtain a liquid formulation viscous enough to keep the bendamustine hydrochloride in suspension and to avoid its sedimentation. The amount of viscosity increaser to be added was found to be strongly related to the initial viscosity of the carrier.

The bendamustine hydrochloride:Carrier ratio in all the developed formulations was the same (about 1:10).

Low and Medium Viscosity Carriers without Viscosity Increasers

In order to evaluate the impact of bendamustine hydrochloride sedimentation and, indirectly the effect of the viscosity modifiers, different LFHC active batches were manufactured by employing low viscosity carriers according to the following formulation:
Bendamustine hydrochloride
Low viscosity carrier The bendamustine hydrochloride:Carrier ratio in all the developed formulations was the same (about 1:10).

High Viscosity Carriers

In order to evaluate the effect of temperature on the chemical stability of the bendamustine hydrochloride in the formulation, different semisolid carriers with a melting point above 30° C. were used in LFHC active batch manufacturing.

The suspensions were manufactured according to the following standard formulation for evaluation:
Bendamustine hydrochloride
High viscosity carrier The bendamustine hydrochloride:Carrier ratio in all the developed formulations was the same (about 1:10).

Bendamustine Hydrochloride/Carrier Ratio

Two different bendamustine hydrochloride/Carrier ratios were investigated with two different kinds of carriers, in order to evaluate the effect of the bendamustine hydrochloride concentration in the suspension on the final product stability.

The selection of the carriers was performed among both categories of carriers, low and high viscosity, in order to obtain representative data about two kind of suspensions. The formulations with low viscosity carrier included a viscosity modifier, to ensure the physical stability of the suspension.

The suspensions were manufactured according to the following standard formulation for evaluation:
Bendamustine hydrochloride
Carrier Carrier Purity: "Aging" Process Two different carriers were placed in open transparent glass bottles and exposed for about 5 days to:
Artificial light
Atmospheric oxygen
Compressed air flow on their surface The carriers were used in batch manufacturing according to the following formulation:
Bendamustine hydrochloride
Aged carrier The bendamustine hydrochloride:Carrier ratio in all the developed formulations was the same (about 1:10).

Carrier with Modified Moisture Content

In order to evaluate the effect of water uptake of the carrier on the stability of the bendamustine hydrochloride, the carriers were chosen among the more hygroscopic ones. Two carriers were dispensed in open glass beakers and placed in the following conditions:
25° C./75% RH
25° C./100% RH in order to obtain two different moisture levels per carrier.

The carriers with the moisture content modified as described above, were used in batch manufacturing according to the following formulation:
  Bendamustine hydrochloride
  Carriers with modified moisture content
  The bendamustine hydrochloride:Carrier ratio in all the developed formulations was the same (about 1:10).
Bendamustine Hydrochloride Solubility in Carriers Due to the necessity to determine if part of the bendamustine hydrochloride added to the vehicle is dissolved, in order to verify a possible degradation, an analytical procedure, from sample preparation to its analysis, was developed.
Sample Preparation for Liquid Oils Essentially, it consisted in the preparation of a supersaturated solution of bendamustine hydrochloride in the oil: the minimum amount of bendamustine hydrochloride suitable to generate sedimentation of solid particle on the bottom of the vessel was added to the oil warmed at 40° C.; this solution was electromagnetically stirred for several days (about 4) at room temperature and then centrifuged at 3000 rpm for 15 minutes. The supernatant was analysed by HPLC versus a solution of bendamustine hydrochloride working standard (0,551 mg/ml).
Sample Preparation for Semisolid Vehicles Essentially, it consisted in the preparation of a supersaturated solution of bendamustine hydrochloride in the vehicle: the minimum amount of bendamustine hydrochloride suitable to generate sedimentation of solid particle on the bottom of the vessel was added to the oil heated to about 5° C. above its melting point; this solution was kept in static condition at this temperature overnight, to allow sedimentation on the bottom. The supernatant was analysed by HPLC versus a solution of API working standard (0.551 mg/ml).
Visual Appearance During Dissolution Test A series of pictures of the dissolution vessel and of the basket was taken at the end of the dissolution test of the capsules analysed. Besides the pictures, a brief visual description of the appearance of the solution in the vessel was reported.
Stability Studies All manufactured batches were placed in stability, in amber glass bottles at the following storage conditions (Table 10).

Results and Discussion
Batches Manufactured with Low and Medium Viscosity Carriers and Viscosity Increaser
Vehicle Manufacturing Different trials were conducted in order to explore the minimum amount of viscosity increaser to add to the low viscosity oily excipients to obtain a vehicle suitable, after visual evaluation, for a physically stable suspension.

In this first phase, all the liquid excipients reported in table 9 were used, except SOFTISAN 645.

Vehicles obtained with AEROSIL, as viscosity increaser, were manufactured by homogenizing a coarse suspension of the powder in the oil, to obtain a colloidal dispersion. Most of the so-obtained vehicles were thixotropic materials (see table 11) able to change their viscosity depending more on the shear stress applied rather than on temperature variation. This behavior could avoid temperature stress on the bendamustine hydrochloride during the capsule filling step.

Vehicles obtained with GELUCIRE 44/14, as viscosity increaser, were manufactured by homogenising a mixture of the components, to obtain a transparent liquid that solidified at room temperature. So-obtained vehicles were semisolid or solid matrices, (depending on the viscosity increaser concentration) able to change their viscosity depending on temperature variations. All vehicles manufactured are reported in table 11.

A visual evaluation was carried out on all the samples prepared in order to perform a screening among them, based upon their viscosity, and to predict their behavior in suspension with the bendamustine hydrochloride. According to the evaluation performed, only thixotropic and semisolid samples were considered to be suitable and were used in the subsequent step of placebo suspension manufacturing.

TABLE 11

Vehicles manufactured with low/medium viscosity carriers and viscosity increasers

| Batch No | Carrier | Viscosity increaser | Amount of viscosity increaser (%) | Physical characteristic at room |
|---|---|---|---|---|
| D001L/011 | LABRAFAC PG | AEROSIL | 6.5 | Thixotropic |
| D001L/022 | MIGLYOL 829 | AEROSIL | 6.8 | Thixotropic |
| D001L/033 | MIGLYOL 810 | AEROSIL | 7.1 | Thixotropic |
| D001L/044 | PLUROL Oléique | AEROSIL | 2.9 | Medium |
| D001L/055 | MIGLYOL 840 | AEROSIL | 6.3 | Thixotropic |
| D001L/066 | CREMOPHOR | AEROSIL | 2.5 | Medium |
| D001L/077 | TRANSCUTOL | AEROSIL | 6.4 | Low viscosity |
| D001L/088 | TRANSCUTOL | AEROSIL | 7.5 | Low viscosity |

TABLE 10

Stability study program

| | | 25° C./60% RH | | | 40° C./75% RH | | |
|---|---|---|---|---|---|---|---|
| | Time = 0 | 1 month | 2 months | 3 months | 1 month | 2 months | 3 months |
| Appearance | X | | X | X | X | X | X |
| Assay | X | | X | X | X | X | X |
| Impurity | X | | X | X | X | X | X |
| Content Uniformity | X | | | | | | |
| Dissolution (pH 1.5) after 10, 20, 30 min | X | | X | X | X | X | X |

TABLE 11-continued

Vehicles manufactured with low/medium viscosity carriers and viscosity increasers

| Batch No | Carrier | Viscosity increaser | Amount of viscosity increaser (%) | Physical characteristic at room |
|---|---|---|---|---|
| D001L/099 | LAUROGLYCOL | AEROSIL | 6.7 | Low viscosity |
| D001L/10 | PLURONIC L44 | AEROSIL | 4.3 | Medium |
| D001L/111 | LABRAFIL M | AEROSIL | 5.8 | Thixotropic |
| D001L/122 | LAUROGLYCOL | AEROSIL | 7.2 | Thixotropic |
| D001L/13 | LABRAFIL | AEROSIL | 4.8 | Thixotropic |
| D001L/14 | PLUROL Oléique | AEROSIL | 3.8 | Medium |
| D001L/15 | PLURONIC L44 | AEROSIL | 5.9 | Medium |
| D001L/16 | LAUROGLYCOL | AEROSIL | 7.6 | High viscosity |
| D001L/17 | TRANSCUTOL HP | AEROSIL + GELUCIRE 44/14 | 2.4 + 51.9 | Low viscosity liquid |
| D001L/18 | LAUROGLYCOL | AEROSIL | 7.1 | High viscosity |
| D001L/19 | MIGLYOL 812 | AEROSIL | 5.4 | Thixotropic |
| D001L/20 | PLURONIC L44 | AEROSIL | 7.4 | Medium |
| D001L/21 | CREMOPHOR | GELUCIRE 44/14 | 49.9 | High viscosity |
| D001L/22 | LAUROGLYCOL | GELUCIRE 44/14 | 50.8 | Semisolid |
| D001L/23 | CREMOPHOR | GELUCIRE 44/14 | 26.1 | High viscosity |

Preparations of Batches Containing Bendamustine Hydrochloride

Eight vehicles were further investigated and used in the preparation of LFHC formulations containing bendamustine hydrochloride. The composition of all batches manufactured—with the corresponding analytical results at time zero—are reported in table 12a, b and c.

The batches were intended to be made by adding the viscosity increaser (AEROSIL) to the carrier, and subsequently homogenising the mixture thus obtained. Thereafter the bendamustine hydrochloride was added, followed by homogenisation. The mixture obtained was filled into LICAPS capsules. Only for one batch (D001L/035) this manufacturing method was used: the second homogenisation step, after adding the bendamustine, resulted in a massive increase in the viscosity of the suspension, and therefore caused problems during the subsequent filling step. The suspension was for this reason hand-filled in gelatin capsules, sealed by Capsule Filling and Sealing machine CFS 1200.

The manufacturing method for the batches was therefore optimised, which resulted in the following manufacturing method: The batches were made by adding the viscosity increaser (AEROSIL) to the carrier. Thereafter the bendamustine hydrochloride was added, followed by homogenisation. The mixture obtained was filled into LICAPS capsules.

TABLE 12a

Batches containing bendamustine and low and medium viscosity carriers and viscosity modifiers

| Components | D001L/035 % | D001L/036 % | D001L/037 % | D001L/038 % | D001L/039 % | D001L/040 % | D001L/041 % | D001L/042 % | D001L/043 % | D001L/044 % | D001L/045 % |
|---|---|---|---|---|---|---|---|---|---|---|---|
| LABRAFAC PG | 85.1 | 84.4 | 86.7 | 89.5 | — | — | — | — | — | — | — |
| MIGLYOL 840 | — | — | — | — | 86.5 | — | — | — | — | — | — |
| MIGLYOL 829 | — | — | — | — | — | 85.8 | — | — | — | — | — |
| MIGLYOL 812 | — | — | — | — | — | — | 86.9 | — | — | — | — |
| MIGLYOL 810 | — | — | — | — | — | — | — | 87.0 | — | — | — |
| PLUROL oleique CC497 | — | — | — | — | — | — | — | — | 89.2 | — | — |
| LAUROGLYCOL FCC | — | — | — | — | — | — | — | — | — | 85.2 | — |
| PLURONIC L44 NF INH | — | — | — | — | — | — | — | — | — | — | 88.2 |
| LABRAFIL M1944 CS | — | — | — | — | — | — | — | — | — | — | — |
| LABRAFIL M2125 | — | — | — | — | — | — | — | — | — | — | — |
| LAUROGLYCOL 90 | — | — | — | — | — | — | — | — | — | — | — |
| CREMOPHOR EL | — | — | — | — | — | — | — | — | — | — | — |
| TRANSCUTOL HP | — | — | — | — | — | — | — | — | — | — | — |
| Bendamustine HCl | 9.2 | 9.4 | 9.7 | 9.4 | 9.6 | 9.6 | 9.7 | 9.7 | 10.0 | 9.5 | 9.8 |
| Aerosil | 5.7 | 6.2 | 3.6 | 1.1 | 3.9 | 4.6 | 3.4 | 3.3 | 0.8 | 5.3 | 2.0 |
| GELUCIRE 44/14 | — | — | — | — | — | — | — | — | — | — | — |

| Components | D001L/046 % | D001L/047 % | D001L/048 % | D001L/049 % | D001L/050 % | D001L/051 % | D001L/052 % | D001L/053 % | D001L/085 % | D001L/086 % |
|---|---|---|---|---|---|---|---|---|---|---|
| LABRAFAC PG | — | — | — | — | — | — | — | 45.2 | — | — |
| MIGLYOL 840 | — | — | — | — | — | — | — | — | — | — |

TABLE 12a-continued

Batches containing bendamustine and low and medium viscosity carriers and viscosity modifiers

| | | | | | | | | | | |
|---|---|---|---|---|---|---|---|---|---|---|
| MIGLYOL 829 | — | — | — | — | — | — | — | — | — | — |
| MIGLYOL 812 | — | — | — | — | — | — | — | — | — | — |
| MIGLYOL 810 | — | — | — | — | — | — | — | — | — | — |
| PLUROL oleique CC497 | — | — | — | — | — | — | — | — | — | — |
| LAUROGLYCOL FCC | — | — | — | — | — | — | — | — | — | — |
| PLURONIC L44 NF INH | — | — | — | — | — | — | — | — | 45.4 | — |
| LABRAFIL M1944 CS | 87.0 | — | — | — | — | — | — | — | — | — |
| LABRAFIL M2125 | — | 86.9 | — | — | — | — | — | — | — | — |
| LAUROGLYCOL 90 | — | — | 85.4 | — | 44.6 | — | — | — | — | — |
| CREMOPHOR EL | — | — | — | 88.4 | — | 80.7 | — | — | — | — |
| TRANSCUTOL HP | — | — | — | — | — | — | 82.4 | — | — | 45.4 |
| Bendamustine HCl | 9.7 | 9.7 | 9.5 | 9.9 | 9.3 | 9.3 | 9.2 | 9.3 | 9.2 | 9.2 |
| AEROSIL | 3.3 | 3.4 | 5.1 | 1.7 | — | — | 8.4 | — | — | — |
| GELUCIRE 44/14 | — | — | — | — | 46.1 | 10.0 | — | 45.5 | 45.4 | 45.4 |

TABLE 12b

Analytical results for batches containing bendamustine and low and medium viscosity carriers and viscosity modifiers (batches D001L/035 to D001L/044)

| | | Results of analytical Tests performed on LFHC | | | | | | | | |
|---|---|---|---|---|---|---|---|---|---|---|
| Analytical Test | Limits | D001L/ 035 | D001L/ 037 | D001L/ 038 | D001L/ 039 | D001L/ 040 | D001L/ 041 | D001L/ 042 | D001L/ 043 | D001L/ 044 |
| Identification (HPLC) | Positive | Positive | Positive | Positive | Positive | Positive | Positive | Positive | Positive | Positive |
| Assay (HPLC) | 95.0%–105.0% | | 108.4 | 87.4 | 105.0 | 83.8 | 103.9 | 102.4 | 96.0 | 99.8 |
| Related substances (HPLC) | | | | | | | | | | |
| HP1 | ≤0.50% | | 0.11 | 0.22 | 0.08 | 0.06 | 0.22 | 0.24 | 0.16 | 0.26 |
| BM1 Dimer | ≤0.20% | | 0.05 | 0.06 | 0.12 | 0.08 | 0.05 | 0.04 | 0.05 | 0.07 |
| BM1EE | ≤0.50% | | 0.16 | 0.15 | 0.16 | 0.10 | 0.15 | 0.15 | 0.15 | 0.14 |
| NP1 | ≤0.20% | | 0.01 | 0.01 | 0.01 | 0.01 | 0.01 | 0.01 | 0.01 | 0.01 |
| Ind. Unknown impurity | ≤0.10% | | 0.03 | 0.05 | 0.09 | 0.06 | 0.02 | 0.03 | 0.04 | 0.05 |
| Total impurities | ≤1.50% | | 0.36 | 0.49* | 0.46 | 0.31 | 0.47 | 0.49 | 0.41* | 0.55 |
| Dissolution Test (Medium: buffer pH = 1.5) | | | | | | | | | | |
| (% 10 min) | 80% in 30 min | 51.9 | 4.5 | 16.6 | 17.2 | 5.1 | 20.1 | 8.9 | 12.5 | 3.9 |
| (% 20 min) | | 68.4 | 15.7 | 34.3 | 33.7 | 8.9 | 32.3 | 17.7 | 14.5 | 4.9 |
| (% 30 min) | | 76.4 | 33.9 | 50.2 | 42.9 | 11.4 | 39.9 | 23.6 | 14.5 | 7.0 |

*Values calculated vs API area

TABLE 12c

Analytical results for batches containing bendamustine and low and medium viscosity carriers and viscosity modifiers (batches D001L/045 to D001L/053 and batches D001L/085 and D001L/086)

| | | Results of analytical Tests performed on LFHC | | | | | | | | | |
|---|---|---|---|---|---|---|---|---|---|---|---|
| Analytical Test | Limits | D001L/ 045 | D001L/ 046 | D001L/ 047 | D001L/ 048 | D001L/ 049 | D001L/ 050 | D001L/ 051 | D001L/ 052 | D001L/ 053 | D001L/ 085 | D001L/ 086 |
| Identification (HPLC) | Positive | Positive | Positive | Positive | Positive | Positive | Positive | Positive | Positive | Positive | Positive | Positive |
| Content uniformity | Complies | N/A | N/A | N/A | N/A | N/A | N/A | N/A | N/A | N/A | Complies (RSD 4.40) | Not Complies (RSD 5.55) |
| Assay (HPLC) | 95.0%–105.0% | 98.2 | 101.5 | 103.5 | 101.0 | 101.0 | 105.0 | 117.9 | 99.0 | 102.5 | 95.8 | 92.9 |
| Related substances (HPLC) | | | | | | | | | | | | |
| HP1 | ≤0.50% | 0.30 | 0.16 | 0.23 | 0.28 | 0.30 | 0.08 | 0.11 | 0.16 | 0.13 | 0.07 | 0.09 |
| BM1 Dimer | ≤0.20% | 0.05 | 0.05 | 0.05 | 0.05 | 0.04 | 0.04 | 0.04 | 0.04 | 0.04 | 0.04 | 0.04 |
| BM1EE | ≤0.50% | 0.14 | 0.15 | 0.15 | 0.13 | 0.15 | 0.13 | 0.15 | 0.16 | 0.15 | 0.14 | 0.15 |

TABLE 12c-continued

Analytical results for batches containing bendamustine and low and medium viscosity carriers and viscosity modifiers
(batches D001L/045 to D001L/053 and batches D001L/085 and D001L/086)

| | | Results of analytical Tests performed on LFHC | | | | | | | | | | |
|---|---|---|---|---|---|---|---|---|---|---|---|---|
| Analytical Test | Limits | D001L/ 045 | D001L/ 046 | D001L/ 047 | D001L/ 048 | D001L/ 049 | D001L/ 050 | D001L/ 051 | D001L/ 052 | D001L/ 053 | D001L/ 085 | D001L/ 086 |
| NP1 | ≤0.20% | 0.01 | 0.01 | 0.01 | 0.01 | 0.01 | 0.01 | 0.01 | 0.01 | n.d. | 0.01 | 0.01 |
| Ind. Unknown impurity | ≤0.10% | 0.04 | 0.02 | 0.03 | 0.04 | 0.14 | 0.02 | 0.04 | 0.03 | 0.02 | 0.01 | 0.13 |
| Total impurities | ≤1.50% | 0.54 | 0.40 | 0.49 | 0.53 | 0.68* | 0.27 | 0.35 | 0.40* | 0.33 | 0.27 | 0.42 |
| Dissolution Test (Medium: buffer pH = 1.5) | | | | | | | | | | | | |
| (% 10 min) | 80% in 30 min | 96.9 | 0.1 | 5.2 | 8.8 | 25.6 | 25.2 | 67.3 | 91.0 | 14.1 | 65.3 | 101.6 |
| (% 20 min) | | 97.1 | 1.1 | 6.7 | 13.3 | 46.5 | 48.0 | 96.2 | 90.0 | 37.2 | 102.5 | 102.3 |
| (% 30 min) | | 96.7 | 1.7 | 7.7 | 15.4 | 72.4 | 62.7 | 104.5 | 87.9 | 63.0 | 109.5 | 99.8 |

*Values calculated vs API area

According to the afore-mentioned manufacturing method, only one batch (D001L/036) was prepared: a massive increase in the suspension viscosity was again observed after the addition of bendamustine hydrochloride to the carrier, before the homogenisation. Because of that, homogenisation was not performed. Probably, some physical interaction between bendamustine hydrochloride and AEROSIL occurred during the process. This suspension was not filled in capsules.

The manufacturing process was further optimized as follows: bendamustine was added to the carrier and the mixture thus obtained was homogenized. Thereafter the viscosity increaser (AEROSIL) was added, under stirring, in the minimum amount suitable to obtain a viscous liquid suspension. In this way batches D001L/037 to D001L/049 and batch D0011/052 were prepared. Except for batch D001L/038 and D001L/052 (suspensions with low viscosity), all other suspensions were liquids having a high viscosity which were hand-filled in gelatin LiCaps. The minimum amount of AEROSIL added depended on the initial viscosity of the carrier.

The proposed manufacturing method for batches in which GELUCIRE 44/14 was used as a viscosity increaser, comprised the steps of adding the viscosity increasing agent to the carrier and homogenizing the mixture thus obtained. Thereafter bendamustine was added and the so obtained mixture was again homogenized prior to filling it in the LICAPS capsules. According to this manufacturing method batches No. D001L/049, 050, 053, 085 and 086 were prepared. All suspensions were semisolid matrices at room temperature which upon increase of the temperature showed a decrease of their viscosity. All manufactured suspensions were hand-filled in gelatin Licaps, except for batches D001L/085 and D001L/086, dosed by CFS1200.

The amount of GELUCIRE 44/14 employed in the manufacturing was determined in order to obtain a semisolid vehicle at room temperature but liquid at about 35° C., depending on the initial viscosity of the carrier.

All batches filled in LiCaps were analysed for:
Content of bendamustine
Impurities and
dissolution profile of bendamustine at pH 1.5

Due to the large weight variations found after hand-filling of the capsules, the content uniformity test was not carried out except for D001L/085 and 086.

Batches Manufactured with Low and Medium Viscosity Carriers without Viscosity Increaser Further, carriers having a low viscosity were used in the preparation of bendamustine containing suspensions according to the following manufacturing method: bendamustine was added to the carrier, without any viscosity increasing agent, the mixture was homogenized and thereafter filled in LiCaps. Several LFHC formulations were manufactured by using this type of carrier. Thanks to their low viscosity all suspensions could be filled into the LiCaps with the Capsule Filling and Sealing machine CFS 1200. The composition of all batches made with the corresponding analytical results at time zero are reported in tables 13a, b and c.

Sedimentation was observed for all formulations: the impact thereof on the physico-chemical stability of the final product was evaluated by performing the analytical tests reported before, during and after the stability testing. During the stability testing period, from time to time the capsules were turned upside down to prevent caking.

TABLE 13a.1

Batches containing bendamustine hydrochloride with low and medium
viscosity carriers without viscosity modifiers

| | Batch No | | | | | | | |
|---|---|---|---|---|---|---|---|---|
| Components | D001L/ 057 % | D001L/ 058 % | D001L/ 059 % | D001L/ 060 % | D001L/ 061 % | D001L/ 062 % | D001L/ 063 % | D001L/ 064 % |
| MIGLYOL 812 | 90.8 | — | — | — | — | — | — | — |
| MIGLYOL 810 | — | 90.8 | — | — | — | — | — | — |
| MIGLYOL 840 | — | — | 90.8 | — | — | — | — | — |
| MIGLYOL 829 | — | — | — | 90.8 | — | — | — | — |
| LABRAFAC PG | — | — | — | — | 90.8 | — | — | — |

TABLE 13a.1-continued

Batches containing bendamustine hydrochloride with low and medium viscosity carriers without viscosity modifiers

| Component | | | | | | | | |
|---|---|---|---|---|---|---|---|---|
| PLUROL oleique CC497 | — | — | — | — | — | 90.8 | — | — |
| CREMOPHOR EL | — | — | — | — | — | — | 90.8 | — |
| TRANSCUTOL HP | — | — | — | — | — | — | — | 90.8 |
| LAUROGLYCOL 90 | — | — | — | — | — | — | — | — |
| LABRAFIL M2125 | — | — | — | — | — | — | — | — |
| LAUROGLYCOL FCC | — | — | — | — | — | — | — | — |
| LABRAFIL M1944 CS | — | — | — | — | — | — | — | — |
| PLURONIC L44 INH NF | — | — | — | — | — | — | — | — |
| Diethylen glycol mono butyl ether | — | — | — | — | — | — | — | — |
| Capryol PGMC | — | — | — | — | — | — | — | — |
| Diethylen glycol mono methyl ether | — | — | — | — | — | — | — | — |
| Bendamustine HCl | 9.2 | 9.2 | 9.2 | 9.2 | 9.2 | 9.2 | 9.2 | 9.2 |

| Components | Batch No | | | | | | | |
|---|---|---|---|---|---|---|---|---|
| | D001L/ 065 % | D001L/ 066 % | D001L/ 067 % | D001L/ 068 % | D001L/ 078 % | D001L/ 088 % | D001L/ 089 % | D001L/ 092 % |
| MIGLYOL 812 | — | — | — | — | — | — | — | — |
| MIGLYOL 810 | — | — | — | — | — | — | — | — |
| MIGLYOL 840 | — | — | — | — | — | — | — | — |
| MIGLYOL 829 | — | — | — | — | — | — | — | — |
| LABRAFAC PG | — | — | — | — | — | — | — | — |
| PLUROL oleique CC497 | — | — | — | — | — | — | — | — |
| CREMOPHOR EL | — | — | — | — | — | — | — | — |
| TRANSCUTOL HP | — | — | — | — | — | — | — | — |
| LAUROGLYCOL 90 | 90.8 | — | — | — | — | — | — | — |
| LABRAFIL M2125 | — | 90.8 | — | — | — | — | — | — |
| LAUROGLYCOL FCC | — | — | 90.8 | — | — | — | — | — |
| LABRAFIL M1944 CS | — | — | — | 90.8 | — | — | — | — |
| PLURONIC L44 INH NF | — | — | — | — | 90.8 | — | — | — |
| Diethylen glycol mono butyl ether | — | — | — | — | — | 90.8 | — | — |
| Capryol PGMC | — | — | — | — | — | — | 90.8 | — |
| Diethylen glycol mono methyl ether | — | — | — | — | — | — | — | 90.8 |
| Bendamustine HCl | 9.2 | 9.2 | 9.2 | 9.2 | 9.2 | 9.2 | 9.2 | 9.2 |

TABLE 13a.2

Batches containing bendamustine hydrochloride with liquid carriers without viscosity modifiers

| Components | Batch No | | | | | | | |
|---|---|---|---|---|---|---|---|---|
| | D001L/ 093 % | D001L/ 094 % | D001L/ 095 % | D001L/ 097 % | D001L/ 098 % | D001L/ 099 % | D001L/ 100 % | D001L/ 119 % |
| TWEEN 20 | 90.8 | — | — | — | — | — | — | — |
| TWEEN 81 | — | 90.8 | — | — | — | — | — | — |
| GLYCEROX HE | — | — | 90.8 | — | — | — | — | — |
| PLURONIC L35 | — | — | — | 90.8 | — | — | — | — |
| BRIJ L4 | — | — | — | — | 90.8 | — | — | — |
| PLURONIC L64 | — | — | — | — | — | 90.8 | — | — |
| PLURONIC L43 | — | — | — | — | — | — | 90.8 | — |
| TWEEN 40 | — | — | — | — | — | — | — | 90.8 |
| Bendamustine HCl | 9.2 | 9.2 | 9.2 | 9.2 | 9.2 | 9.2 | 9.2 | 9.2 |

TABLE 13b.1

Analytical results for batches containing bendamustine hydrochloride with low and medium viscosity carriers without viscosity modifiers (D001L/057 to D001L/067)

| | | Results of analytical Tests performed on LFHC | | | | | | | | | | |
|---|---|---|---|---|---|---|---|---|---|---|---|---|
| Analytical Test | Limits | D001L/057 | D001L/058 | D001L/059 | D001L/060 | D001L/061 | D001L/062 | D001L/063 | D001L/064 | D001L/065 | D001L/066 | D001L/067 |
| Identification (HPLC) | Positive | Positive | Positive | Positive | Positive | Positive | Positive | Positive | Positive | Positive | Positive | Positive |
| Content Uniformity | Complies | Not Complies | Not Complies | Not Complies | Complies | Not Complies | Complies | Complies | Not Complies | Not Complies | Not Complies | Not Complies |
| Assay (HPLC) | 95.0%-105.0% | 77.2 | 100.8 | 95.6 | 99.0 | 92.3 | 98.9 | 98.6 | 91.2 | 99.3 | 97.3 | 95.3 |
| Related substances (HPLC) | | | | | | | | | | | | |
| HP1 | ≤0.50% | 0.11 | 0.09 | 0.27 | 0.12 | 0.12 | 0.20 | 0.13 | 0.25 | 0.06 | 0.10 | 0.14 |
| BM1 Dimer | ≤0.20% | 0.04 | 0.05 | 0.05 | 0.04 | 0.04 | 0.04 | 0.05 | 0.04 | 0.04 | 0.04 | 0.04 |
| BM1EE | ≤0.50% | 0.11 | 0.14 | 0.14 | 0.15 | 0.14 | 0.13 | 0.14 | 0.15 | 0.13 | 0.12 | 0.13 |
| NP1 | ≤0.20% | 0.01 | 0.01 | 0.01 | 0.01 | 0.01 | 0.01 | 0.01 | n.d. | 0.01 | 0.01 | 0.01 |
| Ind. Unknown impurity | ≤0.10% | n.d. | n.d. | 0.03 | n.d. | n.d. | n.d. | 0.05 | 0.16 | n.d. | n.d. | n.d. |
| Total impurities | ≤1.50% | 0.27 | 0.29 | 0.50 | 0.32 | 0.31 | 0.38 | 0.38 | 0.60 | 0.24 | 0.27 | 0.32 |
| Dissolution Test (Medium: buffer pH = 1.5) | | | | | | | | | | | | |
| (% 10 min) | 80% in 30 min | 34.9 | 32.0 | 42.5 | 30.2 | 61.2 | 30.9 | 46.8 | 86.6 | 68.0 | 82.8 | 54.3 |
| (% 20 min) | | 51.8 | 54.2 | 60.4 | 43.9 | 81.5 | 47.8 | 74.3 | 93.1 | 81.2 | 90.7 | 70.3 |
| (% 30 min) | | 57.1 | 68.0 | 71.7 | 54.8 | 87.4 | 62.5 | 88.9 | 93.7 | 85.6 | 92.3 | 76.7 |

TABLE 13c.1

Analytical results of batches containing bendamustine hydrochloride with low and medium viscosity carriers without viscosity modifiers (D001L/068, D001L/078, D001L/088, D001L/089 and D001L/092)

| | | Results of analytical Tests performed on LFHC | | | | |
|---|---|---|---|---|---|---|
| Analytical Test | Limits | D001L/068 | D001L/078 | D001L/088 | D001L/089 | D001L/092 |
| Identification (HPLC) | Positive | Positive | Positive | Positive | Positive | Positive |
| Content Uniformity | Complies | Complies | Not Complies | Complies | Not Complies (RSD 10.24) | Not Complies (RSD 8.88) | 
| | | | | | | Not Complies (RSD 6.30) |
| Assay (HPLC) | 95.0%-105.0% | 99.8 | 103.3 | 97.4 | 94.0 | 89.9 |
| Related substances (HPLC) | | | | | | |
| HP1 | ≤0.50% | 0.13 | 0.07 | 0.04 | 0.08 | 0.09 |
| BM1 Dimer | ≤0.20% | 0.04 | 0.04 | 0.03 | 0.04 | 0.27 |
| BM1EE | ≤0.50% | 0.13 | 0.15 | 0.10 | 0.13 | 0.14 |
| NP1 | ≤0.20% | 0.01 | 0.01 | 0.01 | 0.01 | 0.01 |
| Ind. Unknown impurity | ≤0.10% | n.d. | 0.02 | 0.05 | n.d. | 0.20 |
| Total impurities | ≤1.50% | 0.31 | 0.29 | 0.23 | 0.26 | 0.73 |
| Dissolution Test (Medium: buffer pH = 1.5) | | | | | | |
| (% 10 min) | 80% in 30 min | 65.4 | 95.7 | 93.5 | 51.7 | 95.9 |
| (% 20 min) | | 89.0 | 96.7 | 92.0 | 69.0 | 96.8 |
| (% 30 min) | | 95.2 | 95.0 | 89.9 | 79.6 | 94.7 |

TABLE 13.c.2

Analytical results of batches containing bendamustine hydrochloride with liquid carriers without viscosity modifiers
(Batch D001L/093 stored into aluminium blister)

| | | D001L/093 (TWEEN 20, liquid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 722.37 mg | N.A. | N.A. | 722.37 mg | N.A. |
| | CV | 1.2 | | | 1.2 | |
| Content Uniformity | Complies | Complies | N.A. | N.A. | Complies | N.A. |
| | CV | 4.63 | | | 4.63 | |
| Assay (HPLC) | 95.0%-105.0% | 102.3 | 95.7 | 102.3 | 102.3 | 101.5 |
| Related substances (HPLC) | | | | | | |
| HP1 | ≤0.50% | 0.39 | 0.18 | 0.64 | 0.39 | 0.06 |
| BM1 Dimer | ≤0.20% | 0.04 | 0.12 | 0.34 | 0.04 | 0.19 |
| BM1EE | ≤0.50% | 0.12 | 0.12 | 0.11 | 0.12 | 0.1 |
| NP1 | ≤0.20% | 0.01 | 0.01 | 0.01 | 0.01 | 0.01 |
| Major Unknon impurity (RRT) | ≤0.10% | 0.30 (0.70) | 0.27 (0.70) | 1.14 | 0.30 (0.70) | 0.26 |
| Total impurities | ≤1.50% | 0.86 | 0.70 | 2.85 | 0.86 | 0.74 |
| Dissolution Test | 80% in 30 mins | pass | pass | pass | pass | pass |
| (% 10 min) | Average (%) | 102.7 | 74.5 | 41.2 | 102.7 | 100.7 |
| | min (%)-max (%) | 98.8-104.8 | 32.5-100.3 | 26.3-64.4 | 98.8-104.8 | 93.1-107.5 |
| | RSD | 2.3 | 34.7 | 33.6 | 2.3 | 4.6 |
| (% 20 min) | Average (%) | 103.0 | 94.2 | 69.2 | 103.0 | 102.2 |
| | min (%)-max (%) | 100.7-104.8 | 78.2-102.8 | 46.2-87.9 | 100.7-104.8 | 100.6-105.9 |
| | RSD | 1.3 | 9.2 | 23.2 | 1.3 | 1.9 |
| (% 30 min) | Average (%) | 101.3 | 102.0 | 88.3 | 101.3 | 100.7 |
| | min (%)-max (%) | 99.7-102.2 | 98.1-105.0 | 58.2-100.6 | 99.7-102.2 | 99.7-100.6 |
| | RSD | 0.9 | 2.4 | 17.1 | 0.9 | 1.8 |
| FAST POINT (% 60 min) | Average (%) | N.A. | N.A. | N.A. | N.A. | N.A. |
| | min (%)-max (%) | | | | | |
| | RSD | | | | | |
| Moisture content | | 2.75 | 2.91 | 2.72 | 2.75 | 2.13 |

TABLE 23.c.3

Analytical results of batches containing bendamustine hydrochloride with liquid carriers without viscosity modifiers
(Batch D001L/094 stored into aluminium blister)

| | | D001L/094 (TWEEN 81, liquid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 699.18 mg | N.A. | N.A. | 699.18 mg | N.A. |
| | CV | 1.1 | | | 1.1 | |
| Content Uniformity | Complies | Complies | N.A. | N.A. | Complies | N.A. |
| | CV | 4.63 | | | 4.63 | |
| Assay (HPLC) | 95.0%-105.0% | 101.2 | 96.2 | 92.9 | 101.2 | 100.1 |
| Related substances (HPLC) | | | | | | |
| HP1 | ≤0.50% | 0.25 | 0.24 | 0.67 | 0.25 | 0.07 |
| BM1 Dimer | ≤0.20% | 0.05 | 0.39 | 0.97 | 0.05 | 0.24 |
| BM1EE | ≤0.50% | 0.13 | 0.12 | 0.11 | 0.13 | 0.1 |
| NP1 | ≤0.20% | 0.01 | 0.01 | 0.01 | 0.01 | 0.01 |
| Major Unknon impurity (RRT) | ≤0.10% | 0.20 (0.70) | 0.27 (0.70) | 0.20 | 0.20 (0.70) | 0.19 |
| Total impurities | ≤1.50% | 0.71 | 1.03 | 2.12 | 0.71 | 0.61 |
| Dissolution Test | 80% in 30 mins | fail | fail | fail | fail | fail |
| (% 10 min) | Average (%) | 12.5 | 10.0 | 8.1 | 12.5 | 19.1 |
| | min (%)-max (%) | 8.5-16.4 | 7.0-15.3 | 2.1-18.6 | 8.5-16.4 | 6.6-27.3 |
| | RSD | 25.8 | 31.1 | 86.3 | 25.8 | 42.8 |
| (% 20 min) | Average (%) | 27.6 | 21.1 | 17.4 | 27.6 | 34.8 |
| | min (%)-max (%) | 19.7-35.3 | 15.2-34.5 | 6.9-35.6 | 19.7-35.3 | 14.2-63.9 |
| | RSD | 19.5 | 34.3 | 73.2 | 19.5 | 50.0 |

TABLE 23.c.3-continued

Analytical results of batches containing bendamustine hydrochloride with liquid carriers without viscosity modifiers
(Batch D001L/094 stored into aluminium blister)

| | | D001L/094 (TWEEN 81, liquid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| (% 30 min) | Average (%) | 36.7 | 32.7 | 23.2 | 36.7 | 41.3 |
| | min (%)-max (%) | 28.8-42.4 | 23.5-54.5 | 9.4-45.9 | 28.8-42.4 | 18.6-59.3 |
| | RSD | 13.7 | 35.6 | 72.2 | 13.7 | 42.7 |
| FAST POINT (% 60 min) | Average (%) | N.A. | N.A. | 112.5 | N.A. | 158.9 |
| | min (%)-max (%) | | | 23.5-152.5 | | 154.0-167.9 |
| | RSD | | | 42.6 | | 3.3 |
| Moisture content | | 2.21 | 2.60 | 2.27 | 2.21 | 2.21 |

TABLE 33.c.4

Analytical results of batches containing bendamustine hydrochloride with liquid carriers without viscosity modifiers
(Batch D001L/095 stored into aluminium blister)

| | | D001L/095 (GLYCEROX HE, liquid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 713.05 mg | N.A. | N.A. | 713.05 mg | N.A. |
| | CV | 1.7 | | | 1.7 | |
| Content Uniformity | Complies | Complies | N.A. | N.A. | Complies | N.A. |
| | CV | 4.15 | | | 4.15 | |
| Assay (HPLC) | 95.0%-105.0% | 102.1 | 98.8 | 98.4 | 102.1 | 110.9 |
| Related substances (HPLC) | | | | | | |
| HP1 | ≤0.50% | 0.10 | 0.12 | 0.10 | 0.10 | 0.07 |
| BM1 Dimer | ≤0.20% | 0.04 | 0.06 | 0.24 | 0.04 | 0.16 |
| BM1EE | ≤0.50% | 0.12 | 0.12 | 0.11 | 0.12 | 0.11 |
| NP1 | ≤0.20% | 0.01 | 0.01 | 0.01 | 0.01 | 0.01 |
| Major Unknon impurity (RRT) | ≤0.10% | 0.21 (0.70) | 0.32 (0.70) | 0.38 | 0.21 (0.70) | 0.28 (0.25) |
| Total impurities | ≤1.50% | 0.48 | 0.76 | 1.16 | 0.48 | 0.83 |
| Dissolution Test | 80% in 30 mins | pass | pass | pass | pass | pass |
| (% 10 min) | Average (%) | 102.9 | 100.9 | 101.0 | 102.9 | 109.6 |
| | min (%)-max (%) | 95.6-107.6 | 92.9-108.1 | 91.6-128.0 | 95.6-107.6 | 106.1-112.5 |
| | RSD | 4.0 | 5.8 | 13.5 | 4.0 | 2.2 |
| (% 20 min) | Average (%) | 105.5 | 103.5 | 103.4 | 105.5 | 111.1 |
| | min (%)-max (%) | 102.1-109.3 | 94.9-111.4 | 97.5-121.9 | 102.1-109.3 | 109.3-112.4 |
| | RSD | 3.1 | 6.7 | 8.9 | 3.1 | 1.0 |
| (% 30 min) | Average (%) | 104.6 | 102.0 | 99.3 | 104.6 | 108.9 |
| | min (%)-max (%) | 101.5-106.9 | 93.6-108.1 | 97.3-103.5 | 101.5-106.9 | 107.4-111.1 |
| | RSD | 2.3 | 6.3 | 2.5 | 2.3 | 1.2 |
| FAST POINT (% 60 min) | Average (%) | N.A. | N.A. | N.A. | N.A. | N.A. |
| | min (%)-max (%) | | | | | |
| | RSD | | | | | |
| Moisture content | | 1.27 | 1.46 | 1.06 | 1.27 | 1.21 |

TABLE 43.c.5

Analytical results of batches containing bendamustine hydrochloride with liquid carriers without viscosity modifiers
(Batch D001L/097 stored into aluminium blister)

| | | D001L/097 (PLURONIC L35, liquid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 719.69 mg | N.A. | N.A. | 719.69 mg | N.A. |
| CV | | 1.1 | | | 1.1 | |
| Content Uniformity | Complies | Complies | N.A. | N.A. | Complies | N.A. |
| CV | | 4.54 | | | 4.54 | |
| Assay (HPLC) | 95.0%-105.0% | 103.7 | 99.3 | 103.8 | 103.7 | 105.6 |
| Related substances (HPLC) | | | | | | |
| HP1 | ≤0.50% | 0.20 | 0.67 | 0.14 | 0.20 | 0.01 |
| BM1 Dimer | ≤0.20% | 0.28 | 0.05 | 0.13 | 0.28 | 0.15 |
| BM1EE | ≤0.50% | 0.12 | 0.11 | 0.11 | 0.12 | 0.03 |
| NP1 | ≤0.20% | 0.01 | 0.01 | 0.01 | 0.01 | 0 |
| Major Unknon impurity (RRT) | ≤0.10% | nd | 0.16 (0.82) | nd | nd | 0.02 (0.93) |
| Total impurities | ≤1.50% | 0.61 | 1.06 | 0.39 | 0.61 | 0.22 |
| Dissolution Test | 80% in 30 mins | pass | pass | pass | pass | pass |
| (% 10 min) | Average (%) | 63.4 | 87.4 | 80.3 | 63.4 | 80.7 |
| | min (%)-max (%) | 35.2-83.7 | 77.3-113.3 | 59.1-105.3 | 35.2-83.7 | 63.5-107.1 |
| | RSD | 27.8 | 15.6 | 20.0 | 27.8 | 19.2 |
| (% 20 min) | Average (%) | 96.3 | 96.2 | 101.2 | 96.3 | 99.0 |
| | min (%)-max (%) | 92.9-99.5 | 94.2-98.6 | 99.3-104.2 | 92.9-99.5 | 91.4-105.6 |
| | RSD | 2.9 | 1.8 | 2.2 | 2.9 | 5.0 |
| (% 30 min) | Average (%) | 95.8 | 95.8 | 102.6 | 95.8 | 100.9 |
| | min (%)-max (%) | 92.3-99.8 | 91.4-99.3 | 101.2-103.4 | 92.3-99.8 | 97.8-103.8 |
| | RSD | 3.1 | 3.2 | 0.9 | 3.1 | 2.4 |
| FAST POINT (% 60 min) | Average (%) | N.A. | N.A. | N.A. | N.A. | N.A. |
| | min (%)-max (%) | | | | | |
| | RSD | | | | | |
| Moisture content | | 1.14 | 1.29 | 0.89 | 1.14 | 1.05 |

TABLE 53.c.6

Analytical results of batches containing bendamustine hydrochloride with liquid carriers without viscosity modifiers
(Batch D001L/098 stored into aluminium blister)

| | | D001L/098 (BRIJ L4, liquid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 657.14 mg | N.A. | N.A. | 657.14 mg | N.A. |
| CV | | 3.0 | | | 3.0 | |
| Content Uniformity | Complies | Not Complies | N.A. | N.A. | Not Complies | N.A. |
| CV | | 6.07 | | | 6.07 | |
| Assay (HPLC) | 95.0%-105.0% | 90.3 | 86.9 | 93.0 | 90.3 | 91.6 |
| Related substances (HPLC) | | | | | | |
| HP1 | ≤0.50% | 0.07 | 0.47 | 0.17 | 0.07 | 0.1 |
| BM1 Dimer | ≤0.20% | 0.28 | 0.06 | 0.17 | 0.28 | 0.16 |
| BM1EE | ≤0.50% | 0.11 | 0.10 | 0.09 | 0.11 | 0.10 |
| NP1 | ≤0.20% | 0.01 | 0.01 | 0.01 | 0.01 | 0.01 |
| Major Unknon impurity (RRT) | ≤0.10% | 0.04 (0.70) | 0.17 (0.70) | 0.49 | 0.04 (0.70) | 0.25 (0.22) |
| Total impurities | ≤1.50% | 0.51 | 1.00 | 1.14 | 0.51 | 1.04 |
| Dissolution Test | 80% in 30 mins | fail | fail | fail | fail | fail |
| (% 10 min) | Average (%) | 16.6 | 9.0 | 31.1 | 16.6 | 39.8 |
| | min (%)-max (%) | 2.70-31.7 | 4.70-15.7 | 16.4-66.2 | 2.70-31.7 | 28.2-54.3 |
| | RSD | 65.9 | 44.6 | 58.8 | 65.9 | 25.2 |
| (% 20 min) | Average (%) | 31.6 | 20.6 | 41.8 | 31.6 | 53.7 |
| | min (%)-max (%) | 20.6-46.3 | 17.1-23.5 | 29.4-61.5 | 20.6-46.3 | 35.6-71.5 |
| | RSD | 33.6 | 11.4 | 27.5 | 33.6 | 28.7 |

TABLE 53.c.6-continued

Analytical results of batches containing bendamustine hydrochloride with liquid carriers without viscosity modifiers
(Batch D001L/098 stored into aluminium blister)

| | | D001L/098 (BRIJ L4, liquid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| (% 30 min) | Average (%) | 44.3 | 29.3 | 57.5 | 44.3 | 68.1 |
| | min (%)-max (%) | 31.6-68.4 | 22.4-32.4 | 36.5-75.6 | 31.6-68.4 | 44.6-88.1 |
| | RSD | 32.7 | 13.9 | 26.9 | 32.7 | 26.0 |
| FAST POINT (% 60 min) | Average (%) | N.A. | 61.6 | 121.1 | N.A. | 100.2 |
| | min (%)-max (%) | | 53.9-81.0 | 114.5-125.7 | | 80.9-111.8 |
| | RSD | | 16.6 | 3.1 | | 12.1 |
| Moisture content | | 1.30 | 1.56 | 1.13 | 1.30 | 1.07 |

TABLE 63.c.7

Analytical results of batches containing bendamustine hydrochloride with liquid carriers without viscosity modifiers
(Batch D001L/099 stored into aluminium blister)

| | | D001L/099 (PLURONIC L64, liquid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 684.23 mg | N.A. | NA. | 684.23 mg | N.A. |
| | CV | 3.6 | | | 3.6 | |
| Content Uniformity | Complies | Complies | N.A. | N.A. | Complies | N.A. |
| | CV | 5.00 | | | 5.00 | |
| Assay (HPLC) | 95.0%-105.0% | 97.6 | 97.1 | 99.2 | 97.6 | 101.2 |
| Related substances (HPLC) | | | | | | |
| HP1 | ≤0.50% | 0.18 | 1.06 | 0.18 | 0.18 | 0.1 |
| BM1 Dimer | ≤0.20% | 0.26 | 0.07 | 0.16 | 0.26 | 0.15 |
| BM1EE | ≤0.50% | 0.12 | 0.12 | 0.11 | 0.12 | 0.11 |
| NP1 | ≤0.20% | 0.01 | 0.02 | 0.01 | 0.01 | 0.01 |
| Major Unknon impurity (RRT) | ≤0.10% | nd | 0.10 (0.70) | nd | nd | nd |
| Total impurities | ≤1.50% | 0.57 | 1.37 | 0.46 | 0.57 | 0.37 |
| Dissolution Test | 80% in 30 mins | pass | pass | pass | pass | pass |
| (% 10 min) | Average (%) | 56.3 | 44.2 | 41.7 | 56.3 | 41.5 |
| | min (%)-max (%) | 37.3-80.6 | 22.0-61.1 | 12.3-79.1 | 37.3-80.6 | 33.8-60.1 |
| | RSD | 30.6 | 32.1 | 62.7 | 30.6 | 23.5 |
| (% 20 min) | Average (%) | 89.2 | 77.3 | 74.2 | 89.2 | 81.8 |
| | min (%)-max (%) | 82.1-98.4 | 64.4-91.1 | 51.3-102.2 | 82.1-98.4 | 72.3-91.9 |
| | RSD | 6.7 | 12.2 | 29.3 | 6.7 | 8.9 |
| (% 30 min) | Average (%) | 95.8 | 93.9 | 98.1 | 95.8 | 97.3 |
| | min (%)-max (%) | 88.5-99.8 | 85.0-100.0 | 88.7-109.1 | 88.5-99.8 | 92.8-100.9 |
| | RSD | 4.4 | 6.1 | 7.8 | 4.4 | 3.6 |
| FAST POINT (% 60 min) | Average (%) | N.A. | N.A. | N.A. | N.A. | N.A. |
| | min (%)-max (%) | | | | | |
| | RSD | | | | | |
| Moisture content | | 0.91 | 1.15 | 1.07 | 0.91 | 1.04 |

TABLE 73.c.8

Analytical results of batches containing bendamustine hydrochloride with liquid carriers without viscosity modifiers
(Batch D001L/100 stored into aluminium blister)

| | | D001L/100 (PLURONIC L43, liquid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 710.09 mg | N.A. | N.A. | 710.09 mg | N.A. |
| CV | | 1.1 | | | 1.1 | |
| Content Uniformity | Complies | Complies | N.A. | N.A. | Complies | N.A. |
| CV | | 2.15 | | | 2.15 | |
| Assay (HPLC) | 95.0%-105.0% | 100.9 | 98.9 | 96.8 | 100.9 | 104.5 |
| Related substances (HPLC) | | | | | | |
| HP1 | ≤0.50% | 0.18 | 0.79 | 0.07 | 0.18 | 0.03 |
| BM1 Dimer | ≤0.20% | 0.29 | 0.06 | 0.13 | 0.29 | 0.14 |
| BM1EE | ≤0.50% | 0.12 | 0.12 | 0.06 | 0.12 | 0.09 |
| NP1 | ≤0.20% | 0.01 | 0.01 | 0.01 | 0.01 | 0.01 |
| Major Unknon impurity (RRT) | ≤0.10% | nd | 0.10 (0.82) | nd | nd | nd |
| Total impurities | ≤1.50% | 0.60 | 1.17 | 0.27 | 0.60 | 0.27 |
| Dissolution Test | 80% in 30 mins | pass | fail | fail | pass | fail |
| (% 10 min) | Average (%) | 62.1 | 38.7 | 43.0 | 62.1 | 27.8 |
| | min (%)-max (%) | 44.0-85.8 | 7.1-101.0 | 9.0-102.1 | 44.0-85.8 | 4.6-59.0 |
| | RSD | 27.5 | 106.6 | 87.2 | 27.5 | 91.3 |
| (% 20 min) | Average (%) | 92.7 | 55.6 | 76.4 | 92.7 | 58.1 |
| | min (%)-max (%) | 74.7-107.8 | 23.6-99.2 | 37.2-102.3 | 74.7-107.8 | 28.6-102.1 |
| | RSD | 11.6 | 62.3 | 37.2 | 11.6 | 51.4 |
| (% 30 min) | Average (%) | 98.2 | 67.9 | 87.1 | 98.2 | 72.9 |
| | min (%)-max (%) | 95.6-100.7 | 37.3-97.7 | 57.1-101.2 | 95.6-100.7 | 47.3-101.0 |
| | RSD | 2.0 | 36.6 | 20.9 | 2.0 | 31.8 |
| FAST POINT (% 60 min) | Average (%) | N.A. | 97.0 | na | N.A. | 97.4 |
| | min (%)-max (%) | | 94.5-100.3 | | | 95.4-100.4 |
| | RSD | | 2.3 | | | 2.0 |
| Moisture content | | 0.89 | 1.10 | 0.98 | 0.89 | 0.84 |

TABLE 83.c.9

Analytical results of batches containing bendamustine hydrochloride with liquid carriers without viscosity modifiers
(Batch D001L/119 stored into aluminium blister)

| | | D001L/119 (TWEEN 40, liquid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 704.09 | N.A. | N.A. | 704.09 | N.A. |
| CV | | 2.4 | | | 2.4 | |
| Content Uniformity | Complies | Not Complies | N.A. | N.A. | Not Complies | N.A. |
| CV | | 11.81 | | | 11.81 | |
| Assay (HPLC) | 95.0%-105.0% | 95.7 | 91.8 | | 95.7 | |
| Related substances (HPLC) | | | | | | |
| HP1 | ≤0.50% | 0.06 | 0.18 | | 0.06 | |
| BM1 Dimer | ≤0.20% | 0.04 | 0.18 | | 0.04 | |
| BM1EE | ≤0.50% | 0.11 | 0.11 | | 0.11 | |
| NP1 | ≤0.20% | 0.02 | 0.01 | | 0.02 | |
| Major Unknon impurity (RRT) | ≤0.10% | 0.12 | 0.25 | | 0.12 | |
| Total impurities | ≤1.50% | 0.35 | 0.73 | | 0.35 | |
| Dissolution Test | 80% in 30 mins | pass | pass | | pass | |
| (% 10 min) | Average (%) | 78.2 | 43.8 | | 78.2 | |
| | min (%)-max (%) | 73.4-91.1 | 9.6-82.1 | | 73.4-91.1 | |
| | RSD | 8.6 | 64.9 | | 8.6 | |
| (% 20 min) | Average (%) | 98.7 | 68.8 | | 98.7 | |
| | min (%)-max (%) | 97.9-100.4 | 29.2-101.8 | | 97.9-100.4 | |
| | RSD | 1.0 | 41.6 | | 1.0 | |

TABLE 83.c.9-continued

Analytical results of batches containing bendamustine hydrochloride with liquid carriers without viscosity modifiers
(Batch D001L/119 stored into aluminium blister)

| | | D001L/119 (TWEEN 40, liquid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| (% 30 min) | Average (%) | 98.0 | 85.2 | | 98.0 | |
| | min (%)-max (%) | 96.7-100.4 | 49.0-106.7 | | 96.7-100.4 | |
| | RSD | 1.5 | 26.5 | | 1.5 | |
| FAST POINT (% 60 min) | Average (%) | N.A. | N.A. | | N.A. | |
| | min (%)-max (%) | | | | | |
| | RSD | | | | | |
| Moisture content | | 2.19 | 2.55 | | 2.19 | |

Batches Manufactured with High Viscosity Carriers

Carriers that are semisolid or solid at room temperature and have a high viscosity were selected for use in the preparation of formulations containing bendamustine hydrochloride in order to evaluate the effect of temperature from the early stages of preparation up till and including the shelf life. High viscosity carriers are listed in table 14.

TABLE 14

High viscosity carriers

| Carrier | Melting point (range) (° C.) | Physical state at room temperature (RT) | Temperature at which the bulk suspension was filled into the capsules (° C.) |
|---|---|---|---|
| CREMOPHOR A6 | 50-55 | Semisolid | NA |
| CREMOPHOR A25 | 50-55 | Semisolid | NA |
| SOFTIGEN 701 | 30 | Semisolid | NA |
| SOFTISAN 649 | 40 | Semisolid | NA |
| CREMOPHOR RH 40 | 35 | Semisolid | NA |
| LUTROL F68 | 52-57 | Solid | NA |
| LUTROL F127/ PLURONIC F27 | 53-57 | Solid | NA |
| PLURONIC P85 | 45-50 | semisolid | 52 |
| PLURONIC P105 | 45-50 | semisolid | 50 |
| PLURONIC P103 | 45-50 | semisolid | 50 |
| PLURONIC F108 | 65-70 | solid | 70 |
| BRIJ 35/BRIJ L23 | 35-40 | solid | 42 |
| BRIJ 58 | 36 | semisolid | NA |
| BRIJ 56 | 31 | semisolid | NA |
| BRIJ96/BRIJ 97/BRIJ O10-SS | 30-34 | semisolid | 37 |
| BRIJ 98/BRIJ O 20-SO | 48-50 | semisolid | 55 |
| BRIJ 76/BRIJ S10 | 35-40 | solid | 43 |
| BRIJ78/BRIJ S20 | 38-40 | solid | 42 |
| BRIJ 52/BRIJ C2 | 36-42 | semisolid | 40 |
| BRIJ S721-SO | 46-51 | solid | 54 |
| SOLUTOL HS15 | 30 | semisolid | 33 |
| TWEEN 65 | 40-43 | semisolid | 43 |
| TWEEN 61 | 45-50 | semisolid | 46 |
| MYRJ 45/MIRJ S8-SS | 38-41 | semisolid | 44 |
| MYRJ 49/MIRJ S25 | 28-33 | semisolid | NA |
| MYRJ 52/MIRJ S40-PA | 40-45 | solid | 45 |
| MIRJ S100 | 54-60 | semisolid | 60 |
| GELUCIRE 44/14 | 44 | semisolid | 44 |
| SPEZIOL TPGS | 37-41 | semisolid | 45 |

The composition of all batches manufactured including the results of the analytical tests are reported in tables 15a and 15b.

The proposed manufacturing method for the LFHC formulations containing bendamustine hydrochloride was adding bendamustine hydrochloride to the melted carrier, homogenizing the mixture and filling the mixture at a temperature above 25° in the LICAPS capsules. The suspensions are semisolid or solid at room temperature; thus it was found to be necessary to fill these into the LICAPS capsules with the Capsule Filling and Sealing Machine CFS 1200 within a certain temperature range depending on their melting point (see table 14). Due to the high viscosity of the carriers at room temperature, sedimentation in these suspensions was not observed.

TABLE 15a

Manufactured active batches with high viscosity carriers

| | Batch No | | | | | | |
|---|---|---|---|---|---|---|---|
| Components | D001L/054 % | D001L/055 % | D001L/056 % | D001L/077 % | D001L/082 % | D001L/090 % | D001L/091 % |
| CREMOPHOR A6 | 90.8 | — | — | — | — | — | — |
| CREMOPHOR A25 | — | 90.8 | — | — | — | — | — |
| SOFTISAN 649 | — | — | 90.8 | — | — | — | — |
| SOFTIGEN 701 | — | — | — | 90.8 | — | — | — |
| CREMOPHOR RH 40 | — | — | — | — | 90.8 | — | — |
| LUTROL F68 | — | — | — | — | — | 90.8 | — |

TABLE 15a-continued

Manufactured active batches with high viscosity carriers

| Components | Batch No | | | | | | |
|---|---|---|---|---|---|---|---|
| | D001L/054 % | D001L/055 % | D001L/056 % | D001L/077 % | D001L/082 % | D001L/090 % | D001L/091 % |
| LUTROL F127 | — | — | — | — | — | — | 90.8 |
| Bendamustine HCl | 9.2 | 9.2 | 9.2 | 9.2 | 9.2 | 9.2 | 9.2 |

For all other carriers the same ratio between bendamustine hydrochloride and the carrier as for the carriers listed in Table 15a was used.

TABLE 15b.1

Analytical results for batches manufactured with high viscosity carrier

| Analytical Test | Limits | Results of analytical Tests performed on LFHC | | | | | | |
|---|---|---|---|---|---|---|---|---|
| | | D001L/054 | D001L/055 | D001L/056 | D001L/077 | D001L/082 | D001L/090 | D001L/091 |
| Identification (HPLC) | Positive | Positive | Positive | Positive | Positive | Positive | Positive | Positvr |
| Content Uniformity | Complies | Not Complies | Not Complies | Not Complies | Complies | Complies (RSD 2.66) | Not Complies (RSD 38.95) | Not Complies (RSD 34.70) |
| Assay (HPLC) | 95.0%-105.0% | 23.2 | 90.0 | 91.9 | 100.4 | 98.0 | 74.8 | 5.9 |
| Related substances (HPLC) | | | | | | | | |
| HP1 | ≤0.50% | 0.36 | 0.13 | 0.21 | 0.09 | 0.05 | 0.28 | 0.15 |
| BM1 Dimer | ≤0.20% | 0.05 | 0.06 | 0.05 | 0.04 | 0.04 | 0.04 | 0.10 |
| BM1EE | ≤0.50% | 0.15 | 0.14 | 0.13 | 0.15 | 0.14 | 0.11 | 0.13 |
| NP1 | ≤0.20% | n.d. | n.d. | 0.01 | 0.01 | 0.01 | 0.02 | 0.01 |
| Ind. Unknown impurity | ≤0.10% | 0.07 | 0.24 | 0.02 | 0.02 | 0.03 | 0.13 | 0.09 |
| Total impurities | ≤1.50% | 0.63 | 0.57 | 0.42 | 0.31 | 0.29 | 0.58 | 0.54 |
| Dissolution Test (Medium: buffer pH = 1.5) | | | | | | | | |
| (% 10 min) | 80% in 30 min | 0.6 | 3.3 | 11.7 | 35.8 | 56.9 | 0.8 | 0.0 |
| (% 20 min) | | 1.6 | 17.1 | 15.8 | 53.4 | 80.4 | 32.1 | 0.0 |
| (% 30 min) | | 3.2 | 34.3 | 18.0 | 65.5 | 93.8 | 61.1 | 1.2 |

TABLE 15b.2

Analytical results for batches manufactured with high viscosity carrier

| | | D001L/096 (BRIJ O10, semisolid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 681.69 mg CV 2.0 | N.A. | N.A. | 681.69 mg CV 2.0 | N.A. |
| Content Uniformity | Complies | Complies CV 4.00 | N.A. | N.A. | Complies CV 4.00 | N.A. |
| Assay (HPLC) | 95.0%-105.0% | 91.1 | 90.7 | 92.3 | 91.1 | 95.5 |
| Related substances (HPLC) | | | | | | |
| HP1 | ≤0.50% | 0.09 | 0.48 | 0.15 | 0.09 | 0.07 |
| BM1 Dimer | ≤0.20% | 0.05 | 0.04 | 0.18 | 0.05 | 0.13 |
| BM1EE | ≤0.50% | 0.12 | 0.09 | 0.09 | 0.12 | 0.1 |
| NP1 | ≤0.20% | 0.01 | 0.01 | 0.01 | 0.01 | 0.01 |
| Major Unknon impurity (RRT) | ≤0.10% | 0.08 (0.70) | 0.10 (0.70) | 0.10 | 0.08 (0.70) | 0.09 |
| Total impurities | ≤1.50% | 0.43 | 0.74 | 0.53 | 0.43 | 0.40 |
| Dissolution Test | 80% in 30 mins | fail | fail | fail | fail | fail |

TABLE 15b.2-continued

Analytical results for batches manufactured with high viscosity carrier

D001L/096 (BRIJ O10, semisolid)

| Analytical Test | Limits | Storage conditions: 40° C.-75% RH | | | Storage conditions: 25° C.-60% RH | |
|---|---|---|---|---|---|---|
| | | 0 | 1 month | 3 months | 0 | 3 months |
| (% 10 min) | Average (%) | 8.0 | 7.4 | 7.8 | 8.0 | 8.8 |
| | min (%)-max (%) | 5.8-9.7 | 2.4-18.4 | 1.2-25.7 | 5.8-9.7 | 7.0-11.0 |
| | RSD | 19.3 | 77.2 | 123.2 | 19.3 | 19.0 |
| (% 20 min) | Average (%) | 22.9 | 26.3 | 25.7 | 22.9 | 22.1 |
| | min (%)-max (%) | 18.8-28.9 | 16.4-42.7 | 13.2-45.6 | 18.8-28.9 | 19.8-23.6 |
| | RSD | 15.2 | 35.5 | 49.1 | 15.2 | 6.5 |
| (% 30 min) | Average (%) | 35.9 | 59.0 | 66.9 | 35.9 | 36.6 |
| | min (%)-max (%) | 31.7-43.0 | 42.0-79.8 | 54.6-83.2 | 31.7-43.0 | 34.6-43.2 |
| | RSD | 11.8 | 25.2 | 16.5 | 11.8 | 9.1 |
| FAST POINT (% 60 min) | Average (%) | N.A. | 97.7 | 92.2 | N.A. | 92.8 |
| | min (%)-max (%) | | 94.1-99.8 | 87.6-95.7 | | 89.3-95.0 |
| | RSD | | 2.1 | 3.0 | | 2.1 |
| Moisture content | | 1.18 | 1.39 | 1.53 | 1.18 | 1.23 |

TABLE 15b.3

Analytical results for batches manufactured with high viscosity carrier

D001L/101 (PLURONIC P85, semisolid)

| Analytical Test | Limits | Storage conditions: 40° C.-75% RH | | | Storage conditions: 25° C.-60% RH | |
|---|---|---|---|---|---|---|
| | | 0 | 1 month | 3 months | 0 | 3 months |
| Identification (HPLC) | Positive | Positive | Positive | Positive | Positive | Positive |
| Mean Weight (mg/cps) | 685-725 | 705.25 mg | N.A. | N.A. | 705.25 mg | N.A. |
| | CV | 1.8 | | | 1.8 | |
| Content Uniformity | Complies | Not Complies | N.A. | N.A. | Not Complies | N.A. |
| | CV | 14.30 | | | 14.30 | |
| Assay (HPLC) | 95.0%-105.0% | 98.8 | 98.3 | 84.1 | 98.8 | 104.6 |
| Related substances (HPLC) | | | | | | |
| HP1 | ≤0.50% | 0.7 | 0.12 | 0.06 | 0.7 | 0.03 |
| BM1 Dimer | ≤0.20% | 0.30 | 0.04 | 0.02 | 0.30 | 0.16 |
| BM1EE | ≤0.50% | 0.06 | 0.10 | 0.06 | 0.06 | 0.07 |
| NP1 | ≤0.20% | 0.01 | 0.01 | 0.01 | 0.01 | 0.01 |
| Major Unknon impurity (RRT) | ≤0.10% | nd | nd | nd | nd | 0.04 (0.84) |
| Total impurities | ≤1.50% | 0.44 | 0.27 | 0.15 | 0.44 | 0.33 |
| Dissolution Test | 80% in 30 mins | fail | fail | fail | fail | fail |
| (% 10 min) | Average (%) | 8.0 | 8.9 | 8.1 | 8.0 | 6.1 |
| | min (%)-max (%) | 3.6-12.5 | 3.3-18.6 | 2.0-15.7 | 3.6-12.5 | 2.7-9.9 |
| | RSD | 54.8 | 62.2 | 55.1 | 54.8 | 44.1 |
| (% 20 min) | Average (%) | 29.1 | 27.0 | 26.3 | 29.1 | 29.8 |
| | min (%)-max (%) | 12.5-40.9 | 17.5-39.1 | 20.4-29.9 | 12.5-40.9 | 20.3-39.2 |
| | RSD | 37.6 | 30.0 | 14.1 | 37.6 | 21.4 |
| (% 30 min) | Average (%) | 59.0 | 55.5 | 50.6 | 59.0 | 57.8 |
| | min (%)-max (%) | 29.8-75.8 | 37.6-75.0 | 44.5-61.7 | 29.8-75.8 | 31.6-74.4 |
| | RSD | 29.6 | 22.4 | 12.7 | 29.6 | 25.1 |
| FAST POINT (% 60 min) | Average (%) | N.A. | 99.3 | 102.2 | N.A. | 99.9 |
| | min (%)-max (%) | | 97.5-101.2 | 99.0-105.7 | | 98.6-101.2 |
| | RSD | | 1.4 | 2.4 | | 0.9 |
| Moisture content | | 0.70 | 1.06 | 0.80 | 0.70 | 0.60 |

TABLE 15b.4

Analytical results for batches manufactured with high viscosity carrier

D001L/102 (PLURONIC P105, semisolid)

| Analytical Test | Limits | Storage conditions: 40° C.-75% RH | | | Storage conditions: 25° C.-60% RH | |
|---|---|---|---|---|---|---|
| | | 0 | 1 month | 3 months | 0 | 3 months |
| Identification (HPLC) | Positive | Positive | Positive | Positive | Positive | Positive |
| Mean Weight (mg/cps) | 685-725 | 680.32 mg | N.A. | N.A. | 680.32 mg | N.A. |
| | CV | 2.3 | | | 2.3 | |
| Content Uniformity | Complies | Not Complies | N.A. | N.A. | Not Complies | N.A. |
| | CV | 26.17 | | | 26.17 | |
| Assay (HPLC) | 95.0%-105.0% | 78.9 | 93.6 | 61.1 | 78.9 | 31.3 |
| Related substances (HPLC) | | | | | | |
| HP1 | ≤0.50% | 0.15 | 0.13 | 0.05 | 0.15 | 0.02 |
| BM1 Dimer | ≤0.20% | 0.17 | 0.03 | 0.11 | 0.17 | 0.10 |
| BM1EE | ≤0.50% | 0.08 | 0.09 | 0.04 | 0.08 | 0.02 |
| NP1 | ≤0.20% | 0.01 | 0.01 | 0.00 | 0.01 | 0.00 |
| Major Unknon impurity (RRT) | ≤0.10% | nd | nd | 0.01 | nd | 0.03 (0.84) |
| Total impurities | ≤1.50% | 0.41 | 0.26 | 0.21 | 0.41 | 0.17 |
| Dissolution Test | 80% in 30 mins | fail | fail | fail | fail | fail |
| (% 10 min) | Average (%) | 3.0 | 0.5 | 0.7 | 3.0 | 2.8 |
| | min (%)-max (%) | 0.6-5.6 | 0.2-0.8 | 0.0-1.5 | 0.6-5.6 | 0.0-5.2 |
| | RSD | 64.9 | 47.5 | 96.1 | 64.9 | 78.2 |
| (% 20 min) | Average (%) | 13.0 | 6.2 | 7.0 | 13.0 | 12.7 |
| | min (%)-max (%) | 4.9-20.0 | 3.5-9.0 | 2.2-12.1 | 4.9-20.0 | 5.7-18.8 |
| | RSD | 49.2 | 37.9 | 51.1 | 49.2 | 44.2 |
| (% 30 min) | Average (%) | 27.2 | 17.7 | 17.3 | 27.2 | 25.6 |
| | min (%)-max (%) | 15.7-37.7 | 13.1-22.9 | 7.9-26.9 | 15.7-37.7 | 12.7-36.4 |
| | RSD | 33.8 | 24.5 | 39.5 | 33.8 | 38.6 |
| FAST POINT (% 60 min) | Average (%) | 97.0 | 99.4 | 96.0 | 97.0 | 101.2 |
| | min (%)-max (%) | 85.3-101.7 | 96.0-104.4 | 63.5-107.3 | 85.3-101.7 | 96.5-107.2 |
| | RSD | 6.1 | 3.0 | 17.0 | 6.1 | 4.7 |
| Moisture content | | 0.44 | 0.67 | 0.73 | 0.44 | 0.38 |

TABLE 15b.5

Analytical results for batches manufactured with high viscosity carrier

D001L/103 (BRIJ O20, semisolid)

| Analytical Test | Limits | Storage conditions: 40° C.-75% RH | | | Storage conditions: 25° C.-60% RH | |
|---|---|---|---|---|---|---|
| | | 0 | 1 month | 3 months | 0 | 3 months |
| Identification (HPLC) | Positive | Positive | Positive | Positive | Positive | Positive |
| Mean Weight (mg/cps) | 685-725 | 699.05 | N.A. | N.A. | 699.05 | N.A. |
| | CV | 2.4 | | | 2.4 | |
| Content Uniformity | Complies | Not Complies | N.A. | N.A. | Not Complies | N.A. |
| | CV | 14.44 | | | 14.44 | |
| Assay (HPLC) | 95.0%-105.0% | 62.6 | 72.2 | 97.4 | 62.6 | 91.6 |
| Related substances (HPLC) | | | | | | |
| HP1 | ≤0.50% | 0.27 | 0.17 | 0.09 | 0.27 | 0.07 |
| BM1 Dimer | ≤0.20% | 0.40 | 0.04 | 0.13 | 0.40 | 0.15 |
| BM1EE | ≤0.50% | 0.11 | 0.11 | 0.08 | 0.11 | 0.10 |
| NP1 | ≤0.20% | 0.01 | 0.01 | 0.01 | 0.01 | 0.01 |
| Major Unknon impurity (RRT) | ≤0.10% | 0.13 (0.70) | 0.16 (0.70) | 0.12 | 0.13 (0.70) | 0.10 (0.25) |
| Total impurities | ≤1.50% | 0.95 | 0.49 | 0.43 | 0.95 | 0.52 |
| Dissolution Test | 80% in 30 mins | fail | fail | fail | fail | fail |
| (% 10 min) | Average (%) | 6.0 | 2.5 | 0.5 | 6.0 | 4.1 |
| | min (%)-max (%) | 4.5-7.2 | 1.0-7.6 | 0.0-1.5 | 4.5-7.2 | 2.0-8.2 |
| | RSD | 16.9 | 110.3 | 112.3 | 16.9 | 58.4 |
| (% 20 min) | Average (%) | 33.1 | 15.5 | 7.4 | 33.1 | 24.6 |
| | min (%)-max (%) | 30.7-39.6 | 11.6-30.1 | 5.9-11.3 | 30.7-39.6 | 17.0-36.1 |
| | RSD | 9.9 | 51.4 | 26.9 | 9.9 | 27.6 |

TABLE 15b.5-continued

Analytical results for batches manufactured with high viscosity carrier

| | | D001L/103 (BRIJ O20, semisolid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| (% 30 min) | Average (%) | 68.6 | 38.5 | 23.9 | 68.6 | 59.1 |
| | min (%)-max (%) | 63.7-82.4 | 32.1-58.5 | 19.8-28.8 | 63.7-82.4 | 48.3-76.0 |
| | RSD | 13.1 | 35.8 | 14.1 | 13.1 | 15.8 |
| FAST POINT (% 60 min) | Average (%) | 91.0 | 95.8 | 105.5 | 91.0 | 92.3 |
| | min (%)-max (%) | 87.0-95.3 | 93.8-96.8 | 101.1-109.4 | 87.0-95.3 | 89.6-95.0 |
| | RSD | 3.8 | 1.1 | 3.3 | 3.8 | 2.1 |
| Moisture content | | 0.57 | 0.96 | 1.07 | 0.57 | 0.82 |

TABLE 15b.6

Analytical results for batches manufactured with high viscosity carrier

| | | D001L/104 (PLURONIC P103, semisolid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 694.01 | N.A. | N.A. | 694.01 | N.A. |
| | CV | 1.5 | | | 1.5 | |
| Content Uniformity | Complies | Not Complies | N.A. | N.A. | Not Complies | N.A. |
| | CV | 8.81 | | | 8.81 | |
| Assay (HPLC) | 95.0%-105.0% | 65.0 | 94.6 | 94.0 | 65.0 | 60.0 |
| Related substances (HPLC) | | | | | | |
| HP1 | ≤0.50% | 0.15 | 0.22 | 0.11 | 0.15 | 0.24 |
| BM1 Dimer | ≤0.20% | 0.21 | 0.03 | 0.10 | 0.21 | 0.11 |
| BM1EE | ≤0.50% | 0.11 | 0.11 | 0.06 | 0.11 | 0.07 |
| NP1 | ≤0.20% | 0.01 | 0.01 | 0.01 | 0.01 | 0.01 |
| Major Unknon impurity (RRT) | ≤0.10% | nd | nd | nd | nd | 0.04 (0.84) |
| Total impurities | ≤1.50% | 0.48 | 0.37 | 0.28 | 0.48 | 0.5 |
| Dissolution Test | 80% in 30 mins | fail | fail | fail | fail | fail |
| (% 10 min) | Average (%) | 8.6 | 26.2 | 19.3 | 8.6 | 4.6 |
| | min (%)-max (%) | 3.6-11.6 | 0.0-56.1 | 0.2-64.7 | 3.6-11.6 | 1.7-8.6 |
| | RSD | 43.0 | 102.7 | 149.6 | 43.0 | 54.3 |
| (% 20 min) | Average (%) | 19.1 | 47.4 | 36.2 | 19.1 | 13.5 |
| | min (%)-max (%) | 13.3-22.4 | 8.1-80.9 | 6.4-89.4 | 13.3-22.4 | 8.7-17.8 |
| | RSD | 21.1 | 58.5 | 99.5 | 21.1 | 22.2 |
| (% 30 min) | Average (%) | 30.5 | 72.2 | 61.6 | 30.5 | 24.0 |
| | min (%)-max (%) | 22.4-35.9 | 33.0-92.4 | 22.8-97.5 | 22.4-35.9 | 18.4-30.3 |
| | RSD | 15.8 | 31.6 | 45.1 | 15.8 | 16.1 |
| FAST POINT (% 60 min) | Average (%) | 82.2 | 99.6 | 99.7 | 82.2 | 77.9 |
| | min (%)-max (%) | 80.1-91.4 | 96.6-102.0 | 95.9-102.4 | 80.1-91.4 | 68.9-85.7 |
| | RSD | 8.4 | 1.8 | 2.3 | 8.4 | 9.2 |
| Moisture content | | 0.82 | 0.85 | 1.12 | 0.82 | 0.97 |

TABLE 15b.7

Analytical results for batches manufactured with high viscosity carrier

| | | D001L/105 (PLURONIC F108, solid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 245.86 | N.A. | | 245.86 | N.A. |
| | CV | 17.3 | | | 17.3 | |
| Content Uniformity | Complies | not performed | N.A. | | not performed | N.A. |
| | CV | not performed | | | not performed | |
| Assay (HPLC) | 95.0%-105.0% | not performed | N.A. | | not performed | N.A. |
| Related substances (HPLC) | | | | | | |
| HP1 | ≤0.50% | 0.03 | N.A. | | 0.03 | N.A. |
| BM1 Dimer | ≤0.20% | 0.16 | N.A. | | 0.16 | N.A. |
| BM1EE | ≤0.50% | 0.02 | N.A. | | 0.02 | N.A. |
| NP1 | ≤0.20% | 0 | N.A. | | 0 | N.A. |
| Major Unknon impurity (RRT) | ≤0.10% | nd | N.A. | | nd | N.A. |
| Total impurities | ≤1.50% | 0.21 | N.A. | | 0.21 | N.A. |
| Dissolution Test | 80% in 30 mins | fail | N.A. | | fail | N.A. |
| (% 10 min) | Average (%) | 0.0 | N.A. | | 0.0 | N.A. |
| | min (%)-max (%) | 0.0-0.0 | N.A. | | 0.0-0.0 | N.A. |
| | RSD | 0.0 | N.A. | | 0.0 | N.A. |
| (% 20 min) | Average (%) | 6.4 | N.A. | | 6.4 | N.A. |
| | min (%)-max (%) | 5.5-8.5 | N.A. | | 5.5-8.5 | N.A. |
| | RSD | 16.7 | N.A. | | 16.7 | N.A. |
| (% 30 min) | Average (%) | 18.4 | N.A. | | 18.4 | N.A. |
| | min (%)-max (%) | 13.4-25.0 | N.A. | | 13.4-25.0 | N.A. |
| | RSD | 25.6 | N.A. | | 25.6 | N.A. |
| FAST POINT (% 60 min) | Average (%) | 85.1 | N.A. | | 85.1 | N.A. |
| | min (%)-max (%) | 58.8-144.9 | N.A. | | 58.8-144.9 | N.A. |
| | RSD | 37.9 | N.A. | | 37.9 | N.A. |
| Moisture content | | 0.42 | N.A. | | 0.42 | N.A. |

TABLE 15b.8

Analytical results for batches manufactured with high viscosity carrier

| | | D001L/106 (Solutol HS15, semisolid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 693.47 | N.A. | N.A. | 693.47 | N.A. |
| | CV | 2.9 | | | 2.9 | |
| Content Uniformity | Complies | Complies | N.A. | N.A. | Complies | N.A. |
| | CV | 3.50 | | | 3.50 | |
| Assay (HPLC) | 95.0%-105.0% | 97.3 | 92.5 | 92.3 | 97.3 | 97.6 |
| Related substances (HPLC) | | | | | | |
| HP1 | ≤0.50% | 0.06 | 0.16 | 0.19 | 0.06 | 0.31 |
| BM1 Dimer | ≤0.20% | 0.37 | 0.04 | 0.19 | 0.37 | 0.14 |
| BM1EE | ≤0.50% | 0.11 | 0.1 | 0.1 | 0.11 | 0.13 |
| NP1 | ≤0.20% | 0.01 | 0.01 | 0.01 | 0.01 | 0.01 |
| Major Unknon impurity (RRT) | ≤0.10% | 0.34 (0.82) | 0.23 (0.70) | 0.25 | 0.34 (0.82) | 0.21 (0.25) |
| Total impurities | ≤1.50% | 1.11 | 0.64 | 0.98 | 1.11 | 1.08 |
| Dissolution Test | 80% in 30 mins | fail | pass | pass | fail | pass |
| (% 10 min) | Average (%) | 8.9 | 73.1 | 58.4 | 8.9 | 98.6 |
| | min (%)-max (%) | 3.6-12.2 | 50.0-98.1 | 6.1-101.1 | 3.6-12.2 | 95.4-103.8 |
| | RSD | 44.4 | 24.3 | 63.8 | 44.4 | 3.0 |
| (% 20 min) | Average (%) | 19.6 | 86.9 | 86.9 | 19.6 | 98.4 |
| | min (%)-max (%) | 13.2-23.6 | 69.0-98.6 | 54.9-102.9 | 13.2-23.6 | 95.2-105.4 |
| | RSD | 22.9 | 14.0 | 20.7 | 22.9 | 3.6 |

TABLE 15b.8-continued

Analytical results for batches manufactured with high viscosity carrier

| | | D001L/106 (Solutol HS15, semisolid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| (% 30 min) | Average (%) | 31.2 | 93.9 | 95.6 | 31.2 | 97.1 |
| | min (%)-max (%) | 22.3-37.1 | 83.5-99.7 | 83.0-102.7 | 22.3-37.1 | 94.1-105.7 |
| | RSD | 17.4 | 6.2 | 9.3 | 17.4 | 4.5 |
| FAST POINT (% 60 min) | Average (%) | N.A | N.A | N.A | N.A | N.A. |
| | min (%)-max (%) | | | | | |
| | RSD | | | | | |
| Moisture content | | 1.54 | 1.59 | 1.66 | 1.54 | 1.71 |

TABLE 15b.9

Analytical results for batches manufactured with high viscosity carrier

| | | D001L/107 (BRIJ C2, semisolid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 656.54 | N.A. | N.A. | 656.54 | N.A. |
| | CV | 3.1 | | | 3.1 | |
| Content Uniformity | Complies | Not Complies | N.A. | N.A. | Not Complies | N.A. |
| | CV | 17.13 | | | 17.13 | |
| Assay (HPLC) | 95.0%-105.0% | 86.9 | 37.1 | 74.1 | 86.9 | 82.0 |
| Related substances (HPLC) | | | | | | |
| HP1 | ≤0.50% | 0.04 | 0.08 | 0.01 | 0.04 | 0.12 |
| BM1 Dimer | ≤0.20% | 0.02 | 0.04 | 0.09 | 0.02 | 0.09 |
| BM1EE | ≤0.50% | 0.05 | 0.07 | 0 | 0.05 | 0.02 |
| NP1 | ≤0.20% | 0.01 | 0.01 | 0.03 | 0.01 | 0.00 |
| Major Unknon impurity (RRT) | ≤0.10% | 0.03 (0.70) | 0.09 (0.70) | 0.01 | 0.03 (0.70) | 0.02 (0.70) |
| Total impurities | ≤1.50% | 0.15 | 0.33 | 0.16 | 0.15 | 0.28 |
| Dissolution Test | 80% in 30 mins | fail | fail | fail | fail | fail |
| (% 10 min) | Average (%) | 0.7 | 0.1 | 0.1 | 0.7 | 0.0 |
| | min (%)-max (%) | 0.0-1.5 | 0.0-0.3 | 0.0-0.6 | 0.0-1.5 | 0.0-0.0 |
| | RSD | 66.9 | 244.9 | 244.9 | 66.9 | — |
| (% 20 min) | Average (%) | 3.2 | 1.1 | 1.2 | 3.2 | 1.8 |
| | min (%)-max (%) | 2.5-4.0 | 0.8-1.6 | 0.3-2.0 | 2.5-4.0 | 0.8-3.1 |
| | RSD | 21.3 | 29.9 | 61.1 | 21.3 | 47.7 |
| (% 30 min) | Average (%) | 4.9 | 2.5 | 2.4 | 4.9 | 3.3 |
| | min (%)-max (%) | 3.7-6.3 | 1.8-3.5 | 1.3-3.7 | 3.7-6.3 | 2.6-4.2 |
| | RSD | 23.9 | 23.9 | 41.3 | 23.9 | 20.6 |
| FAST POINT (% 60 min) | Average (%) | 15.1 | 6.3 | 5.7 | 15.1 | 9.5 |
| | min (%)-max (%) | 13.0-17.5 | 4.8-7.6 | 4.6-7.8 | 13.0-17.5 | 8.1-11.5 |
| | RSD | 12.2 | 14.6 | 24.9 | 12.2 | 12.7 |
| Moisture content | | 0.97 | 1.42 | 1.55 | 0.97 | 1.44 |

TABLE 15b.10

Analytical results for batches manufactured with high viscosity carrier

| | | D001L/108 (GELUCIRE 44/14, semisolid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 704.34 | N.A. | N.A. | 704.34 | N.A. |
| CV | | 2.7 | | | 2.7 | |
| Content Uniformity | Complies | Complies | N.A. | N.A. | Complies | N.A. |
| CV | | 3.66 | | | 3.66 | |
| Assay (HPLC) | 95.0%-105.0% | 92.9 | 89.3 | 93.1 | 92.9 | 92.2 |
| Related substances (HPLC) | | | | | | |
| HP1 | ≤0.50% | 0.16 | 0.15 | 0.16 | 0.16 | 0.53 |
| BM1 Dimer | ≤0.20% | 0.04 | 0.03 | 0.11 | 0.04 | 0.15 |
| BM1EE | ≤0.50% | 0.11 | 0.11 | 0.1 | 0.11 | 0.1 |
| NP1 | ≤0.20% | 0.01 | 0.01 | 0.01 | 0.01 | 0.01 |
| Major Unknon impurity (RRT) | ≤0.10% | 0.04 (0.70) | 0.02 (0.70) | Nd | 0.04 (0.70) | 0.08 (0.71) |
| Total impurities | ≤1.50% | 0.36 | 0.34 | 0.38 | 0.36 | 0.91 |
| Dissolution Test | 80% in 30 mins | fail | fail | fail | fail | fail |
| (% 10 min) | Average (%) | 18.1 | 10.5 | 10.5 | 18.1 | 15.4 |
| | min (%)-max (%) | 12.4-28.0 | 0.0-17.5 | 2.8-18.5 | 12.4-28.0 | 6.3-19.7 |
| | RSD | 34.5 | 61.3 | 56.7 | 34.5 | 31.2 |
| (% 20 min) | Average (%) | 51.8 | 33.6 | 37.2 | 51.8 | 47.4 |
| | min (%)-max (%) | 35.6-64.6 | 3.1-49.9 | 22.5-50.1 | 35.6-64.6 | 43.7-54.1 |
| | RSD | 20.2 | 49 | 30.9 | 20.2 | 8.6 |
| (% 30 min) | Average (%) | 74.4 | 48.2 | 62.6 | 74.4 | 68.4 |
| | min (%)-max (%) | 50.1-87.6 | 6.5-63.7 | 43.2-78.9 | 50.1-87.6 | 63.0-77.2 |
| | RSD | 19.3 | 44 | 20.0 | 19.3 | 7.6 |
| FAST POINT (% 60 min) | Average (%) | N.A. | 88.0 | 88.5 | N.A. | 83.8 |
| | min (%)-max (%) | | 79.8-93.5 | 70.9-96.6 | | 72.0-89.4 |
| | RSD | | 5.8 | 10.2 | | 8.5 |
| Moisture content | | 0.61 | 0.98 | 1.08 | 0.61 | 0.89 |

TABLE 15b.11

Analytical results for batches manufactured with high viscosity carrier

| | | D001L/109 (BRIJ L23, solid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 708.03 | N.A. | N.A. | 708.03 | N.A. |
| CV | | 2.9 | | | 2.9 | |
| Content Uniformity | Complies | Not Complies | N.A. | N.A. | Not Complies | N.A. |
| CV | | 11.90 | | | 11.90 | |
| Assay (HPLC) | 95.0%-105.0% | 99.2 | 95.7 | 100.1 | 99.2 | 99.9 |
| Related substances (HPLC) | | | | | | |
| HP1 | ≤0.50% | 0.16 | 0.14 | 0.01 | 0.16 | 0.26 |
| BM1 Dimer | ≤0.20% | 0.04 | 0.04 | 0.15 | 0.04 | 0.15 |
| BM1EE | ≤0.50% | 0.13 | 0.11 | 0.11 | 0.13 | 0.1 |
| NP1 | ≤0.20% | 0.01 | 0.01 | 0.17 | 0.01 | 0.01 |
| Major Unknon impurity (RRT) | ≤0.10% | 0.17 (0.70) | 0.19 (0.70) | 0.17 | 0.17 (0.70) | 0.50 (0.70) |
| Total impurities | ≤1.50% | 0.51 | 0.49 | 0.6 | 0.51 | 1.13 |
| Dissolution Test | 80% in 30 mins | pass | fail | fail | pass | pass |
| (% 10 min) | Average (%) | 17.4 | 2.0 | 0.3 | 17.4 | 10.6 |
| | min (%)-max (%) | 9.4-28.9 | 0.0-8.2 | 0.0-1.1 | 9.4-28.9 | 5.9-16.6 |
| | RSD | 47.2 | 162.0 | 144.1 | 47.2 | 36.4 |
| (% 20 min) | Average (%) | 64.0 | 30.4 | 5.4 | 64.0 | 40.1 |
| | min (%)-max (%) | 50.6-78.6 | 15.7-50.2 | 3.1-7.2 | 50.6-78.6 | 33.9-58.6 |
| | RSD | 18.3 | 40.6 | 30.6 | 18.3 | 23.2 |

TABLE 15b.11-continued

Analytical results for batches manufactured with high viscosity carrier

| | | D001L/109 (BRIJ L23, solid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| (% 30 min) | Average (%) | 96.3 | 61.8 | 12.7 | 96.3 | 80.8 |
| | min (%)-max (%) | 93.7-99.9 | 39.0-80.1 | 7.4-17.6 | 93.7-99.9 | 75.5-95.4 |
| | RSD | 4.4 | 25.3 | 27.8 | 4.4 | 9.0 |
| FAST POINT (% 60 min) | Average (%) | N.A. | 97.0 | 98.6 | N.A. | N.A. |
| | min (%)-max (%) | | 94.8-99.4 | 96.9-100.8 | | |
| | RSD | | 1.6 | 1.3 | | |
| Moisture content | | 1.40 | 1.67 | 1.91 | 1.40 | 1.54 |

TABLE 15b.12

Analytical results for batches manufactured with high viscosity carrier

| | | D001L/110 (BRIJ S20, solid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 684.64 | N.A. | N.A. | 684.64 | N.A. |
| | CV | 3.8 | | | 3.8 | |
| Content Uniformity | Complies | Not Complies | N.A. | N.A. | Not Complies | N.A. |
| | CV | 5.83 | | | 5.83 | |
| Assay (HPLC) | 95.0%-105.0% | 96.0 | 91.7 | 88.5 | 96.0 | 78.7 |
| Related substances (HPLC) | | | | | | |
| HP1 | ≤0.50% | 0.12 | 0.07 | 0.06 | 0.12 | 0.25 |
| BM1 Dimer | ≤0.20% | 0.03 | 0.03 | 0.12 | 0.03 | 0.16 |
| BM1EE | ≤0.50% | 0.09 | 0.07 | 0.05 | 0.09 | 0.1 |
| NP1 | ≤0.20% | 0.01 | 0.01 | 0.00 | 0.01 | 0.01 |
| Major Unknon impurity (RRT) | ≤0.10% | 0.14 (0.70) | 0.13 (0.70) | 0.10 | 0.14 (0.70) | 0.49 (RRT 0.25) |
| Total impurities | ≤1.50% | 0.46 | 0.33 | 0.39 | 0.46 | 1.14 |
| Dissolution Test | 80% in 30 mins | fail | fail | fail | fail | fail |
| (% 10 min) | Average (%) | 5.3 | 0.5 | 0.6 | 5.3 | 4.3 |
| | min (%)-max (%) | 2.8-7.7 | 0.0-1.5 | 0.3-1.2 | 2.8-7.7 | 2.4-7.0 |
| | RSD | 35.0 | 122.2 | 71.6 | 35.0 | 42.7 |
| (% 20 min) | Average (%) | 29.9 | 7.7 | 5.8 | 29.9 | 24.3 |
| | min (%)-max (%) | 27.1-33.0 | 4.2-10.3 | 3.5-7.4 | 27.1-33.0 | 20.5-27.6 |
| | RSD | 6.7 | 32.1 | 24.9 | 6.7 | 10.9 |
| (% 30 min) | Average (%) | 63.3 | 21.1 | 15.6 | 63.3 | 54.9 |
| | min (%)-max (%) | 57.1-69.2 | 12.0-28.4 | 13.1-18.7 | 57.1-69.2 | 50.1-63.2 |
| | RSD | 7.0 | 30.4 | 13.0 | 7.0 | 10.9 |
| FAST POINT (% 60 min) | Average (%) | 103.5 | 96.0 | 95.4 | 103.5 | 102.6 |
| | min (%)-max (%) | 95.9-111.2 | 92.8-107.6 | 88.0-102.5 | 95.9-111.2 | 96.9-114.1 |
| | RSD | 5.8 | 6.0 | 5.1 | 5.8 | 6.4 |
| Moisture content | | 1.06 | 1.39 | 1.48 | 1.06 | 1.30 |

TABLE 15b.13

Analytical results for batches manufactured with high viscosity carrier

| | | D001L/111 (BRIJ S721, solid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 693.16 | N.A. | N.A. | 693.16 | N.A. |
| | CV | 0.9 | | | 0.9 | |
| Content Uniformity | Complies | Not Complies | N.A. | N.A. | Not Complies | N.A. |
| | CV | 28.32 | | | 28.32 | |
| Assay (HPLC) | 95.0%-105.0% | 43.1 | 20.1 | | 43.1 | |
| Related substances (HPLC) | | | | | | |
| HP1 | ≤0.50% | 0.06 | 0.15 | | 0.06 | |
| BM1 Dimer | ≤0.20% | 0.11 | 0.04 | | 0.11 | |
| BM1EE | ≤0.50% | 0.09 | 0.08 | | 0.09 | |
| NP1 | ≤0.20% | 0.01 | 0.01 | | 0.01 | |
| Major Unknon impurity (RRT) | ≤0.10% | 0.14 (0.70) | 0.10 (0.70) | | 0.14 (0.70) | |
| Total impurities | ≤1.50% | 0.41 | 0.48 | | 0.41 | |
| Dissolution Test | 80% in 30 mins | fail | fail | fail | fail | fail |
| (% 10 min) | Average (%) | 1.7 | 0.1 | 0.0 | 1.7 | 1.5 |
| | min (%)-max (%) | 0.3-2.6 | 0.0-0.3 | 0.0-0.0 | 0.3-2.6 | 0.8-1.9 |
| | RSD | 64.7 | 89.5 | — | 64.7 | 28.2 |
| (% 20 min) | Average (%) | 4.9 | 1.5 | 0.6 | 4.9 | 4.7 |
| | min (%)-max (%) | 4.0-5.8 | 0.9-2.2 | 0.3-1.2 | 4.0-5.8 | 3.5-5.9 |
| | RSD | 12.9 | 29.3 | 49.9 | 12.9 | 16.3 |
| (% 30 min) | Average (%) | 7.5 | 3.1 | 2.4 | 7.5 | 8.1 |
| | min (%)-max (%) | 6.1-9.2 | 2.6-4.6 | 1.3-3.4 | 6.1-9.2 | 5.8-9.8 |
| | RSD | 16.1 | 24.9 | 35.1 | 16.1 | 18.5 |
| FAST POINT (% 60 min) | Average (%) | 33.8 | 22.8 | 17.7 | 33.8 | 35.0 |
| | min (%)-max (%) | 31.2-37.6 | 19.2-26.7 | 12.2-26.8 | 31.2-37.6 | 25.8-41.9 |
| | RSD | 11.9 | 12.1 | 30.6 | 11.9 | 16.0 |
| Moisture content | | 0.70 | 0.76 | | 0.70 | |

TABLE 15b.14

Analytical results for batches manufactured with high viscosity carrier

| | | D001L/112 (BRIJ S10, solid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 688.07 | N.A. | N.A. | 688.07 | N.A. |
| | CV | 1.5 | | | 1.5 | |
| Content Uniformity | Complies | Not Complies | N.A. | N.A. | Not Complies | N.A. |
| | CV | 17.32 | | | 17.32 | |
| Assay (HPLC) | 95.0%-105.0% | 65.1 | 82.0 | | 65.1 | |
| Related substances (HPLC) | | | | | | |
| HP1 | ≤0.50% | 0.20 | 0.46 | | 0.20 | |
| BM1 Dimer | ≤0.20% | 0.03 | 0.04 | | 0.03 | |
| BM1EE | ≤0.50% | 0.07 | 0.09 | | 0.07 | |
| NP1 | ≤0.20% | 0.01 | 0.01 | | 0.01 | |
| Major Unknon impurity (RRT) | ≤0.10% | 0.08 (0.70) | 0.15 (0.70) | | 0.08 (0.70) | |
| Total impurities | ≤1.50% | 0.41 | 0.90 | | 0.41 | |
| Dissolution Test | 80% in 30 mins | fail | fail | | fail | fail |
| (% 10 min) | Average (%) | 1.8 | 0.0 | 1.3 | 1.8 | 0.5 |
| | min (%)-max (%) | 0.9-3.2 | 0.0-0.0 | 0.9-1.9 | 0.9-3.2 | 0.0-1.1 |
| | RSD | 48.4 | 0.0 | 28.3 | 48.4 | 82.6 |
| (% 20 min) | Average (%) | 7.1 | 8.3 | 10.4 | 7.1 | 5.8 |
| | min (%)-max (%) | 6.5-9.1 | 7.1-10.3 | 8.9-14.7 | 6.5-9.1 | 4.9-5.6 |
| | RSD | 13.8 | 13.4 | 21.2 | 13.8 | 12.5 |

TABLE 15b.14-continued

Analytical results for batches manufactured with high viscosity carrier

| | | D001L/112 (BRIJ S10, solid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| (% 30 min) | Average (%) | 12.5 | 20.7 | 23.9 | 12.5 | 10.7 |
| | min (%)-max (%) | 11.3-14.6 | 16.0-29.4 | 20.2-29.0 | 11.3-14.6 | 9.3-12.1 |
| | RSD | 9.1 | 22.8 | 15.1 | 9.1 | 9.7 |
| FAST POINT (% 60 min) | Average (%) | 46.7 | 77.1 | 78.8 | 46.7 | 35.9 |
| | min (%)-max (%) | 43.1-49.6 | 84.5-74.1 | 58.8-86.8 | 43.1-49.6 | 31.6-39.4 |
| | RSD | 5.3 | 5.0 | 13.0 | 5.3 | 8.0 |
| Moisture content | | 0.70 | 0.99 | | 0.70 | |

TABLE 15b.15

Analytical results for batches manufactured with high viscosity carrier

| | | D001L/113 (MIRJ S40, solid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 703.91 | N.A. | N.A. | 703.91 | N.A. |
| | CV | 2.0 | | | 2.0 | |
| Content Uniformity | Complies | Not Complies | N.A. | N.A. | Not Complies | N.A. |
| | CV | 11.97 | | | 11.97 | |
| Assay (HPLC) | 95.0%-105.0% | 102.3 | 98.3 | | 102.3 | |
| Related substances (HPLC) | | | | | | |
| HP1 | ≤0.50% | 0.41 | 0.21 | | 0.41 | |
| BM1 Dimer | ≤0.20% | 0.06 | 0.10 | | 0.06 | |
| BM1EE | ≤0.50% | 0.12 | 0.12 | | 0.12 | |
| NP1 | ≤0.20% | 0.01 | 0.02 | | 0.01 | |
| Major Unknon impurity (RRT) | ≤0.10% | 0.16 (0.70) | 0.13 (0.70) | | 0.16 (0.70) | |
| Total impurities | ≤1.50% | 0.81 | 0.63 | | 0.81 | |
| Dissolution Test | 80% in 30 mins | pass | fail | | pass | fail |
| (% 10 min) | Average (%) | 18.6 | 1.7 | | 18.6 | 5.2 |
| | min (%)-max (%) | 11.4-24.2 | 0.6 | | 11.4-24.2 | 2.9-7.7 |
| | RSD | 30.3 | 83.0 | | 30.3 | 30.9 |
| (% 20 min) | Average (%) | 53.1 | 7.6 | | 53.1 | 14.7 |
| | min (%)-max (%) | 45.1-60.3 | 4.5-11.5 | | 45.1-60.3 | 10.2-17.0 |
| | RSD | 10.9 | 35.3 | | 10.9 | 29.3 |
| (% 30 min) | Average (%) | 80.1 | 18.1 | | 80.1 | 25.4 |
| | min (%)-max (%) | 72.2-83.9 | 10.1-26.7 | | 72.2-83.9 | 18.0-34.2 |
| | RSD | 5.9 | 37.8 | | 5.9 | 21.9 |
| FAST POINT (% 60 min) | Average (%) | N.A. | 92.0 | | N.A. | 100.5 |
| | min (%)-max (%) | | 89.0-95.4 | | | 98.6-106.3 |
| | RSD | | 2.6 | | | 3.0 |
| Moisture content | | 0.44 | 0.64 | | 0.44 | |

TABLE 15b.16

Analytical results for batches manufactured with high viscosity carrier

| | | D001L/115 (MIRJ S8, semisolid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 681.14 | N.A. | N.A. | 681.14 | N.A. |
| | CV | 2.6 | | | 2.6 | |
| Content Uniformity | Complies | Not Complies | N.A. | N.A. | Not Complies | N.A. |
| | CV | 13.04 | | | 13.04 | |
| Assay (HPLC) | 95.0%-105.0% | 97.6 | 90.2 | | 97.6 | |
| Related substances (HPLC) | | | | | | |
| HP1 | ≤0.50% | 0.13 | 0.28 | | 0.13 | |
| BM1 Dimer | ≤0.20% | 0.03 | 0.06 | | 0.03 | |
| BM1EE | ≤0.50% | 0.11 | 0.11 | | 0.11 | |
| NP1 | ≤0.20% | 0.01 | 0.01 | | 0.01 | |
| Major Unknon impurity (RRT) | ≤0.10% | 0.05 (0.70) | 0.17 (0.70) | | 0.05 (0.70) | |
| Total impurities | ≤1.50% | 0.33 | 0.63 | | 0.33 | |
| Dissolution Test | 80% in 30 mins | fail | fail | | fail | fail |
| (% 10 min) | Average (%) | 4.5 | 2.3 | | 4.5 | 3.8 |
| | min (%)-max (%) | 3.3-5.3 | 0.0 | | 3.3-5.3 | 2.6-4.5 |
| | RSD | 17.7 | 155.9 | | 17.7 | 17.8 |
| (% 20 min) | Average (%) | 8.8 | 4.2 | | 8.8 | 7.9 |
| | min (%)-max (%) | 7.5-10.2 | 1.6-12.1 | | 7.5-10.2 | 7.3-10.2 |
| | RSD | 13.4 | 97.5 | | 13.4 | 14.3 |
| (% 30 min) | Average (%) | 11.1 | 5.7 | | 11.1 | 10.9 |
| | min (%)-max (%) | 8.7-12.3 | 2.3-14.0 | | 8.7-12.3 | 9.7-14.7 |
| | RSD | 12.2 | 77.0 | | 12.2 | 17.2 |
| FAST POINT (% 60 min) | Average (%) | 19.8 | 11.3 | | 19.8 | 21.2 |
| | min (%)-max (%) | 15.8-22.5 | 8.2-19.4 | | 15.8-22.5 | 17.6-26.4 |
| | RSD | 12.8 | 37.9 | | 12.8 | 14.9 |
| Moisture content | | 0.79 | 1.17 | | 0.79 | |

TABLE 15b.17

Analytical results for batches manufactured with high viscosity carrier

| | | D001L/116 (TWEEN 65, semisolid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 690.64 | N.A. | N.A. | 690.64 | N.A. |
| | CV | 1.2 | | | 1.2 | |
| Content Uniformity | Complies | Not Complies | N.A. | N.A. | Not Complies | N.A. |
| | CV | 36.97 | | | 36.97 | |
| Assay (HPLC) | 95.0%-105.0% | 94.7 | 81.5 | | 94.7 | |
| Related substances (HPLC) | | | | | | |
| HP1 | ≤0.50% | 0.08 | 0.10 | | 0.08 | |
| BM1 Dimer | ≤0.20% | 0.03 | 0.05 | | 0.03 | |
| BM1EE | ≤0.50% | 0.09 | 0.08 | | 0.09 | |
| NP1 | ≤0.20% | 0.01 | 0.01 | | 0.01 | |
| Major Unknon impurity (RRT) | ≤0.10% | 0.06 (0.70) | 0.11 (0.70) | | 0.06 (0.70) | |
| Total impurities | ≤1.50% | 0.29 | 0.37 | | 0.29 | |
| Dissolution Test | 80% in 30 mins | fail | fail | | fail | fail |
| (% 10 min) | Average (%) | 2.6 | 1.4 | | 2.6 | 2.4 |
| | min (%)-max (%) | 1.0-5.4 | 0.0 | | 1.0-5.4 | 0.7-4.0 |
| | RSD | 60.7 | 88.4 | | 60.7 | 49.1 |
| (% 20 min) | Average (%) | 8.5 | 4.2 | | 8.5 | 5.4 |
| | min (%)-max (%) | 4.4-11.4 | 2.7-5.6 | | 4.4-11.4 | 3.2-7.8 |
| | RSD | 30.5 | 29.0 | | 30.5 | 31.9 |

TABLE 15b.17-continued

Analytical results for batches manufactured with high viscosity carrier

| | | D001L/116 (TWEEN 65, semisolid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| (% 30 min) | Average (%) | 12.3 | 6.1 | | 12.3 | 8.3 |
| | min (%)-max (%) | 9.9-15.5 | 4.3-7.9 | | 9.9-15.5 | 5.6-10.6 |
| | RSD | 20.2 | 23.5 | | 20.2 | 26.0 |
| FAST POINT (% 60 min) | Average (%) | 17.3 | 11.9 | | 17.3 | 15.5 |
| | min (%)-max (%) | 11.0-25.1 | 8.6-15.5 | | 11.0-25.1 | 10.5-20.7 |
| | RSD | 30.0 | 21.7 | | 30.0 | 25.0 |
| Moisture content | | 2.47 | 0.85 | | 2.47 | |

TABLE 15b.18

Analytical results for batches manufactured with high viscosity carrier

| | | D001L/117 (SPEZIOL TPGS, semisolid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 702.63 | N.A. | N.A. | 702.63 | N.A. |
| | CV | 2.1 | | | 2.1 | |
| Content Uniformity | Complies | Not Complies | N.A. | N.A. | Not Complies | N.A. |
| | CV | 21.62 | | | 21.62 | |
| Assay (HPLC) | 95.0%-105.0% | 98.5 | 100.0 | | 98.5 | |
| Related substances (HPLC) | | | | | | |
| HP1 | ≤0.50% | 0.1 | 0.12 | | 0.1 | |
| BM1 Dimer | ≤0.20% | 0.19 | 0.15 | | 0.19 | |
| BM1EE | ≤0.50% | 0.07 | 0.11 | | 0.07 | |
| NP1 | ≤0.20% | 0.01 | 0.01 | | 0.01 | |
| Major Unknon impurity (RRT) | ≤0.10% | nd | nd | | nd | |
| Total impurities | ≤1.50% | 0.37 | 0.39 | | 0.37 | |
| Dissolution Test | 80% in 30 mins | fail | fail | | fail | |
| (% 10 min) | Average (%) | 4.5 | 12.6 | | 4.5 | |
| | min (%)-max (%) | 2.7-7.1 | 6-22.1 | | 2.7-7.1 | |
| | RSD | 36.3 | 57.3 | | 36.3 | |
| (% 20 min) | Average (%) | 19.4 | 55.5 | | 19.4 | |
| | min (%)-max (%) | 16.7-22.7 | 35.2-80.8 | | 16.7-22.7 | |
| | RSD | 13.7 | 39.4 | | 13.7 | |
| (% 30 min) | Average (%) | 42.3 | 101.5 | | 42.3 | |
| | min (%)-max (%) | 36.6-47.5 | 72.5-128.4 | | 36.6-47.5 | |
| | RSD | 9.7 | 22.1 | | 9.7 | |
| FAST POINT (% 60 min) | Average (%) | 99.8 | N.A. | | 99.8 | |
| | min (%)-max (%) | 96.6-105.2 | | | 96.6-105.2 | |
| | RSD | 3.1 | | | 3.1 | |
| Moisture content | | 0.76 | 0.91 | | 0.76 | |

TABLE 15b.19

Analytical results for batches manufactured with high viscosity carrier

| | | D001L/118 (TWEEN 61, semisolid) | | | | |
| --- | --- | --- | --- | --- | --- | --- |
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 655.01 | N.A. | N.A. | 655.01 | N.A. |
| | CV | 4.9 | | | 4.9 | |
| Content Uniformity | Complies | Not Complies | N.A. | N.A. | Not Complies | N.A. |
| | CV | 22.02 | | | 22.02 | |
| Assay (HPLC) | 95.0%-105.0% | 11.4 | 6.0 | | 11.4 | |
| Related substances (HPLC) | | | | | | |
| HP1 | ≤0.50% | 0.08 | 0.10 | | 0.08 | |
| BM1 Dimer | ≤0.20% | 0.23 | 0.39 | | 0.23 | |
| BM1EE | ≤0.50% | 0.03 | 0.05 | | 0.03 | |
| NP1 | ≤0.20% | 0.03 | 0.00 | | 0.03 | |
| Major Unknon impurity (RRT) | ≤0.10% | 0.02 | 0.19 | | 0.02 | |
| Total impurities | ≤1.50% | 0.40 | 0.74 | | 0.40 | |
| Dissolution Test | 80% in 30 mins | fail | fail | | fail | |
| (% 10 min) | Average (%) | 0.0 | 0.0 | | 0.0 | |
| | min (%)-max (%) | 0.0-0.2 | 0.0-0.2 | | 0.0-0.2 | |
| | RSD | 244.9 | 244.9 | | 244.9 | |
| (% 20 min) | Average (%) | 0.9 | 1.1 | | 0.9 | |
| | min (%)-max (%) | 0.0-1.6 | 0.2-1.7 | | 0.0-1.6 | |
| | RSD | 63.7 | 47.8 | | 63.7 | |
| (% 30 min) | Average (%) | 1.7 | 2.2 | | 1.7 | |
| | min (%)-max (%) | 0.6-2.7 | 1.2-3 | | 0.6-2.7 | |
| | RSD | 45.2 | 29.4 | | 45.2 | |
| FAST POINT (% 60 min) | Average (%) | 3.7 | 6.3 | | 3.7 | |
| | min (%)-max (%) | 1.9-6.2 | 6.0-8.1 | | 1.9-6.2 | |
| | RSD | 39.3 | 15.1 | | 39.3 | |
| Moisture content | | 0.86 | 1.75 | | 0.86 | |

TABLE 15b.20

Analytical results for batches manufactured with high viscosity carrier

| | | D001L/120 (MIRJ S100, semisolid) | | | | |
| --- | --- | --- | --- | --- | --- | --- |
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 711.95 | N.A. | N.A. | 711.95 | N.A. |
| | CV | 0.8 | | | 0.8 | |
| Content Uniformity | Complies | Not Complies | N.A. | N.A. | Not Complies | N.A. |
| | CV | 12.33 | | | 12.33 | |
| Assay (HPLC) | 95.0%-105.0% | 97.2 | 96.0 | | 97.2 | |
| Related substances (HPLC) | | | | | | |
| HP1 | ≤0.50% | 0.06 | 0.07 | | 0.06 | |
| BM1 Dimer | ≤0.20% | 0.03 | 0.11 | | 0.03 | |
| BM1EE | ≤0.50% | 0.07 | 0.08 | | 0.07 | |
| NP1 | ≤0.20% | 0.02 | 0.01 | | 0.02 | |
| Major Unknon impurity (RRT) | ≤0.10% | 0.03 | 0.05 | | 0.03 | |
| Total impurities | ≤1.50% | 0.21 | 0.38 | | 0.21 | |
| Dissolution Test | 80% in 30 mins | fail | fail | | fail | |
| (% 10 min) | Average (%) | 16.9 | 0.6 | | 16.9 | |
| | min (%)-max (%) | 7.9-21.3 | 0.0-1.3 | | 7.9-21.3 | |
| | RSD | 29.6 | 94.9 | | 29.6 | |
| (% 20 min) | Average (%) | 47.8 | 7.0 | | 47.8 | |
| | min (%)-max (%) | 33.5-53.2 | 3.6-10.8 | | 33.5-53.2 | |
| | RSD | 15.2 | 34.4 | | 15.2 | |

TABLE 15b.20-continued

Analytical results for batches manufactured with high viscosity carrier

| | | D001L/120 (MIRJ S100, semisolid) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| (% 30 min) | Average (%) | 70.0 | 19.8 | | 70.0 | |
| | min (%)-max (%) | 50.2-79.3 | 11.3-29.3 | | 50.2-79.3 | |
| | RSD | 16.5 | 35.7 | | 16.5 | |
| FAST POINT (% 60 min) | Average (%) | 102.3 | 97.1 | | 102.3 | |
| | min (%)-max (%) | 96.7-123.5 | 89.7-105.1 | | 96.7-123.5 | |
| | RSD | 10.4 | 6.4 | | 10.4 | |
| Moisture content | | 0.55 | 0.69 | | 0.55 | |

TABLE 15b.21

Analytical results for batches manufactured without carrier (Active ingredient (API) only)

| | | D001L/114 (API) | | | | |
|---|---|---|---|---|---|---|
| | | Storage conditions: 40° C.-75% RH | | | Storage conditions: 25° C.-60% RH | |
| Analytical Test | Limits | 0 | 1 month | 3 months | 0 | 3 months |
| Identification (HPLC) | Positive | Positive | Positive | Positive | Positive | Positive |
| Mean Weight (mg/cps) | 685-725 | 146.82 | N.A. | N.A. | 146.82 | N.A. |
| | CV | 3.1 | | | 3.1 | |
| Content Uniformity | Complies | Not Complies(WV) | N.A. | N.A. | Not Complies(WV) | N.A. |
| | CV | 6.42 | | | 6.42 | |
| Assay (HPLC) | 95.0%-105.0% | 97.4 | 93.6 | | 97.4 | |
| Related substances (HPLC) | | | | | | |
| HP1 | ≤0.50% | 0.12 | 0.05 | | 0.12 | |
| BM1 Dimer | ≤0.20% | 0.03 | 0.03 | | 0.03 | |
| BM1EE | ≤0.50% | 0.11 | 0.11 | | 0.11 | |
| NP1 | ≤0.20% | 0.01 | 0.01 | | 0.01 | |
| Major Unknon impurity (RRT) | ≤0.10% | nd | nd | | nd | |
| Total impurities | ≤1.50% | 0.27 | 0.20 | | 0.27 | |
| Dissolution Test | 80% in 30 mins | pass | pass | | pass | |
| (% 10 min) | Average (%) | 101.1 | 103.7 | | 101.1 | |
| | min (%)-max (%) | 53.9-121.7 | 91.2 | | 53.9-121.7 | |
| | RSD | 25.1 | 6.6 | | 25.1 | |
| (% 20 min) | Average (%) | 113.3 | 105.5 | | 113.3 | |
| | min (%)-max (%) | 105.1-116.8 | 101.8-110.1 | | 105.1-116.8 | |
| | RSD | 3.7 | 2.9 | | 3.7 | |
| (% 30 min) | Average (%) | 113.0 | 103.9 | | 113.0 | |
| | min (%)-max (%) | 105.2-119.3 | 100.7-108.5 | | 105.2-119.3 | |
| | RSD | 4.2 | 2.9 | | 4.2 | |
| FAST POINT (% 60 min) | Average (%) | N.A. | N.A | | N.A. | |
| | min (%)-max (%) | | | | | |
| | RSD | | | | | |
| Moisture content | | N.A | | | | |

Batches Manufactured with Modified Bendamustine Hydrochloride/Carrier Ratio

Two different bendamustine hydrochloride/Carrier ratios were investigated with two different carriers, in order to evaluate the effect of the bendamustine hydrochloride concentration in the suspension on the final product stability.

MIGLYOL 812 and SOFTISAN 649, having a low and high viscosity respectively were selected as suitable for this study. The formulation with MIGLYOL 812 included AEROSIL as a viscosity modifier, to ensure the physical stability of the suspension.

The composition of the bendamustine hydrochloride containing LFHC batches and their corresponding analytical results at time zero, is reported in Tables 16a and b.

TABLE 16a

Batches manufactured with modified API/Carrier ratio

| | Batch No | | | |
|---|---|---|---|---|
| Components | D001L/070 % | D001L/071 % | D001L/07 % | D001L/073 % |
| MIGLYOL 812 | 85.0 | — | — | 80.7 |
| SOFTISAN 649 | — | 87.5 | 83.5 | — |
| Bendamustine HCl | 11.9 | 12.5 | 16.5 | 16.2 |

TABLE 16a-continued

Batches manufactured with modified API/Carrier ratio

| Components | Batch No | | | |
|---|---|---|---|---|
| | D001L/070 % | D001L/071 % | D001L/07 % | D001L/073 % |
| AEROSIL | 3.1 | — | — | 3.1 |
| API/Carrier ratio | 14 | 14 | 20 | 20 |

Batches No. D001L/070 and 073 were manufactured by adding bendamustine hydrochloride to the carrier, followed by homogenization and subsequently adding to this mixture the minimum suitable amount of the viscosity increasing agent to obtain a viscous liquid suspension, which was hand-filled into the LICAPS capsules.

The API/Carrier ratio was established first, regardless of the final amount of the suspension. The viscosity increaser was only useful to suspend the amount of API added. Batches No. D001L/071 and 072 were manufactured by adding the bendamustine hydrochloride to the melted carrier, homogenizing the mixture and filling it into the LICAPS capsules with the Capsule Filling and Sealing machine CFS1200. The bendamustine hydrochloride/Carrier ratio was established first, regardless of the final amount of the suspension.

TABLE 16b

Analytical results for batches manufactured with modified API/Carrier ratio

| Analytical Test | Limits | Results of analytical Tests performed on LFHC | | | |
|---|---|---|---|---|---|
| | | D001L/070 | D001L/071 | D001L/072 | D001L/073 |
| Identification (HPLC) | Positive | Positive | Positive | Positive | Positive |
| Content Uniformity | Complies | Complies | Not Complies | Not Complies | Not Complies |
| Assay (HPLC) | 95.0%-105.0% | 113.5 | 92.2 | 99.4 | 116.6 |
| Related substances (HPLC) | | | | | |
| HP1 | ≤0.50% | 0.10 | 0.14 | 0.11 | 0.17 |
| BM1 Dimer | ≤0.20% | 0.04 | 0.05 | 0.05 | 0.05 |
| BM1EE | ≤0.50% | 0.15 | 0.15 | 0.15 | 0.17 |
| NP1 | ≤0.20% | 0.01 | 0.01 | 0.01 | 0.01 |
| Ind. Unknown impurity | ≤0.10% | n.d. | n.d. | n.d. | n.d. |
| Total impurities | ≤1.50% | 0.30 | 0.35* | 0.32* | 0.40 |
| Dissolution Test (Medium: buffer pH = 1.5) | | | | | |
| (% 10 min) | 80% in 30 min | 11.6 | 14.7 | 12.2 | 18.5 |
| (% 20 min) | | 30.4 | 20.5 | 15.9 | 30.8 |
| (% 30 min) | | 37.7 | 22.9 | 17.4 | 44.6 |

*Values calculated vs API area

Batches Manufactured with Aged Carriers
Carrier Aging Procedure

LABRAFIL M1944 CS and PLURONIC L44 NF INH were placed in open transparent glass bottles and exposed for about 5 days to:
  Artificial light
  Atmospheric oxygen
  Compressed air flow on their surface Active Batches Manufacturing The aged LABRAFIL M1944 CS and PLURONIC L44 NF INH were used in the preparation of formulations containing bendamustine hydrochloride (batches D001L/074 and D001L/079 in table 17a). The batches were manufactured by adding the bendamustine hydrochloride to the aged carrier, followed by homogenization. Thanks to their suitable viscosity, all suspensions could be filled into LICAPS capsules with the Capsule Filling and Sealing machine CFS 1200.

TABLE 17a

Batches manufactured with aged carriers

| Components | Batch No | |
|---|---|---|
| | D001L/074 % | D001L/079 % |
| LABRAFIL M1944 CS | 90.8 | — |
| PLURONIC L44 INH NF | — | 90.8 |
| Bendamustine HCl | 9.2 | 9.2 |

The analytical results at time zero are reported in table 17b.

TABLE 17b

Analytical results for batches manufactured with aged carriers

| Analytical Test | Limits | Results of analytical Tests performed on LFHC | |
|---|---|---|---|
| | | D001L/074 | D001L/079 |
| Identification (HPLC) | Positive | Positive | Positive |
| Content Uniformity | Complies | Complies | Complies |
| Assay (HPLC) | 95.0%–105.0% | 95.8 | 101.5 |
| Related substances (HPLC) | | | |
| HP1 | ≤0.50% | 0.11 | 0.09 |
| BM1 Dimer | ≤0.20% | 0.04 | 0.04 |
| BM1EE | ≤0.50% | 0.15 | 0.15 |
| NP1 | ≤0.20% | 0.01 | 0.01 |
| Ind. Unknown impurity | ≤0.10% | 0.02 | 0.02 |
| Total impurities | ≤1.50% | 0.33 | 0.31 |
| Dissolution Test (Medium: buffer pH = 1.5) | | | |
| (% 10 min) | 80% in 30 min | 66.9 | 96.6 |
| (% 20 min) | | 94.3 | 98.8 |
| (% 30 min) | | 92.3 | 96.7 |

Batches Manufactured with Carriers with Modified Moisture Content
Rationale for the Selection of the Carriers For the moisture content study, the selection of carriers was performed according to their water sorption/desorption profiles. In order to evaluate the effect of water uptake by the carrier on the stability of bendamustine hydrochloride, the carriers were selected amongst the ones that showed more hygroscopicity.

To this end studies were undertaken using a Dynamic Vapour Sorption apparatus from Surface Measurement Systems. The apparatus consists of a Cahn microbalance housed inside a temperature controlled cabinet. Experimental conditions were:
Temperature: 25° C.
Start RH: 10%
Start size: 10%
Next step conditions: dm/dt (%/min)<0.002% or after 360 minutes
Max RH: 80%
Method: Full cycle (from 10% RH to 80% RH back to 10%)
Purge gas: Nitrogen
Flow rate gas: 200 ml/min.

The excipients, after investigation, could be classified into 3 categories:
Low hygroscopicity: sorption≤1% at 80% RH
Medium hygroscopicity: sorption>1% and ≤5% at 80% RH and
High hygroscopicity: sorption>5% at 80% RH.
For the results see Table 18.

TABLE 18 excipients and their water sorption (%) at 80% RH

| Excipients with low hygroscopic properties | |
|---|---|
| MIGLYOL812 | 0.20 |
| MIGLYOL 810 | 0.18 |
| MIGLYOL 829 | 0.31 |
| MIGLYOL 840 | 0.22 |
| LABRAFAC PG | 0.19 |
| LAUROGLYCOL FCC | 0.86 |
| SOFTISAN 649 | 0.37 |
| Excipients with medium hygroscopic properties | |
| CREMOPHOR A25 | 4.07 |
| SOFTIGEN 701 | 2.35 |
| LABRAFIL M2125 CS | 1.13 |
| PLUROL Oléique CC 497 | 4.40 |
| LABRAFIL M1944 CS | 1.25 |
| GELUCIRE 44/14 | 2.48 |
| LAUROGLYCOL 90 | 1.89 |
| MYRJ S40 | 2.7 |
| PLURONIC F108 | 1.3 |
| MYRJ S100 | 2.8 |
| Excipients with high hygroscopic properties | |
| CREMOPHOR RH 40 | 19.88 |
| CREMOPHOR A6 | 8.80 |
| CREMOPHOR EL | 13.46 |
| PLURONIC L44 NF INH | 11.0 |
| TWEEN 20 | 22.9 |
| TWEEN 81 NV LQ (CQ) | 9.6 |
| SOLUTOL HS 15 | 21.9 |
| SPEZIOL TPGS Pharma | 16.4 |
| BRIJ S20-PW-(MV) | 8.1 |
| BRIJ L23-PA-(MV) | 16.3 |
| SYNPERONIC PE/L64 | 10.1 |
| BRIJ O20-SS | 19.6 |
| BRIJ O10-SS | 15.5 |
| BRIJ S10 | 13.7 |
| BRIJ C2 | 7.2 |
| BRIJ S721-SO | 7.4 |
| MYRJ S8-SS | 14.5 |
| BRIJ L4 | 10.8 |
| GLYCEROX HE | 17.1 |
| TWEEN 65 | 7.1 |
| PLURONIC P85 | 10.4 |
| PLURONIC P105 | 15.0 |
| PLURONIC P103 | 9.4 |
| PLURONIC L35 | 13.8 |
| PLURONIC L43 | 8.9 |
| TWEEN 61 | 9.8 |
| TWEEN 40 | 21.5 |

CREMOPHOR A6 and PLURONIC L44 NF INH were considered to be the most suitable carriers for this purpose.

For TRANSCUTOL HP no moisture sorption could be assessed because it evaporated at 25° C.

Moisture Content Increasing Procedure

A sample of each carrier was dispensed in open glass beakers and kept under the following conditions:
25° C./75% RH
25° C./100% RH in order to obtain two different moisture levels per carrier.

The first condition was achieved in a climatic chamber; the second one in a vacuum desiccator with the space under the platform filled with distilled water. The samples were stored in static conditions, without stirring.

After two days of storage, the carriers reached the following humidity values, measured by Karl Fischer titration (Table 19):

TABLE 19

Moisture content values (Karl Fischer)

| Carrier | Physical state in the described conditions | Moisture content (as is) | Moisture content after 2 days at 25 C./75% RH | Moisture content after 2 days at 25 C./100% RH |
|---|---|---|---|---|
| Cremophor A6 | Semisolid | 1.80% | 3.68% | 8.74% |
| PLURONIC L44 | Liquid | 0.08% | 2.08% | 2.71% |

Active Batches Manufacturing

CREMOPHOR A6 and PLURONIC L44 NF INH with the moisture content modified as described above, were used in the preparation of batches containing bendamustine hydrochloride (D001L/075 and D001L/076 for CREMOPHOR and D001L/080 and D001L/081 for PLURONIC).

All suspensions could be filled into LICAPS capsules with the Capsule Filling and Sealing machine CFS 1200. However, because of its semisolid physical status at 25° C., CREMOPHOR A6 had to be heated to 50° C. prior to using it in the suspensions preparation. The batches containing CREMOPHOR A6 were manufactured by adding bendamustine hydrochloride to the melted carrier, followed by homogenization and filling of the batch at an elevated temperature (about 55° C.) into the LICAPS capsules.

The batches containing PLURONIC L44 INH NF were manufactured by adding bendamustine hydrochloride to the carrier, followed by homogenization and filling into LICAPS capsules. The composition of all batches and the corresponding analytical results at time zero are reported in table 20a and b.

TABLE 20a

Batches manufactured with carriers with modified moisture content

| | Batch No | | | |
|---|---|---|---|---|
| Components | D001L/075* % | D001L/076* % | D001L/080* % | D001L/081* % |
| CREMOPHOR A6 | 90.8 | 90.8 | — | — |
| PLURONIC L44 NF INH | — | — | 90.8 | 90.8 |
| Bendamustine HCl | 9.2 | 9.2 | 9.2 | 9.2 |

*Carrier with modified moisture content (MC):
D001L/075: Cremophor A6 MC = 8.74%
D001L/080: Pluronic L44 MC = 2.08%
D001L/076: Cremophor A6 MC = 3.68%
D001L/081: Pluronic L44 MC = 2.71%

TABLE 20b

Analytical results for batches manufactured with carriers with modified moisture content

| | | Results of analytical Tests performed on LFHC | | | |
|---|---|---|---|---|---|
| Analytical Test | Limits | D001L/075 | D001L/076 | D001L/080 | D001L/081 |
| Identification (HPLC) | Positive | Positive | Positive | Positive | Positive |
| Content Uniformity | Complies | Complies | Not Complies | Not Complies | Complies | Complies |
| Assay (HPLC) | 95.0%-105.0% | 15.0 | 61.4 | 102.5 | 103.5 |
| Related substances (HPLC) | | | | | |
| HP1 | ≤0.50% | 0.39 | 0.12 | 0.08 | 0.05 |
| BM1 Dimer | ≤0.20% | 0.03 | 0.04 | 0.04 | 0.04 |
| BM1EE | ≤0.50% | 0.15 | 0.14 | 0.14 | 0.14 |
| NP1 | ≤0.20% | n.d. | 0.01 | 0.01 | 0.01 |
| Ind. Unknown impurity | ≤0.10% | 0.12 | 0.02 | 0.02 | 0.02 |
| Total impurities | ≤1.50% | 0.69 | 0.34 | 0.29 | 0.26 |
| Dissolution Test (Medium: buffer pH = 1.5) | | | | | |
| (% 10 min) | 80% in 30 min | 1.0 | 1.2 | 85.6 | 84.6 |
| (% 20 min) | | 1.7 | 2.7 | 94.4 | 92.6 |
| (% 30 min) | | 2.1 | 3.2 | 93.2 | 92.6 |

Bendamustine Hydrochloride Solubility in Carriers

In table 21.a below, the results of the analysis are reported expressed as mg of bendamustine hydrochloride completely dissolved in about 1 g of solution of the carrier selected.

TABLE 21.a

Results of bendamustine hydrochloride solubility in carriers

| Carrier | Physical state at room temperature | Suspension weight (mg) | API recovered (mg) | % API |
|---|---|---|---|---|
| LAUROGLYCOL 90 | Liquid | 993.9 | 0.61 | 0.06 |
| LAUROGLYCOL FCC | Liquid | 1934.8 | 0.33 | 0.02 |
| TRANSCUTOL HP | Liquid | 1003.1 | 10.01 | 1.00 |
| PLUROL oleique CC497 | Liquid | 1005.8 | 2.12 | 0.21 |
| CREMOPHOR EL | Liquid | 1026.8 | 5.13 | 0.5 |
| PLURONIC L44 NF INH | Liquid | 1987.1 | 3.64 | 0.18 |
| LABRAFIL M1944 CS | Liquid | 1011.7 | 0.38 | 0.04 |
| SOFTIGEN 701 | Liquid | 1079.0 | 5.42 | 0.29 |
| MIGLYOL 829 | Liquid | 1865.0 | 0.03 | 0.001 |
| LABRAFAC PG | Liquid | 1961.5 | 0.01 | 0.001 |
| LABRAFIL M2125 | Liquid | 765.2 | 0.17 | 0.02 |
| MIGLYOL 812 | Liquid | 1044.1 | 0.03 | 0.003 |
| SOFTISAN 645 | Liquid | 1014.0 | 1.60 | 0.16 |
| MIGLYOL 810 | Liquid | 602.8 | 0.04 | 0.01 |
| MIGLYOL 840 | Liquid | 599.9 | 0.06 | 0.01 |
| CREMOPHOR RH40 | Semisolid | 1000.4 | 7.72 | 0.77 |
| CREMOPHOR A6 | Semisolid | 1015.3 | 0.00 | 0.00 |
| CREMOPHOR A25 | Semisolid | 995.6 | 2.10 | 0.21 |

The calculations of the mg and of API percentage were made with the following formulas:

$$mg\ API = \frac{A_{sample} * W_{STD} * Potency_{STD} * V_{sample}}{A_{STD} * 100 * 100}$$

$$\%\ API = \frac{mg_{API} * 100}{mg_{suspension\ weight}}$$

Further samples for the solubility evaluation were prepared by adding, under stirring, a quantity of active ingredient (API) suitable to generate a phase segregation to a determined amount of each carrier. The samples were prepared at a temperature slightly above the melting point of each carrier (except for liquid vehicles) and kept at this temperature for about 5 hrs (estimated manufacturing process time). Where applicable, each sample was centrifuged to accelerate phase segregation; an amount of the supernatant, corresponding to the filling weight of a capsule (about 600 mg), was withdrawn and evaluated for assay to determine the amount of API actually dissolved.

Each solubility value is related to a specific temperature, corresponding to the value set for the filling into capsules (see table 14). The results are reported in table 21.b.

TABLE 21.b

Further results of bendamustine hydrochloride solubility in carriers

| Carrier | Solubility (mg API/mg Solution) | T (° C.) |
|---|---|---|
| TWEEN 20 (Liquid) | 0.008 | 25 |
| TWEEN 81 (Liquid) | 0.004 | 25 |
| GLYCEROX HE (Liquid) | 0.005 | 25 |
| BRIJ L4 (Liquid) | 0.008 | 25 |
| PLURONIC L35 (Liquid) | 0.000 | 25 |
| PLURONIC L43 (Liquid) | 0.000 | 25 |

TABLE 21.b-continued

Further results of bendamustine hydrochloride solubility in carriers

| Carrier | Solubility (mg API/mg Solution) | T (° C.) |
|---|---|---|
| PLURONIC L64 (Liquid) | 0.000 | 25 |
| MIRJ S8 (Semisolid) | 0.010 | 42 |
| BRIJ S10 (Solid) | 0.003 | 42 |
| BRIJ O10 (Semisolid) | 0.007 | 45 |
| PLURONIC 103 (Semisolid) | 0.002 | 45 |
| PLURONIC P85 (Semisolid) | 0.002 | 50 |
| PLURONIC P105 (Semisolid) | 0.002 | 50 |
| TWEEN 61 (Semisolid) | 0.019 | 45 |
| TWEEN 40 (Liquid) | 0.007 | 25 |
| MIRJ S40 (Solid) | 0.005 | 50 |
| BRIJ S20 (Solid) | 0.008 | 50 |
| MIRJ S100 (Semisolid) | 0.009 | 50 |
| TWEEN 65 (Liquid) | 0.007 | 45 |
| BRIJ O20 (Semisolid) | 0.006 | 45 |
| BRIJ S721 (Solid) | 0.004 | 45 |
| BRIJ L23 (Solid) | 0.004 | 45 |
| BRIJ C2 (Semisolid) | 0.004 | 45 |
| SOLUTOL HS15 (Semisolid) | 0.007 | 35 |
| SPEZIOL TPGS (Semisolid) | 0.002 | 45 |
| PLURONIC F108 (Solid) | 0.006 | 70 |
| GELUCIRE 44/14 (Semisolid) | 0.004 | 45 |

Visual Appearance During Dissolution Test

In table 22a and 22b are listed brief visual descriptions of the appearance of the solution in the vessel at the end of the dissolution test for the LFHC batches selected for this purpose.

TABLE 22a

Results of visual appearance after dissolution test (I)
Visual appearance during dissolution test

| Batch | Oil liquid floating on the surface | Clear emulsion | Bottom of the vessel | Cloudy emulsion | Particle in suspension | Clear solution |
|---|---|---|---|---|---|---|
| D001L/038 | x | | | | | |
| D001L/039 | | | x | | | |
| D001L/040 | | x | | | | |
| D001L/041 | | x | | | | |
| D001L/042 | x | | | | | |
| D001L/043 | | x | | | | |
| D001L/044 | | x | | | | |
| D001L/045 | | x | | | | |
| D001L/046 | | x | | | | |
| D001L/047 | | x | | | | |
| D001L/048 | | x | | | | |
| D001L/049 | | x | | | | |
| D001L/050 | | | | x | x | |
| D001L/051 | | x | | | | |
| D001L/052 | | x | | | | |

TABLE 22b

Results of visual appearance after dissolution test (II)
Visual appearance during dissolution test

| Batch | Oil liquid floating on the surface | Clear emulsion | Bottom of the vessel | Cloudy emulsion | Particle in suspension | Clear solution |
|---|---|---|---|---|---|---|
| D001L/053 | x | | | | x | |
| D001L/054 | | x | | | | |
| D001L/055 | | | | | | x |
| D001L/056 | x | | | | | |
| D001L/070 | x | | | | | |
| D001L/071 | x | | | | | |
| D001L/072 | x | | | | | |
| D001L/073 | x | | | | | |

TABLE 22b-continued

Results of visual appearance after dissolution test (II)
Visual appearance during dissolution test

| Batch | Oil liquid floating on the surface | Clear emulsion | Bottom of the vessel | Cloudy emulsion | Particle in suspension | Clear solution |
|---|---|---|---|---|---|---|
| D001L/075 |  |  |  |  |  | x |
| D001L/076 |  |  |  |  |  | x |
| D001L/080 |  |  |  |  |  | x |
| D001L/081 |  |  |  |  |  | x |
| D001L/082 |  |  |  |  |  | x |

Conclusions (DL001L/001-092)

Based on the above results, the following conclusions can be reported:

- AEROSIL and GELUCIRE 44/14 can be considered as suitable viscosity increasers for low viscosity oils, to obtain a physically stable vehicle for bendamustine hydrochloride suspension. The addition of Aerosil to some oils resulted in thixotropic carriers, while GELUCIRE 44/14 dissolved in liquid oils turned their physical status into semisolid or solid, depending on its concentration in formulations. The amount of viscosity increaser added to the suspension needs to be adjusted dependent of the initial viscosity of the carrier.
- A high brittleness of the capsules was observed for batches D001L/051, 052, 089 and 092, probably due to the high hygroscopicity of the carriers used.
- The high impurities value of the batch D001L/052 after 3 months of stability is probably due to the incompatibility with bendamustine hydrochloride.
- The sedimentation of the bendamustine hydrochloride seems to affect more the content uniformity of the batch than the dissolution of the capsules.
- The capsules of batches D001L/054 (table 12), D001L/075 and 076 were found to dissolve slightly in the analytical diluents; in fact, after one hour of sonication a large, undissolved, residue was still present. This explains the low value of assay. This could be due to the high viscosity of CREMOPHOR A6 and to its high melting point.
- The impurities of batches based on the aged LABRAFIL M1944 CS and PLURONIC L44 (D001L/074 and D001L/079), on SOFTIGEN 701 (D001L/077), and on carriers with a modified moisture content (D001L/075, 076, 080 and 081) are within the limits at time zero. After three months of stability at 40° C., only the impurities of batch D001L/076 were found to be outside the limit: unexpectedly, the data indicate that increased moisture content of the carrier can be beneficial to the stability of bendamustine. This is probably an anomalous result, because data from the stability study performed to support the Phase I clinical study showed that moisture uptake by the carrier (CREMOPHOR RH 40 in this case) was detrimental to the stability of bendamustine, as would be expected.
- By comparing the dissolution behavior of batches based upon low viscosity carriers and AEROSIL as viscosity increaser (batches from D001L/035 to D001L/049 and D001L/052) with the corresponding ones without AEROSIL (batches from D001L/057 to D001L/068 and D001L/078), it appeared that AEROSIL affects the dissolution time of bendamustine hydrochloride. In spite of the fast dissolution of bendamustine in carriers with low viscosity and without viscosity-increasing agent, the viscosity of the carriers was modified to prevent sedimentation of the bendamustine on storage. It is highly likely that in the long term, the dissolution profile of bendamustine in the LFHC, in the form of a "compacted" sediment, would eventually change to such an extent that the LFHC would no longer comply with the requirements of the drug product specification (target values: NLT 80% after 30 minutes). Therefore, the removal of a viscosity modifier, while improving the dissolution profile, and allowing several alternative carriers to be utilized in the formulation of a drug product, would probably result in LFHCs that were not commercially viable.
- According to the stability results of impurities and dissolution reported, CREMOPHOR EL, PLURONIC L44 NF INH and CREMOPHOR RH40 can be considered the most suitable carriers for commercially viable LFHC formulation. However, CREMOPHOR EL shows an incompatibility with the capsule shell (increase of brittleness) and PLURONIC L44 is liquid at room temperature; CREMOPHOR RH 40 does not increase the brittleness of gelatin capsule shell and is a semi-solid vehicle at room temperature, therefore does not require any viscosity modification because sedimentation of bendamustine hydrochloride in this highly viscous system is unlikely. Despite the high viscosity of this carrier, the dissolution profile of the LFHC is well above the target value of 80%. These aspects can be determinant for a further selection among the three carriers candidates.
- The bendamustine hydrochloride solubility in the selected carriers is very poor: under the 1% of bendamustine hydrochloride was recovered in a supersaturated solution of Bendamustine Hydrochloride in liquid or semi-solid oily vehicles.
- The visual appearance during dissolution highlighted the different behavior of the vehicles in the dissolution medium: its appearance varied from a clear solution, characteristic of some surfactants with high HLB value (such as CREMOPHOR A 25), to a suspension of oily liquid floating on the surface, characteristic of some strongly lipophilic matrixes (such as LABRAFAC PG). Most of the capsules containing AEROSIL resulted in a clear emulsion with water, probably due the effect of viscosity increaser.

Conclusions 9DL0011/093-120)

27 further LFHC batches were manufactured, packaged in aluminium blisters and placed under ambient and accelerated stability conditions up to three months.

While assay and content uniformity values strictly depend on the ability of the suspensions to be processed in the manufacturing and filling equipment, dissolution and impurity profile can be considered as intrinsic features and, therefore, more important in the final evaluation of the suitability of the excipients used (table 9.b) as carrier for Bendamustine hydrochloride.

The results obtained after the stability period at 40° C. and 75% of relative humidity are quite variable. This variability could probably be related to the physico-chemical properties of the different carriers: a possible intrinsically low solubility of the vehicle in the medium or the occurrence of an incompatibility of the carrier with gelatin as well as a higher melting point, could justify the low dissolution of the capsules of batches manufactured with semisolid or solid carriers. As a matter of fact, an additional step of 30 minutes at 200 rpm has been necessary for most of the batches produced because an insufficient release of the API after 30' was observed. However, some formulations containing semisolid or solid carriers (e.g. batches No. D001L/107, 111, 112, 115 and 116) showed a low dissolution rate also after the fast point. Probably the physico-chemical characteristics of the solid and semisolid carriers contained in some capsules batches changed in the storage conditions above mentioned: while the undissolved residual left by capsules of batches D001L/094, 095, 102, 103, 104, 106, 107, 108, 111, 112, 115 and 116 in the flask, at the end of the sample preparation for the evaluation of assay could explain the low assay value, batches D001L/102, 103, 104, 112 show higher assay value.

Impurity profiles showed a general increase of unknown impurity compared to time zero. Furthermore, batches D001L/097, 099, 100 showed high levels for HP1 probably due to an increase of the humidity during stability time. Possible chemical incompatibilities could have generated in several batches (e.g. D001L/093, 094, 095, 097, 098, 099, 100, 101, 103, 104, 106, 109, 110, 111 and 113) a high level for BM1EE dimer and major unknown impurity. However, as above mentioned, the analytical methodologies applied for determination of assay, content uniformity and impurity profile of the manufactured batches were previously developed and optimized for capsule formulations containing CREMOPHOR RH40 as the carrier.

For all batches, the moisture content after 3 months at 40° C. and 75% RH increases with respect to the results obtained at time zero. Assuming the aluminium blisters as the most suitable package against moisture penetration, probably a redistribution of the moisture between the shell and the capsule content could have occurred. For batches D001L/093 to D001L/104, D001L/106 to D001L/112 and D001L/115 to D001L/119, this aspect could also be explained by considering the high hygroscopicity of the corresponding carrier.

The capsules filled with only Bendamustine hydrochloride do not show a change in impurity profile and dissolution behavior compared to time zero.

As expected, Bendamustine HCl is poorly soluble in each selected carrier, probably due to its hydrophilicity.

The poor dissolution results for most of the batches demonstrate that most of the excipients tested are not suitable as a vehicle for Bendamustine HCl in liquid filled hard capsule formulations, that are stable and show fast dissolution.

2. Disintegration and Dissolution Tests

Example 5

Disintegration tests for the liquid filled capsule formulations of examples 1, 2 and 3 were carried out in 1000.0 ml of buffer solution pH=1.0±0.05, using disintegration Apparatus A, operated at 37.0° C.±0.5° C. The results are listed in Tables 23a, 23b and 23c.

Example 6

Dissolution tests for the liquid filled capsule formulations of examples 1, 2 and 3 were carried out in artificial gastric acid solution at pH 1.5 (see Ph Eur: 2.9.3: Dissolution test for solid dosage forms in Recommended Dissolution Media).

The dissolution samples were tested for assay by HPLC (column: Zorbax Bonus-RP, 5 μm; temperature of column oven: 30° C.; temperature of autosampler: 5° C.; detector: 254 nm). Artificial gastric fluid pH 1.5 was prepared by placing 250.0 mL of 0.2M potassium chloride 0.2M into a 1000 mL volumetric flask, adding 207.0 mL of 0.2 M hydrochloric acid, then diluting to 1000 mL with Milli-Q water. The pH was measured and adjusted, if necessary, with 2N hydrochloric acid or 2N potassium hydroxide to a pH of 1.5±0.05.

The dissolution test was conducted according to Chapter 2.9.3. of European Pharmacopoeia 6.0, using Apparatus 2 (Paddle-apparatus). The rotation speed of the paddle was 50 rpm, the temperature was 37° C.±0.5° C., the amount of dissolution medium was 500 ml.

The results for the liquid filled hard capsules of examples 1, 2 and 3 are shown in Tables 23a, 23b and 23c:

TABLE 23a

Liquid filled hard capsules of example 1

| Test | Time | |
|---|---|---|
| | T = 0 months | T = 3 months |
| Temperature 40° C. 75% RH | | |
| Disintegration (minute:second) | 03:23 | 03:30 |
| Dissolution (%) pH 1.5 | | |
| 10' | Not tested | 10.4 |
| 20' | | 35.1 |
| 30' | | 51.1 |
| Temperature 30° C. 65% RH | | |
| Disintegration (minute:second) | 03:23 | 03:26 |
| Dissolution (%) pH 1.5 | | |
| 10' | Not tested | 7.0 |
| 20' | | 24.0 |
| 30' | | 54.6 |
| Temperature 25° C. 60% RH | | |
| Disintegration (minute: second) | 03:23 | 03:33 |
| Dissolution (%) pH 1.5 | | |
| 10' | Not tested | 37.4 |
| 20' | | 52.4 |
| 30' | | 71.6 |
| Temperature 5° C. | | |
| Disintegration (minute:second) | 03:23 | 03:23 |
| Dissolution (%) pH 1.5 | | |
| 10' | Not tested | 57.0 |
| 20' | | 76.7 |
| 30' | | 83.1 |

TABLE 23b

Liquid filled hard capsule of example 2

| Test | Time | |
|---|---|---|
| | T = 0 months | T = 3 months |
| Temperature 40° C. 75% RH | | |
| Disintegration (minute:second) | 03:52 | 02:58 |
| Dissolution (%) pH 1.5 | | |
| 10' | Not tested | 65.2 |
| 20' | | 88.7 |
| 30' | | 102.0 |

TABLE 23b-continued

Liquid filled hard capsule of example 2

| Test | Time | |
|---|---|---|
| | T = 0 months | T = 3 months |
| Temperature 30° C. 65% RH | | |
| Disintegration (minute:second) Dissolution (%) pH 1.5 | 03:52 | 03:09 |
| 10' | Not tested | 48.1 |
| 20' | | 80.9 |
| 30' | | 93.7 |
| Temperature 25° C. 60% RH | | |
| Disintegration (minute:second) Dissolution (%) pH 1.5 | 03:52 | 02:53 |
| 10' | Not tested | 54.5 |
| 20' | | 80.7 |
| 30' | | 94.4 |
| Temperature 5° C. | | |
| Disintegration (minute:second) Dissolution (%) pH 1.5 | 03:52 | 02:56 |
| 10' | Not tested | 57.9 |
| 20' | | 90.0 |
| 30' | | 98.0 |

TABLE 23c

Liquid filled hard capsule of example 3

| Test | Time | |
|---|---|---|
| | T = 0 months | T = 3 months |
| Temperature 40° C. 75% RH | | |
| Disintegration (minute:second) Dissolution (%) pH 1.5 | 03:59 | 03:36 |
| 10' | Not tested | 28.5 |
| 20' | | 49.1 |
| 30' | | 62.9 |
| Temperature 30° C. 65% RH | | |
| Disintegration (minute:second) Dissolution (%) pH 1.5 | 03:59 | 03:34 |
| 10' | Not tested | 17.5 |
| 20' | | 35.2 |
| 30' | | 58.1 |
| Temperature 25° C. 60% RH | | |
| Disintegration (minute:second) Dissolution (%) pH 1.5 | 03:59 | 03:27 |
| 10' | Not tested | 25.9 |
| 20' | | 44.2 |
| 30' | | 62.1 |
| Temperature 5° C. | | |
| Disintegration (minute:second) Dissolution (%) pH 1.5 | 03:59 | 03:18 |
| 10' | Not tested | 15.9 |
| 20' | | 31.1 |
| 30' | | 46.6 |

As may be taken from the above Tables 23a, 23b and 23c, only the liquid filled hard capsule formulation of example 2 according to the invention shows the preferred fast dissolution profile of bendamustine, which is at least 60% in 10 minutes, 70% in 20 minutes and 80% in 30 minutes, as measured with a paddle apparatus at 50 rpm according to the European Pharmacopoeia in 500 ml of an artificial gastric fluid.

3. In Vivo Tests

Example 7

The liquid filled hard capsules of example 2, containing 50 mg of bendamustine, were orally administered to male and female beagle dogs in comparison with the capsules of reference example 1 in order to determine the bioavailability of 1 dose (i.e. 50 mg) of bendamustine (AUC and Cmax) and to determine the level of variability in bioavailability of these capsule formulations: (i.e. % CV on AUC and Cmax). A further formulation (formulation X) was also included in the test but since this formulation was outside the scope of the present invention no details are provided. The total number of animals required was 16.

The basic study design was a cross-over design with 8 animals per arm.

Period 1 (Single Dose of Capsule, Day 1):

| Group | Treatment | Composition | Dose # (mg) | Number of animals |
|---|---|---|---|---|
| 1 | Bendamustine | Reference Capsule | 50 | 4 Male + 4 Female |
| 2 | Bendamustine | Reference Capsule | 50 | 4 Male + 4 Female |

There was a one week wash-out period.
Period 2 (1 Week after Period 1, Single Dose of Either of the Following Formulations, Day 8):

| Group | Treatment | Composition | Dose # (mg) | Number of animals |
|---|---|---|---|---|
| 1 | Bendamustine | Formulation example 2 | 50 | 4 Male + 4 Female |
| 2 | Bendamustine | Formulation X | 50 | 4 Male + 4 Female |

The mean plasma profiles vs. time for both the capsule formulation (reference example 1) and the liquid filled capsule formulation of Example 2 are shown in FIG. 1.

Example 8

An open label, randomized two-way crossover study to assess the absolute bioavailability of oral bendamustine in patients with cancer was conducted to assess the absolute bioavailability of bendamustine administered as an oral formulation (example 2). Besides assessing the pharmacokinetics of bendamustine in plasma following oral and i.v. administration, a further objective was to evaluate the safety and tolerability of bendamustine following i.v. and especially oral administration of the formulation of example 2.

A total of 12 patients was planned for the phase 1, open-label, randomised, 2-way crossover study to investigate the bioavailability of bendamustine after oral administration of a liquid-filled hard capsule formulation of bendamustine hydrochloride. 14 patients who were suffering from multiple myeloma, B-cell type chronic lymphocytic leukemia or advanced indolent non-Hodgkin's lymphoma were enrolled and were treated with bendamustine. Patients were allowed to be previously treated with intravenous bendamustine, but should have received their last intravenous cycle at least 7 days before the first administration of study drug. After signing the informed consent form and following the screening period (days −21 to −2), eligible patients were assigned a patient number which was specific for each study site. Patients were randomized to receive one of the following on day 1 followed by the other on day 8:

a single oral dose of 110.2 mg (2×55.1 mg) bendamustine HCl a single intravenous dose of 100 mg bendamustine HCl Bendamustine was provided a) orally as capsules, a LFHC formulation (liquid-filled, hard-shell capsule) and b) intravenously as a solution after reconstituting a powder for the preparation of a solution for injection. The LFHC formulation (per capsule) was prepared from 55.1 mg bendamustine hydrochloride, 1.2 mg methylparaben, 0.12 mg polyparaben, 0.12 mg butylated hydroxytoluene, 10.9 mg ethanol and 532.56 mg CREMOPHOR RH40. The vial with powder for concentrate for solution was the marketed product in Germany (RIBOMUSTINE) which contains per vial 100 mg of bendamustine hydrochloride and mannitol as an excipient. This product was reconstituted with water for injection to a final concentration of 2.5 mg/ml of bendamustine HCl and was further diluted with 0.9% NaCl until about 500 ml before administration to the patient, in accordance with the instructions of the package insert.

Patients were admitted to the study site for 2 periods; days −1 to 2 (period 1) and days 7 to 9 (period 2). A total of 12 patients was to be randomized to receive treatment. Six patients were to receive treatment with a single oral dose of 110.2 mg (2×55.1 mg) bendamustine HCl (day 1) followed by a single intravenous dose of 100 mg bendamustine HCl (day 8) while 6 other patients were to receive treatment in the alternate order. Patients underwent a washout period of at least 7 days between treatments.

Bendamustine is metabolized via hydrolysis to the inactive metabolites monohydroxybendamustine (HP1) and dihydroxybendamustine (HP2) and via cytochrome P450 (CYP 1A2) to the active metabolites γ-hydroxybendamustine (M3) and N-desmethylbendamustine (M4).

After oral and intravenous administration of bendamustine the concentration of bendamustine, as well as that of the active metabolites of bendamustine (M3 and M4), were determined in plasma and urine samples on day 1 and day 8. Patients returned to the study site for an end-of-study visit 7 to 14 days after completion of the second treatment period, or after early discharge/withdrawal. Subsequently the pharmacokinetic parameters of bendamustine and its metabolites were calculated.

No interim analyses were planned or conducted.

The following results were obtained:

Population:

Of the 23 patients screened for this study, 14 patients were randomly assigned to treatment and received at least 1 dose of study medication. These included 6 patients receiving the oral/intravenous sequence and 8 patients receiving the intravenous/oral sequence. Of these 14 patients:

1 was excluded due to a protocol violation (concomitant medication) and received oral medication only, so no intravenous administration;

1 was excluded from the oral analysis due to vomiting and di not qualify for the bioavailability assessment and 1 was excluded from the intravenous administration due to an adverse event. This patient received oral dosing only, no intravenous.

Ten (71%) of the 14 patients were male, and all were white. Patient ages ranged from 54 to 82, with a mean of approximately 70 years. Seven of the patients had multiple myeloma, 4 had indolent non-Hodgkin's lymphoma and 3 had chronic lymphocytic leukemia.

Pharmacokinetic Results:

Plasma pharmacokinetic parameters of bendamustine (base), M3 and M4 are shown in Table 24, Table 25 and Table 26, respectively. Based on statistical analysis, the absolute bioavailability (oral versus intravenous ratio of $AUC_{inf}$) of bendamustine was 66% (geometric mean; 90% CI: 55%, 78%). $C_{max}$ after oral dosing was 42% of $C_{max}$ after intravenous dosing (90% CI: 32%, 54%).

TABLE 24

Plasma Pharmacokinetic Parameters for Bendamustine

| Treatment | Statistic | $t_{max}$ (h) | $C_{max}$ (ng/mL) | $AUC_{last}$ (ng · h/mL) | $AUC_{inf}$ (ng · h/mL) |
|---|---|---|---|---|---|
| Bendamustine HCl, 110.2 mg orally | n | 12 | 12 | 12 | 12 |
| | Mean | 0.946 | 3173‡ | 3893 | 3901 |
| | SD | 0.4833 | 1767 | 1929 | 1930 |
| | | $t_{1/2}$ (h) | CL/F (L/h) | $V_z$/F (L) | F (%) |
| | n | 12 | 12 | 12 | 11 |
| | Mean | 0.461 | 31.7 | 20.2 | 69.0† |
| | SD | 0.107 | 14.5 | 7.9 | 17.9 |
| | Statistic | $t_{max}$ (h) | $C_{max}$ (ng/mL) | $AUC_{last}$ (ng · h/mL) | $AUC_{inf}$ (ng · h/mL) |
| Bendamustine HCl, 100 mg intravenously | n | 11 | 11 | 11 | 11 |
| | Mean | 0.524 | 5900‡ | 4785 | 4793 |
| | SD | 0.119 | 1823 | 1689 | 1691 |
| | | $t_{1/2}$ (h) | CL (L/h) | $V_z$ (L) | $V_{ss}$ (L) |
| | n | 11 | 11 | 11 | 10 |
| | Mean | 0.504 | 21.2 | 14.7 | 10.3 |
| | SD | 0.143 | 7.4 | 4.1 | 3.2 |

Notes:

All patients who received at least 1 dose of study drug and who had sufficient plasma concentration data available to derive at least 1 pharmacokinetic parameter, excluding 1 patient whose pharmacokinetic data were considered unreliable due to an AE of vomiting (modified pharmacokinetic analysis set).

†Arithmetic mean. Geometric mean was 66% (90% CI: 55%, 78%).

‡$C_{max}$ after oral dosing was 42% of $C_{max}$ after intravenous dosing (90% CI: 32%, 54%).

Notes:

† Arithmetic mean. Geometric mean was 66% (90% CI: 55%, 78%).

‡ $C_{max}$ after oral dosing was 42% of $C_{max}$ after intravenous dosing (90% CI: 32%, 54%).

All patients who received at least 1 dose of study drug and who had sufficient plasma concentration data available to derive at least 1 pharmacokinetic parameter, excluding 1 patient whose pharmacokinetic data were considered unreliable due to an AE of vomiting (modified pharmacokinetic analysis set).

TABLE 25

Plasma Pharmacokinetic Parameters for M3

| Treatment | Statistic | $t_{max}$ (h) | $C_{max}$ (ng/mL) | $AUC_{last}$ (ng · h/mL) | $AUC_{inf}$ (ng · h/mL) | $t_{1/2}$ (h) |
|---|---|---|---|---|---|---|
| Bendamustine | n | 11 | 11 | 11 | 11 | 11 |
| HCl, 110.2 mg | Mean | 1.27 | 243 | 367 | 369 | 0.643 |
| orally | SD | 0.45 | 149 | 194 | 194 | 0.285 |
| Bendamustine | n | 11 | 11 | 11 | 11 | 11 |
| HCl, 100 mg | Mean | 0.823 | 344 | 370 | 372 | 0.727 |
| intravenously | SD | 0.221 | 193 | 178 | 179 | 0.426 |

Notes:
All patients who received at least 1 dose of study drug and who had sufficient plasma concentration data available to derive at least 1 pharmacokinetic parameter, excluding 1 patient whose pharmacokinetic data were considered unreliable due to an AE of vomiting (modified pharmacokinetic analysis set).

TABLE 26

Plasma Pharmacokinetic Parameters for M4

| Treatment | Statistic | $t_{max}$ (h) | $C_{max}$ (ng/mL) | $AUC_{last}$ (ng · h/mL) | $AUC_{inf}$ (ng · h/mL) | $t_{1/2}$ (h) |
|---|---|---|---|---|---|---|
| Bendamustine | n | 11 | 11 | 11 | 11 | 11 |
| HCl, 110.2 mg | Mean | 1.325 | 26.9 | 42.8 | 44.4 | 0.515 |
| orally | SD | 0.449 | 19.9 | 29.6 | 29.6 | 0.134 |
| Bendamustine | n | 11 | 11 | 11 | 11 | 11 |
| HCl, 100 mg | Mean | 0.935 | 33.6 | 40.8 | 42.5 | 0.543 |
| intravenously | SD | 0.198 | 20.0 | 22.9 | 22.6 | 0.097 |

Notes:
All patients who received at least 1 dose of study drug and who had sufficient plasma concentration data available to derive at least 1 pharmacokinetic parameter, excluding 1 patient whose pharmacokinetic data were considered unreliable due to an AE of vomiting (modified pharmacokinetic analysis set).

After oral administration, bendamustine was absorbed with a $t_{max}$ of approximately 0.95 hours, with individual values ranging between 15 minutes and 1.8 hours. Mean CL after intravenous administration was 21.2 L/h. Mean$_{t1/2}$ was approximately 30 minutes, both after oral intake and after intravenous administration. Mean $V_Z$ and $V_{SS}$ after intravenous administration were 14.7 L and 10.3 L respectively.

M3 and M4 exposure in plasma was considerably lower than for bendamustine. Mean $AUC_{inf}$ of bendamustine was 10.6 and 88 times higher than for M3 and M4, respectively, after oral administration. In contrast to bendamustine, M3 and M4 $AUC_{inf}$ values were similar for oral and intravenous administration. Based on statistical analysis, after oral administration $AUC_{inf}$ of M3 was 86% of $AUC_{inf}$ after intravenous administration (90% CI: 76%, 98%). For M4 this was 88% (90% CI: 77%, 102%).

Urine pharmacokinetic parameters of bendamustine, M3 and M4 are presented in Table 27, Table 28 and Table 29, respectively. The percentage of the dose excreted in urine unchanged was low (2.6% and 2.1% for oral and intravenous bendamustine, respectively).

TABLE 27

Urine Pharmacokinetic Parameters for Bendamustine

| Treatment | Statistic | $Ae_{last}$ (mg) | % $Ae_{last}$ (%) | $Ae_{inf}$ (mg) | % $Ae_{inf}$ (%) | $CL_R$ (L/h) |
|---|---|---|---|---|---|---|
| Bendamustine | n | 11 | 11 | 11 | 11 | 11 |
| HCl, 110.2 mg | Mean | 2.66 | 2.66 | 2.64 | 2.64 | 0.788 |
| orally | SD, CV % | 1.64, 62 | 1.64, 62 | 1.63, 62 | 1.63, 62 | 0.573, 73 |
| | Min-max | 0.40-5.9 | 0.40-5.9 | 0.40-5.8 | 0.40-5.8 | 0.18-2.0 |
| | Median | 2.23 | 2.23 | 2.23 | 2.23 | 0.782 |
| Bendamustine | n | 11 | 11 | 11 | 11 | 11 |
| HCl, 100 mg | Mean | 1.88 | 2.07 | 1.874 | 2.07 | 0.385 |
| intravenously | SD, CV % | 2.29, 122 | 2.52, 122 | 2.28, 122 | 2.52, 122 | 0.414, 108 |
| | Min-max | 0.24-8.0 | 0.27-8.8 | 0.24-8.0 | 0.27-8.8 | 0.06-1.4 |
| | Median | 1.12 | 1.23 | 1.11 | 1.22 | 0.202 |

Notes:
All patients who received at least 1 dose of study drug and who had sufficient plasma concentration data available to derive at least 1 pharmacokinetic parameter, excluding 1 patient whose pharmacokinetic data were considered unreliable due to an AE of vomiting (modified pharmacokinetic analysis set).

TABLE 28

Urine Pharmacokinetic Parameters for M3

| Treatment | Statistic | $Ae_{last}$ (mg) | % $Ae_{last}$ (%) | $Ae_{inf}$ (mg) | % $Ae_{inf}$ (%) | $CL_R$ (L/h) |
|---|---|---|---|---|---|---|
| Bendamustine HCl, 110.2 mg orally | n | 10 | 10 | 10 | 10 | 10 |
| | Mean | 0.635 | 0.61 | 0.636 | 0.611 | 2.14 |
| | SD, CV % | 0.409, 64 | 0.393, 64 | 0.407, 64 | 0.391, 64 | 2.08, 97 |
| | Min-max | 0.13-1.7 | 0.12-1.6 | 0.13-1.6 | 0.13-1.5 | 0.45-7.4 |
| | Median | 0.576 | 0.553 | 0.558 | 0.537 | 1.49 |
| Bendamustine HCl, 100 mg intravenously | n | 11 | 11 | 11 | 11 | 11 |
| | Mean | 0.433 | 0.457 | 0.435 | 0.459 | 1.29 |
| | SD, CV % | 0.435, 100 | 0.459, 100 | 0.441, 101 | 0.466, 101 | 1.44, 112 |
| | Min-max | 0.017-1.5 | 0.018-1.6 | 0.017-1.6 | 0.018-1.6 | 0.082-5.2 |
| | Median | 0.334 | 0.353 | 0.336 | 0.354 | 0.856 |

Notes:
All patients who received at least 1 dose of study drug and who had sufficient plasma concentration data available to derive at least 1 pharmacokinetic parameter, excluding 1 patient whose pharmacokinetic data were considered unreliable due to an AE of vomiting (modified pharmacokinetic analysis set).

TABLE 29

Urine Pharmacokinetic Parameters for M4

| Treatment | Statistic | $Ae_{last}$ (mg) | % $Ae_{last}$ (%) | $Ae_{inf}$ (mg) | % $Ae_{inf}$ (%) | $CL_R$ (L/h) |
|---|---|---|---|---|---|---|
| Bendamustine HCl, 110.2 mg orally | n | 10 | 10 | 10 | 10 | 10 |
| | Mean | 0.109 | 0.113 | 0.105 | 0.109 | 2.83 |
| | SD, CV % | 0.058, 54 | 0.060, 54 | 0.052, 50 | 0.054, 50 | 1.96, 69 |
| | Min-max | 0.019-0.21 | 0.019-0.21 | 0.033-0.21 | 0.034-0.22 | 0.78-7.1 |
| | Median | 0.1 | 0.104 | 0.1 | 0.104 | 2.24 |
| Bendamustine HCl, 100 mg intravenously | n | 11 | 11 | 11 | 11 | 11 |
| | Mean | 0.075 | 0.086 | 0.071 | 0.081 | 1.74 |
| | SD, CV % | 0.067, 89 | 0.077, 89 | 0.057, 81 | 0.066, 81 | 1.44, 83 |
| | Min-max | 0.0025-0.18 | 0.0028-0.21 | 0.0034-0.15 | 0.0039-0.17 | 0.18-5.3 |
| | Median | 0.038 | 0.043 | 0.039 | 0.045 | 1.66 |

Notes:
All patients who received at least 1 dose of study drug and who had sufficient plasma concentration data available to derive at least 1 pharmacokinetic parameter, excluding 1 patient whose pharmacokinetic data were considered unreliable due to an AE of vomiting (modified pharmacokinetic analysis set).

Safety Results:

Both oral and intravenous administrations of bendamustine were safe and well tolerated. Overall, 6 patients (43%) experienced treatment-emergent adverse events during oral treatment and 3 patients (25%) experienced treatment-emergent adverse events during intravenous treatment. Four patients (29%) receiving the oral dose and no patients receiving the intravenous dose experienced at least 1 adverse event that was considered by the investigator to be related to study drug; these included headache in 1 patient, both headache and fatigue in 1 patient, nausea in 1 patient and vomiting in 1 patient. These events were Grade 1 in severity except for vomiting, which was Grade 2 in severity.

Most adverse events were Grade 1 or Grade 2 in severity. One patient receiving the oral dose experienced Grade 3 increased serum creatinine, hypokalemia, and acute renal failure, and Grade 4 thrombocytopenia, all considered by the investigator to be related to the patient's multiple myeloma and unrelated to study drug. The increased serum creatinine and acute renal failure were severe adverse events, leading to the patient's premature discontinuation from the study. No deaths occurred during the study.

No clinically meaningful trends were observed in mean changes from baseline or categorical shifts for any hematology, biochemistry, urinalysis, or vital sign parameter. A few patients had abnormal hematology or biochemistry findings that were reported as adverse events; none of these were considered to be related to study drug by the investigator.

Mean changes from baseline in heart rate were small and similar between treatment groups. Due to the age and medical history of the patients in this study, most had at least 1 electrocardiogram finding of "abnormal, not clinically significant" at screening and/or during the study. In 1 patient in the intravenous/oral group, abnormal, clinically significant atrial fibrillation, nonspecific ST depression and left axis deviation was observed at screening and following both the intravenous and oral doses.

CONCLUSIONS

Absolute bioavailability of bendamustine after single oral administration using the capsule was 66% (geometric mean; 90% CI: 55%, 78%).

Mean bendamustine CL, Vz and Vss after intravenous administration were 21.2 L/h, 14.7 L and 10.3 L, respectively.

Bendamustine was quickly absorbed after oral administration (median $t_{max}$ approximately 0.95 hours). Mean $t_{1/2}$ was approximately 30 minutes. Approximately 2.6% of the dose was excreted in urine unchanged after oral administration, while 0.6% was excreted as M3 and 0.1% was excreted as M4. M3 and M4 exposure were approximately 9% and 1% that of bendamustine, respectively, after oral administration.

Based on adverse events reporting, clinical laboratory evaluations, vital signs, physical examinations and electrocardiograms, single doses of both the oral (110.2 mg) and intravenous (100 mg) forms of bendamustine were shown to be safe and well tolerated in this mostly elderly population of patients with indolent non-Hodgkin's lymphoma, multiple myeloma or B-cell type chronic lymphocytic leukemia.

INDUSTRIAL APPLICABILITY

The compositions according to the present invention show many advantages. They can be easily used by the patient without assistance of supervisory medical staff. Hence the time-consuming trips to the hospital may become obsolete, thereby increasing the patient compliance. Further there is the advantage that hospital staff is less exposed to the contact with the cytotoxic material, thereby decreasing occupational hazards. Also there is less environmental hazard, as no vials containing the cytotoxic compound need to be discarded.

The dosage forms can be swallowed as such, which means that the patient does not need to wait until dissolution of the active ingredient has been achieved. On top of that swallowing the medication is a preferred way of taking it, in order to avoid any contact of the active ingredient with the oral mucosa. Further due to the good stability of the dosage forms they can be easily stored at room temperature and without the need of any special storage conditions.

By using the dosage forms according to the present invention, a considerable reduction of the volume of the dosage form may be achieved. The reduced size is desirable both from a manufacturing and handling standpoint and patient compliance.

Pharmaceutical compositions show a high dissolution in vitro which should reduce the degradation of bendamustine in vivo. Thus the inventive compositions may show an improved bioavailability profile of the bendamustine in vivo, as compared to prior art oral formulations.

The invention claimed is:

1. An oral pharmaceutical composition having a fast dissolution profile comprising
   (i) bendamustine hydrochloride as an active ingredient, and
   (ii) a pharmaceutically acceptable non-ionic hydrophilic surfactant selected from the group consisting of propylene glycol dicaprylocaprate, propylene glycol monolaurate, linoleoyl macrogol glycerides, oleoyl macrogolglycerides, diethylene glycol monobutylether, diethylene glycol monoethylether, diethylene glycol monomethylether, polysorbate 20, macrogol glyceryl cocoates, poloxamer 105, poloxamer 184, and polysorbate 40,
   wherein 99% or more of bendamustine hydrochloride is present as solids that are homogeneously suspended in the pharmaceutical composition, the pharmaceutical composition does not include a viscosity improving agent, and the dissolution of bendamustine hydrochloride is at least 80% after 30 minutes, as measured with a paddle apparatus at 50 rpm according to the European Pharmacopoeia in 500 ml of a dissolution medium at a pH of 1.5.

2. The pharmaceutical composition according to claim 1, wherein the pharmaceutical composition comprises 10 to 1000 mg of the active ingredient.

3. The pharmaceutical composition according to claim 1, wherein the composition is in a hard gelatine capsule.

4. The pharmaceutical composition according to claim 1, wherein the pharmaceutical composition exhibits a dissolution of bendamustine hydrochloride of at least 80% after 60 minutes, as measured with a paddle apparatus at 50 rpm during 30 minutes, followed by 200 rpm during a further 30 minutes, according to the European Pharmacopoeia in 500 ml of a dissolution medium at a pH of 1.5.

5. The pharmaceutical composition according to claim 1, wherein the pharmaceutical composition exhibits a dissolution profile of bendamustine hydrochloride of at least 60% dissolved after 20 minutes, and 80% after 60 minutes, as measured with a paddle apparatus at 50 rpm according to the European Pharmacopoeia in 500 ml of a dissolution medium at a pH of 1.5.

6. The pharmaceutical composition according to claim 5, wherein the dissolution of bendamustine hydrochloride is at least 80% after 30 minutes.

7. The pharmaceutical composition according to claim 1, wherein the amount of bendamustine hydrochloride released following administration to a human is sufficient for the treatment of a medical condition which is selected from the group consisting of chronic lymphocytic leukemia, acute lymphocytic leukaemia, chronic myelocytic leukaemia, acute myelocytic leukaemia, Hodgkin's disease, non-Hodgkin's lymphoma, multiple myeloma, breast cancer, ovarian cancer, small cell lung cancer and non-small cell lung cancer.

8. The pharmaceutical composition according to claim 1, wherein the pharmaceutical composition is administered in combination with at least one further active agent, wherein said further active agent is given prior, concurrently, or subsequently to the administration of the pharmaceutical composition and is selected from the group consisting of an antibody specific for CD20, an anthracyclin derivative, a vinca alkaloid or a platin derivative.

9. The pharmaceutical composition according to claim 7, wherein the antibody specific for CD20 is rituximab; the anthracyclin derivative is doxorubicin or daunorubicin; the vinca alkaloid is vincristine and the platin derivative is cisplatin or carboplatin.

10. The pharmaceutical composition according to claim 1, which is administered in combination with at least one corticosteroid, wherein said corticosteroid is given prior, concurrently, or subsequently to the administration of the pharmaceutical composition.

11. The pharmaceutical composition according to claim 9, wherein the corticosteroid is prednisone or prednisolone.

12. The pharmaceutical composition according to claim 1, wherein the pharmaceutically acceptable non-ionic hydrophilic surfactant is selected from the group consisting of propylene glycol dicaprylocaprate, propylene glycol monolaurate, linoleoyl macrogol glycerides, oleoyl macrogolglycerides, diethylene glycol monobutylether, diethylene glycol monoethylether, diethylene glycol monomethylether, macrogol glyceryl cocoates, poloxamer 105, poloxamer 184, and polysorbate 40.

13. A pharmaceutical composition formulated for oral administration comprising bendamustine hydrochloride as an active ingredient, and
   a pharmaceutically acceptable non-ionic hydrophilic surfactant selected from the group consisting of propylene glycol dicaprylocaprate, propyleneglycol monolaurate, linoleoyl macrogol glycerides, oleoyl macrogolglycerides, diethyleneglycol monobutylether, diethylene glycol monoethylether, diethylene glycol monomethylether, polysorbate 20, and macrogol glyceryl cocoates,
   wherein 99% or more of the bendamustine hydrochloride in the pharmaceutical composition is present as solids that are homogeneously suspended in the pharmaceutical composition, the pharmaceutical composition does not include a viscosity improving agent, and the dissolution of bendamustine hydrochloride is at least 80% after 30 minutes, as measured with a paddle apparatus at 50 rpm according to the European Pharmacopoeia in 500 ml of a dissolution medium at a pH of 1.5.

14. The pharmaceutical composition according to claim 1, wherein the pharmaceutically acceptable non-ionic hydrophilic surfactant is selected from the group consisting of linoleoyl macrogol glycerides, oleoyl macrogolglycerides, diethylene glycol monobutylether, diethylene glycol monoethylether, diethylene glycol monomethylether, and macrogol glyceryl cocoates.

15. The pharmaceutical composition according to claim 1, wherein the pharmaceutically acceptable non-ionic hydrophilic surfactant is selected from the group consisting of propylene glycol dicaprylocaprate, diethylene glycol monobutylether, diethylene glycol monoethylether, diethylene glycol monomethylether, polysorbate 20, macrogol glyceryl cocoates, poloxamer 105, poloxamer 184, and polysorbate 40.

16. An oral pharmaceutical composition having a fast dissolution profile comprising
  (i) bendamustine hydrochloride as an active ingredient, and
  (ii) a pharmaceutically acceptable non-ionic hydrophilic surfactant selected from the group consisting of linoleoyl macrogol glycerides, oleoyl macrogolglycerides, diethylene glycol monobutylether, diethylene glycol monoethylether, diethylene glycol monomethylether, and macrogol glyceryl cocoates, and
  wherein 99% or more of the bendamustine hydrochloride is present as solids that are homogeneously suspended in the pharmaceutical composition, the pharmaceutical composition does not include a viscosity improving agent, and the dissolution of bendamustine hydrochloride is at least 80% after 30 minutes, as measured with a paddle apparatus at 50 rpm according to the European Pharmacopoeia in 500 ml of a dissolution medium at a pH of 1.5.

17. An oral pharmaceutical composition having a fast dissolution profile consisting essentially of
  (i) bendamustine hydrochloride as an active ingredient, and
  (ii) a pharmaceutically acceptable non-ionic hydrophilic surfactant selected from the group consisting of propylene glycol dicaprylocaprate, propylene glycol monolaurate, linoleoyl macrogol glycerides, oleoyl macrogolglycerides, diethylene glycol monobutylether, diethylene glycol monoethylether, diethylene glycol monomethylether, polysorbate 20, macrogol glyceryl cocoates, poloxamer 105, poloxamer 184, and polysorbate 40,
  wherein 99% or more of the bendamustine hydrochloride is present as solids that are homogeneously suspended in the pharmaceutical composition, the pharmaceutical composition does not include a viscosity improving agent, and the dissolution of bendamustine hydrochloride is at least 80% after 30 minutes, as measured with a paddle apparatus at 50 rpm according to the European Pharmacopoeia in 500 ml of a dissolution medium at a pH of 1.5.

18. An oral pharmaceutical composition having a fast dissolution profile comprising
  (i) bendamustine hydrochloride as an active ingredient, and
  (ii) a pharmaceutically acceptable non-ionic hydrophilic surfactant selected from the group consisting of propylene glycol dicaprylocaprate, propylene glycol monolaurate, linoleoyl macrogol glycerides, oleoyl macrogolglycerides, diethylene glycol monobutylether, diethylene glycol monoethylether, diethylene glycol monomethylether, polysorbate 20, macrogol glyceryl cocoates, poloxamer 105, poloxamer 184, and polysorbate 40,
  wherein 99% or more of the bendamustine hydrochloride is present as solids that are homogeneously suspended in the pharmaceutical composition, the pharmaceutical composition does not include a viscosity improving agent,
  the pharmaceutical composition exhibits a dissolution profile of the bendamustine hydrochloride of at least 60% dissolved after 20 minutes, and 80% after 60 minutes, as measured with a paddle apparatus at 50 rpm according to the European Pharmacopoeia in 500 ml of a dissolution medium at a pH of 1.5, and
  the dissolution of the bendamustine hydrochloride is at least 80% after 30 minutes as measured with a paddle apparatus at 50 rpm according to the European Pharmacopoeia in 500 ml of a dissolution medium at a pH of 1.5.

* * * * *